United States Patent
Yun et al.

(10) Patent No.: US 10,401,309 B2
(45) Date of Patent: Sep. 3, 2019

(54) X-RAY TECHNIQUES USING STRUCTURED ILLUMINATION

(71) Applicant: Sigray, Inc., Concord, CA (US)

(72) Inventors: Wenbing Yun, Walnut Creek, CA (US); Sylvia Jia Yun Lewis, San Francisco, CA (US); Janos Kirz, Berkeley, CA (US)

(73) Assignee: Sigray, Inc., Concord, CA (US)

( * ) Notice: Subject to any disclaimer, the term of this patent is extended or adjusted under 35 U.S.C. 154(b) by 415 days.

(21) Appl. No.: 15/173,711

(22) Filed: Jun. 5, 2016

(65) Prior Publication Data
US 2016/0320320 A1  Nov. 3, 2016

Related U.S. Application Data

(63) Continuation-in-part of application No. 14/712,917, filed on May 15, 2015, now Pat. No. 9,874,531.
(Continued)

(51) Int. Cl.
*G01N 23/20* (2018.01)
*H01J 35/08* (2006.01)
(Continued)

(52) U.S. Cl.
CPC ..... *G01N 23/20075* (2013.01); *A61B 6/4007* (2013.01); *A61B 6/4291* (2013.01);
(Continued)

(58) Field of Classification Search
CPC ...... G01N 1/00; G01N 5/00; G01N 23/20075; A61B 6/482; A61B 6/4021; A61B 6/4064
See application file for complete search history.

(56) References Cited

U.S. PATENT DOCUMENTS

| 1,203,495 A | 10/1916 | Coolidge |
| 1,211,092 A | 1/1917 | Coolidge |

(Continued)

FOREIGN PATENT DOCUMENTS

| CN | 102124537 A | 7/2011 |
| CN | 102551761 A | 7/2012 |

(Continued)

OTHER PUBLICATIONS

"Diamond," Section 10.4.2 of Zorman et al., "Material Aspects of Micro-Nanoelectromechanical Systems," Chapter 10 of Springer Handbook of Nanotechnology, 2nd ed., Barat Bushan, ed. (Springer Science + Business Media, Inc., New York, 2007), pp. 312-314.
(Continued)

*Primary Examiner* — Don K Wong
(74) *Attorney, Agent, or Firm* — Knobbe, Martens, Olson & Bear, LLP

(57) ABSTRACT

This invention discloses a method and apparatus for x-ray techniques using structured x-ray illumination for examining material properties of an object. In particular, an object with one or more regions of interest (ROIs) having a particular shape, size, and pattern may be illuminated with an x-ray beam whose cross sectional beam profile corresponds to the shape, size and pattern of the ROIs, so that the x-rays of the beam primarily interact only with the ROIs. This allows a greater x-ray flux to be used, enhancing the signal from the ROI itself, while reducing unwanted signals from regions not in the ROI, improving signal-to-noise ratios and/or measurement throughput. This may be used with a number of x-ray measurement techniques, including x-ray fluorescence (XRF), x-ray diffraction (XRD), small angle x-ray scattering (SAXS), x-ray absorption fine-structure spectroscopy (XAFS), x-ray near edge absorption spectroscopy, and x-ray emission spectroscopy.

29 Claims, 20 Drawing Sheets

Related U.S. Application Data which is a continuation-in-part of application No. 14/700,137, filed on Apr. 29, 2015, now Pat. No. 9,719,947.

(60) Provisional application No. 61/993,792, filed on May 15, 2014, provisional application No. 61/993,811, filed on May 15, 2014, provisional application No. 62/343,594, filed on May 31, 2016, provisional application No. 62/171,377, filed on Jun. 5, 2015.

(51) Int. Cl.
*A61B 6/00* (2006.01)
*G01N 23/201* (2018.01)
*G21K 1/02* (2006.01)
*G01N 23/223* (2006.01)

(52) U.S. Cl.
CPC .............. *A61B 6/484* (2013.01); *A61B 6/508* (2013.01); *G01N 23/201* (2013.01); *G01N 23/223* (2013.01); *G21K 1/02* (2013.01); *H01J 35/08* (2013.01); *G21K 2207/005* (2013.01); *H01J 2235/086* (2013.01); *H01J 2235/1291* (2013.01)

(56) References Cited

U.S. PATENT DOCUMENTS

| | | |
|---|---|---|
| 1,215,116 A | 2/1917 | Coolidge |
| 1,328,495 A | 1/1920 | Coolidge |
| 1,355,126 A | 10/1920 | Coolidge |
| 1,790,073 A | 1/1931 | Pohl |
| 1,917,099 A | 7/1933 | Coolidge |
| 1,946,312 A | 2/1934 | Coolidge |
| 2,926,270 A | 2/1960 | Zunick |
| 3,795,832 A | 3/1974 | Holland |
| 4,165,472 A | 8/1979 | Wittry |
| 4,266,138 A | 5/1981 | Nelson et al. |
| 4,277,112 A | 7/1981 | Heshmat |
| 4,426,718 A | 1/1984 | Hayashi et al. |
| 4,523,327 A | 6/1985 | Eversole |
| 4,573,186 A | 2/1986 | Reinhold |
| 4,807,268 A | 2/1989 | Wittrey |
| 4,940,319 A | 7/1990 | Ueda et al. |
| 4,951,304 A | 8/1990 | Piestrup et al. |
| 4,972,449 A | 11/1990 | Upadhya et al. |
| 5,001,737 A | 3/1991 | Lewis et al. |
| 5,008,918 A | 4/1991 | Lee et al. |
| 5,132,997 A | 7/1992 | Kojima |
| 5,148,462 A | 9/1992 | Spitsyn et al. |
| 5,173,928 A | 12/1992 | Momose et al. |
| 5,249,216 A | 9/1993 | Ohsugi et al. |
| 5,276,724 A | 1/1994 | Kumasaka et al. |
| 5,602,899 A | 2/1997 | Larson |
| 5,604,782 A | 2/1997 | Cash, Jr. |
| 5,629,969 A | 5/1997 | Koshishiba |
| 5,657,365 A | 8/1997 | Yamamoto et al. |
| 5,682,415 A | 10/1997 | O'Hara |
| 5,715,291 A | 2/1998 | Momose |
| 5,729,583 A | 3/1998 | Tang et al. |
| 5,737,387 A | 4/1998 | Smither |
| 5,768,339 A | 6/1998 | O'Hara |
| 5,772,903 A | 6/1998 | Hirsch |
| 5,778,039 A | 7/1998 | Hossain |
| 5,812,629 A | 9/1998 | Clauser |
| 5,825,848 A | 10/1998 | Virshup et al. |
| 5,832,052 A | 11/1998 | Hirose et al. |
| 5,857,008 A | 1/1999 | Reinhold |
| 5,878,110 A | 3/1999 | Yamamoto et al. |
| 5,881,126 A | 3/1999 | Momose |
| 5,912,940 A | 6/1999 | O'Hara |
| 5,930,325 A | 7/1999 | Momose |
| 6,108,397 A | 8/2000 | Cash, Jr. |
| 6,108,398 A | 8/2000 | Mazor et al. |
| 6,125,167 A | 9/2000 | Morgan |
| 6,278,764 B1 | 8/2001 | Barbee, Jr. et al. |
| 6,307,916 B1 | 10/2001 | Rogers et al. |
| 6,359,964 B1 | 3/2002 | Kogan |
| 6,377,660 B1 | 4/2002 | Ukita et al. |
| 6,381,303 B1 | 4/2002 | Vu et al. |
| 6,389,100 B1 | 5/2002 | Verman et al. |
| 6,430,254 B2 | 8/2002 | Wilkins |
| 6,442,231 B1 | 8/2002 | O'Hara |
| 6,456,688 B1 | 9/2002 | Taguchi et al. |
| 6,463,123 B1 | 10/2002 | Korenev |
| 6,487,272 B1 | 11/2002 | Kutsuzawa |
| 6,504,902 B2 | 1/2003 | Iwasaki et al. |
| 6,507,388 B2 | 1/2003 | Burghoorn |
| 6,553,096 B1 | 4/2003 | Zhou et al. |
| 6,560,313 B1 | 5/2003 | Harding et al. |
| 6,560,315 B1 | 5/2003 | Price et al. |
| 6,707,883 B1 | 3/2004 | Tiearney et al. |
| 6,711,234 B1 | 3/2004 | Loxley et al. |
| 6,811,612 B2 | 11/2004 | Gruen et al. |
| 6,815,363 B2 | 11/2004 | Yun et al. |
| 6,829,327 B1 | 12/2004 | Chen |
| 6,847,699 B2 | 1/2005 | Rigali et al. |
| 6,850,598 B1 | 2/2005 | Fryda et al. |
| 6,870,172 B1 | 3/2005 | Mankos et al. |
| 6,885,503 B2 | 4/2005 | Yun et al. |
| 6,914,723 B2 | 7/2005 | Yun et al. |
| 6,917,472 B1 | 7/2005 | Yun et al. |
| 6,947,522 B2 | 9/2005 | Wilson et al. |
| 6,975,703 B2 | 12/2005 | Wilson et al. |
| 7,003,077 B2 | 2/2006 | Jen et al. |
| 7,006,596 B1 | 2/2006 | Janik |
| 7,015,467 B2 | 3/2006 | Maldonado et al. |
| 7,023,955 B2 | 4/2006 | Chen et al. |
| 7,057,187 B1 | 6/2006 | Yun et al. |
| 7,079,625 B2 | 7/2006 | Lenz |
| 7,095,822 B1 | 8/2006 | Yun |
| 7,110,503 B1 | 9/2006 | Kumakhov |
| 7,119,953 B2 | 10/2006 | Yun et al. |
| 7,130,375 B1 | 10/2006 | Yun et al. |
| 7,170,969 B1 | 1/2007 | Yun et al. |
| 7,180,979 B2 | 2/2007 | Momose |
| 7,180,981 B2 | 2/2007 | Wang |
| 7,183,547 B2 | 2/2007 | Yun et al. |
| 7,215,736 B1 | 5/2007 | Wang et al. |
| 7,215,741 B2 | 5/2007 | Ukita et al. |
| 7,218,700 B2 | 5/2007 | Huber et al. |
| 7,218,703 B2 | 5/2007 | Yada et al. |
| 7,221,731 B2 | 5/2007 | Yada et al. |
| 7,245,696 B2 | 7/2007 | Yun et al. |
| 7,268,945 B2 | 9/2007 | Yun et al. |
| 7,286,640 B2 | 10/2007 | Yun et al. |
| 7,297,959 B2 | 11/2007 | Yun et al. |
| 7,298,826 B2 | 11/2007 | Inazuru |
| 7,330,533 B2 | 2/2008 | Sampayon |
| 7,346,148 B2 | 3/2008 | Ukita |
| 7,346,204 B2 | 3/2008 | Ito |
| 7,349,525 B2 | 3/2008 | Morton |
| 7,359,487 B1 | 4/2008 | Newcome |
| 7,365,909 B2 | 4/2008 | Yun et al. |
| 7,365,918 B1 | 4/2008 | Yun et al. |
| 7,382,864 B2 | 6/2008 | Hebert et al. |
| 7,388,942 B2 | 6/2008 | Wang et al. |
| 7,394,890 B1 | 7/2008 | Wang et al. |
| 7,400,704 B1 | 7/2008 | Yun et al. |
| 7,406,151 B1 | 7/2008 | Yun |
| 7,412,024 B1 | 8/2008 | Yun et al. |
| 7,412,030 B1 | 8/2008 | O'Hara |
| 7,412,131 B2 | 8/2008 | Lee et al. |
| 7,414,787 B2 | 8/2008 | Yun et al. |
| 7,433,444 B2 | 10/2008 | Baumann |
| 7,440,532 B1 | 10/2008 | Baumann |
| 7,443,953 B1 | 10/2008 | Yun et al. |
| 7,453,981 B2 | 11/2008 | Baumann |
| 7,463,712 B2 | 12/2008 | Zhu et al. |
| 7,486,770 B2 | 2/2009 | Baumann |
| 7,492,871 B2 | 2/2009 | Popescu |
| 7,499,521 B2 | 3/2009 | Wang et al. |
| 7,515,684 B2 | 4/2009 | Gibson et al. |

(56) References Cited

U.S. PATENT DOCUMENTS

| | | |
|---|---|---|
| 7,522,698 B2 | 4/2009 | Popescu |
| 7,522,707 B2 | 4/2009 | Steinlage et al. |
| 7,522,708 B2 | 4/2009 | Heismann |
| 7,529,343 B2 | 5/2009 | Safai et al. |
| 7,532,704 B2 | 5/2009 | Hempel |
| 7,551,719 B2 | 6/2009 | Yokhin et al. |
| 7,551,722 B2 | 6/2009 | Ohshima et al. |
| 7,561,662 B2 | 7/2009 | Wang et al. |
| 7,564,941 B2 | 7/2009 | Baumann |
| 7,583,789 B1 | 9/2009 | Macdonald et al. |
| 7,601,399 B2 | 10/2009 | Barnola et al. |
| 7,639,786 B2 | 12/2009 | Baumann |
| 7,646,843 B2 | 1/2010 | Popescu et al. |
| 7,672,433 B2 | 3/2010 | Zhong et al. |
| 7,680,243 B2 | 3/2010 | Yokhin et al. |
| 7,787,588 B1 | 8/2010 | Yun et al. |
| 7,796,725 B1 | 9/2010 | Yun et al. |
| 7,796,726 B1 | 9/2010 | Gendreau et al. |
| 7,800,072 B2 | 9/2010 | Yun et al. |
| 7,809,113 B2 | 10/2010 | Aoki et al. |
| 7,813,475 B1 | 10/2010 | Wu et al. |
| 7,817,777 B2 | 10/2010 | Baumann et al. |
| 7,864,426 B2 | 1/2011 | Yun et al. |
| 7,864,922 B2 | 1/2011 | Kawabe |
| 7,873,146 B2 | 1/2011 | Okunuki et al. |
| 7,876,883 B2 | 1/2011 | O'Hara |
| 7,889,838 B2 | 2/2011 | David et al. |
| 7,889,844 B2 | 2/2011 | Okunuki et al. |
| 7,914,693 B2 | 3/2011 | Jeong et al. |
| 7,920,673 B2 | 4/2011 | Lanza et al. |
| 7,920,676 B2 | 4/2011 | Yun et al. |
| 7,924,973 B2 | 4/2011 | Kottler et al. |
| 7,929,667 B1 | 4/2011 | Zhuang et al. |
| 7,945,018 B2 | 5/2011 | Heismann |
| 7,949,092 B2 | 5/2011 | Brons et al. |
| 7,949,095 B2 | 5/2011 | Ning |
| 7,974,379 B1 | 7/2011 | Case et al. |
| 7,983,381 B2 | 7/2011 | David et al. |
| 7,991,120 B2 | 8/2011 | Okunuki et al. |
| 8,005,185 B2 | 8/2011 | Popescu |
| 8,009,796 B2 | 8/2011 | Popescu |
| 8,009,797 B2 | 8/2011 | Ouchi |
| 8,041,004 B2 | 10/2011 | David |
| 8,036,341 B2 | 11/2011 | Lee |
| 8,058,621 B2 | 11/2011 | Kommareddy et al. |
| 8,068,579 B1 | 11/2011 | Yun et al. |
| 8,073,099 B2 | 12/2011 | Niu et al. |
| 8,094,784 B2 | 1/2012 | Morton |
| 8,139,711 B2 | 3/2012 | Takahashi |
| 8,139,716 B2 | 3/2012 | Okunuki et al. |
| 8,184,771 B2 | 5/2012 | Murakoshi |
| 8,208,602 B2 | 6/2012 | Lee et al. |
| 8,208,603 B2 | 6/2012 | Sato |
| 8,233,587 B2 | 7/2012 | Sato |
| 8,243,879 B2 | 8/2012 | Itoh et al. |
| 8,243,884 B2 | 8/2012 | Rödhammer et al. |
| 8,280,000 B2 | 10/2012 | Takahashi |
| 8,306,183 B2 | 11/2012 | Koehler |
| 8,306,184 B2 | 11/2012 | Chang et al. |
| 8,351,569 B2 | 1/2013 | Baker |
| 8,351,570 B2 | 1/2013 | Nakamura |
| 8,353,628 B1 | 1/2013 | Yun et al. |
| 8,360,640 B2 | 1/2013 | Reinhold |
| 8,374,309 B2 | 2/2013 | Donath |
| 8,406,378 B2 | 3/2013 | Wang et al. |
| 8,416,920 B2 | 4/2013 | Okumura et al. |
| 8,422,633 B2 | 4/2013 | Lantz et al. |
| 8,451,975 B2 | 5/2013 | Tada |
| 8,422,637 B2 | 6/2013 | Okunuki et al. |
| 8,509,386 B2 | 8/2013 | Lee et al. |
| 8,520,803 B2 | 8/2013 | Behling |
| 8,526,575 B1 | 9/2013 | Yun et al. |
| 8,532,257 B2 | 9/2013 | Mukaide et al. |
| 8,553,843 B2 | 10/2013 | Drory |
| 8,559,594 B2 | 10/2013 | Ouchi |
| 8,559,597 B2 | 10/2013 | Chen et al. |
| 8,565,371 B2 | 10/2013 | Bredno |
| 8,576,983 B2 | 11/2013 | Baeumer |
| 8,591,108 B2 | 11/2013 | Tada |
| 8,602,648 B1 | 12/2013 | Jacobsen et al. |
| 8,632,247 B2 | 1/2014 | Ishii |
| 8,666,024 B2 | 3/2014 | Okunuki et al. |
| 8,666,025 B2 | 3/2014 | Klausz |
| 8,699,667 B2 | 4/2014 | Steinlage et al. |
| 8,735,844 B1 | 5/2014 | Khaykovich et al. |
| 8,737,565 B1 | 5/2014 | Lyon et al. |
| 8,744,048 B2 | 6/2014 | Lee et al. |
| 8,755,487 B2 | 6/2014 | Kaneko |
| 8,767,915 B2 | 7/2014 | Stutman |
| 8,767,916 B2 | 7/2014 | Hashimoto |
| 8,781,069 B2 | 7/2014 | Murakoshi |
| 8,824,629 B2 | 9/2014 | Ishii |
| 8,831,174 B2 | 9/2014 | Kohara |
| 8,831,175 B2 | 9/2014 | Silver et al. |
| 8,831,179 B2 | 9/2014 | Adler et al. |
| 8,855,265 B2 | 10/2014 | Engel |
| 8,861,682 B2 | 10/2014 | Okunuki et al. |
| 8,903,042 B2 | 12/2014 | Ishii |
| 8,908,824 B2 | 12/2014 | Kondoh |
| 8,995,622 B2 | 3/2015 | Adler et al. |
| 9,001,967 B2 | 4/2015 | Baturin |
| 9,008,278 B2 | 4/2015 | Lee et al. |
| 9,016,943 B2 | 4/2015 | Jacobsen et al. |
| 9,020,101 B2 | 4/2015 | Omote et al. |
| 9,063,055 B2 | 6/2015 | Ouchi |
| 9,129,715 B2 | 9/2015 | Adler et al. |
| 9,222,899 B2 | 12/2015 | Yamaguchi |
| 9,257,254 B2 | 2/2016 | Ogura et al. |
| 9,263,225 B2 | 2/2016 | Morton |
| 9,329,141 B2 | 5/2016 | Stutman |
| 9,357,975 B2 | 6/2016 | Baturin |
| 9,390,881 B2 * | 7/2016 | Yun .................. G21K 1/06 |
| 9,439,613 B2 | 9/2016 | Stutman |
| 9,448,190 B2 | 9/2016 | Yun et al. |
| 9,449,781 B2 | 9/2016 | Yun et al. |
| 9,494,534 B2 | 11/2016 | Baturin |
| 9,543,109 B2 | 1/2017 | Yun et al. |
| 9,564,284 B2 | 2/2017 | Gerzoskovitz |
| 9,570,265 B1 | 2/2017 | Yun et al. |
| 9,594,036 B2 | 3/2017 | Yun et al. |
| 9,632,040 B2 | 4/2017 | Stutman |
| 9,719,947 B2 | 8/2017 | Yun et al. |
| 9,757,081 B2 | 9/2017 | Proksa |
| 9,761,021 B2 | 9/2017 | Koehler |
| 9,823,203 B2 | 11/2017 | Yun et al. |
| 9,826,949 B2 | 11/2017 | Ning |
| 9,837,178 B2 | 12/2017 | Nagai |
| 9,842,414 B2 | 12/2017 | Koehler |
| 9,861,330 B2 | 1/2018 | Rossl |
| 9,874,531 B2 | 1/2018 | Yun et al. |
| 9,881,710 B2 | 1/2018 | Roessl |
| 9,916,655 B2 | 3/2018 | Sampanoni |
| 9,939,392 B2 | 4/2018 | Wen |
| 9,970,119 B2 | 5/2018 | Yokoyama |
| 10,014,148 B2 | 7/2018 | Tang et al. |
| 10,028,716 B2 | 7/2018 | Rossl |
| 10,045,753 B2 | 8/2018 | Teshima |
| 10,068,740 B2 | 9/2018 | Gupta |
| 10,074,451 B2 | 9/2018 | Kottler et al. |
| 10,085,701 B2 | 10/2018 | Hoshino |
| 10,141,081 B2 | 11/2018 | Preusche |
| 10,151,713 B2 | 12/2018 | Wu et al. |
| 10,153,062 B2 | 12/2018 | Gall et al. |
| 10,176,297 B2 | 1/2019 | Zerhusen et al. |
| 10,182,194 B2 | 1/2019 | Karim et al. |
| 2001/0006413 A1 | 7/2001 | Burghoorn |
| 2002/0085676 A1 | 7/2002 | Snyder |
| 2003/0142790 A1 | 1/2003 | Zhou et al. |
| 2003/0223536 A1 | 12/2003 | Yun et al. |
| 2004/0047446 A1 | 3/2004 | Platonov |
| 2004/0120463 A1 | 6/2004 | Wilson et al. |
| 2004/0140432 A1 | 7/2004 | Maldonado et al. |
| 2005/0074094 A1 | 4/2005 | Jen et al. |
| 2005/0123097 A1 | 6/2005 | Wang |

(56) References Cited

U.S. PATENT DOCUMENTS

| | | |
|---|---|---|
| 2005/0163284 A1 | 7/2005 | Inazuru |
| 2005/0282300 A1 | 12/2005 | Yun et al. |
| 2006/0045234 A1 | 3/2006 | Pelc et al. |
| 2006/0062350 A1 | 3/2006 | Yokhin |
| 2007/0030959 A1 | 2/2007 | Ritter |
| 2007/0071174 A1 | 3/2007 | Hebert et al. |
| 2007/0108387 A1 | 5/2007 | Yun et al. |
| 2007/0110217 A1 | 5/2007 | Ukita |
| 2007/0183563 A1 | 8/2007 | Baumann |
| 2007/0183579 A1 | 8/2007 | Baumann et al. |
| 2007/0189449 A1 | 8/2007 | Baumann |
| 2007/0248215 A1 | 10/2007 | Ohshima et al. |
| 2008/0084966 A1 | 4/2008 | Aoki et al. |
| 2008/0089484 A1 | 4/2008 | Reinhold |
| 2008/0094694 A1 | 4/2008 | Yun et al. |
| 2008/0116398 A1* | 5/2008 | Hara ............... B82Y 10/00 250/492.22 |
| 2008/0159707 A1 | 7/2008 | Lee et al. |
| 2008/0165355 A1 | 7/2008 | Yasui et al. |
| 2008/0170662 A1 | 7/2008 | Reinhold |
| 2008/0170668 A1 | 7/2008 | Kruit et al. |
| 2008/0181363 A1 | 7/2008 | Fenter et al. |
| 2008/0240344 A1 | 10/2008 | Reinhold |
| 2008/0273662 A1 | 11/2008 | Yun |
| 2009/0052619 A1 | 2/2009 | Endoh |
| 2009/0092227 A1 | 4/2009 | David |
| 2009/0154640 A1 | 6/2009 | Baumann et al. |
| 2009/0316860 A1 | 12/2009 | Okunuki et al. |
| 2010/0012845 A1 | 1/2010 | Baeumer et al. |
| 2010/0027739 A1 | 2/2010 | Lantz et al. |
| 2010/0040202 A1 | 2/2010 | Lee |
| 2010/0046702 A1 | 2/2010 | Chen et al. |
| 2010/0061508 A1 | 3/2010 | Takahashi |
| 2010/0091947 A1 | 4/2010 | Niu |
| 2010/0141151 A1 | 6/2010 | Reinhold |
| 2010/0246765 A1 | 9/2010 | Murakoshi |
| 2010/0260315 A1 | 10/2010 | Sato et al. |
| 2010/0272239 A1 | 10/2010 | Lantz et al. |
| 2010/0284513 A1 | 11/2010 | Kawabe |
| 2011/0026680 A1 | 2/2011 | Sato |
| 2011/0038455 A1 | 2/2011 | Silver et al. |
| 2011/0058655 A1 | 3/2011 | Okumura et al. |
| 2011/0064191 A1 | 3/2011 | Toth et al. |
| 2011/0085644 A1 | 4/2011 | Verman |
| 2011/0135066 A1 | 6/2011 | Behling |
| 2011/0142204 A1 | 6/2011 | Zou et al. |
| 2011/0235781 A1 | 9/2011 | Aoki et al. |
| 2011/0243302 A1 | 10/2011 | Murakoshi |
| 2011/0268252 A1 | 11/2011 | Ozawa et al. |
| 2012/0041679 A1 | 2/2012 | Stampanoni |
| 2012/0057669 A1 | 3/2012 | Vogtmeier et al. |
| 2012/0163547 A1 | 6/2012 | Lee et al. |
| 2012/0163554 A1 | 6/2012 | Tada |
| 2012/0224670 A1 | 9/2012 | Kiyohara et al. |
| 2012/0228475 A1 | 9/2012 | Pang et al. |
| 2012/0269323 A1 | 10/2012 | Adler et al. |
| 2012/0269324 A1 | 10/2012 | Adler |
| 2012/0269325 A1 | 10/2012 | Adler et al. |
| 2012/0269326 A1 | 10/2012 | Adler et al. |
| 2012/0294420 A1 | 11/2012 | Nagai |
| 2013/0011040 A1 | 1/2013 | Kido et al. |
| 2013/0032727 A1 | 2/2013 | Kondoe |
| 2013/0039460 A1 | 2/2013 | Levy |
| 2013/0108012 A1 | 5/2013 | Sato |
| 2013/0108022 A1 | 5/2013 | Kugland et al. |
| 2013/0195246 A1 | 8/2013 | Tamura et al. |
| 2013/0223594 A1 | 8/2013 | Sprong et al. |
| 2013/0259207 A1 | 10/2013 | Omote et al. |
| 2013/0279651 A1 | 10/2013 | Yokoyama |
| 2013/0308112 A1 | 11/2013 | Clube et al. |
| 2013/0308754 A1 | 11/2013 | Yamazaki et al. |
| 2014/0023973 A1 | 1/2014 | Marconi et al. |
| 2014/0037052 A1 | 2/2014 | Adler |
| 2014/0064445 A1 | 3/2014 | Adler |
| 2014/0072104 A1 | 3/2014 | Jacobsen et al. |
| 2014/0079188 A1 | 3/2014 | Hesselink et al. |
| 2014/0105363 A1 | 4/2014 | Chen et al. |
| 2014/0146945 A1 | 5/2014 | Fredenberg et al. |
| 2014/0153692 A1 | 6/2014 | Larkin et al. |
| 2014/0177800 A1 | 6/2014 | Sato et al. |
| 2014/0185778 A1 | 7/2014 | Lee et al. |
| 2014/0205057 A1 | 7/2014 | Koehler et al. |
| 2014/0211919 A1 | 7/2014 | Ogura et al. |
| 2014/0226785 A1 | 8/2014 | Stutman et al. |
| 2014/0241493 A1 | 8/2014 | Yokoyama |
| 2014/0270060 A1 | 9/2014 | Date et al. |
| 2014/0369469 A1 | 12/2014 | Ogura et al. |
| 2015/0030126 A1 | 1/2015 | Radicke |
| 2015/0030127 A1 | 1/2015 | Aoki et al. |
| 2015/0043713 A1 | 2/2015 | Chen |
| 2015/0049860 A1 | 2/2015 | Das |
| 2015/0055743 A1 | 2/2015 | Vedantham et al. |
| 2015/0055745 A1 | 2/2015 | Holzner et al. |
| 2015/0092924 A1 | 4/2015 | Yun et al. |
| 2015/0110252 A1 | 4/2015 | Yun et al. |
| 2015/0117599 A1 | 4/2015 | Yun et al. |
| 2015/0194287 A1 | 7/2015 | Yun et al. |
| 2015/0243397 A1 | 8/2015 | Yun et al. |
| 2015/0247811 A1 | 9/2015 | Yun et al. |
| 2015/0260663 A1 | 9/2015 | Yun et al. |
| 2015/0357069 A1 | 12/2015 | Yun et al. |
| 2016/0064175 A1 | 3/2016 | Yun et al. |
| 2016/0066870 A1 | 3/2016 | Yun et al. |
| 2016/0106387 A1 | 4/2016 | Kahn et al. |
| 2016/0178540 A1 | 6/2016 | Yun et al. |
| 2016/0268094 A1 | 9/2016 | Yun et al. |
| 2016/0320320 A1 | 11/2016 | Yun et al. |
| 2016/0351370 A1 | 12/2016 | Yun et al. |
| 2017/0047191 A1 | 2/2017 | Yun et al. |
| 2017/0052128 A1 | 2/2017 | Yun et al. |
| 2017/0162288 A1 | 6/2017 | Yun et al. |
| 2017/0162359 A1 | 6/2017 | Tang et al. |
| 2017/0227476 A1 | 8/2017 | Zhang et al. |
| 2017/0234811 A1 | 8/2017 | Zhang et al. |
| 2017/0261442 A1 | 9/2017 | Yun et al. |
| 2017/0336334 A1 | 11/2017 | Yun et al. |
| 2018/0144901 A1 | 5/2018 | Yun et al. |
| 2018/0261352 A1 | 9/2018 | Matsuyama et al. |
| 2018/0306734 A1 | 10/2018 | Morimoto et al. |
| 2018/0323032 A1 | 11/2018 | Strelec et al. |
| 2018/0344276 A1 | 12/2018 | DeFreitas et al. |
| 2018/0348151 A1 | 12/2018 | Kasper et al. |
| 2018/0356355 A1 | 12/2018 | Momose et al. |
| 2019/0017942 A1 | 1/2019 | Filevich |
| 2019/0017946 A1 | 1/2019 | Wack et al. |
| 2019/0018824 A1 | 1/2019 | Zarkadas |
| 2019/0019647 A1 | 1/2019 | Lee et al. |
| 2019/0027265 A1 | 1/2019 | Dey et al. |
| 2019/0043689 A1 | 2/2019 | Camus |

FOREIGN PATENT DOCUMENTS

| | | |
|---|---|---|
| EP | 0432568 | 6/1991 |
| EP | 0751533 | 1/1997 |
| EP | 1028451 | 8/2000 |
| FR | 2548447 | 1/1985 |
| JP | H06-188092 | 7/1994 |
| JP | H07-056000 | 3/1995 |
| JP | H08-184572 | 7/1996 |
| JP | 2000-306533 | 11/2000 |
| JP | 2003-288853 | 10/2003 |
| JP | 2004-089445 | 3/2004 |
| JP | 2007-218683 | 8/2007 |
| JP | 2007-265981 | 10/2007 |
| JP | 2007-311185 | 11/2007 |
| JP | 2008-200359 | 4/2008 |
| JP | 2008-145111 | 6/2008 |
| JP | 2008-197495 | 8/2008 |
| JP | 2009-195349 | 3/2009 |
| JP | 2009-212058 | 9/2009 |
| JP | 2010-236986 | 10/2010 |
| JP | 2011-029072 | 2/2011 |
| JP | 2011-218147 | 11/2011 |
| JP | 2012-032387 | 2/2012 |

(56) References Cited

FOREIGN PATENT DOCUMENTS

| | | |
|---|---|---|
| JP | 2012-187341 | 10/2012 |
| JP | 2012-254294 | 12/2012 |
| JP | 2013-508683 | 3/2013 |
| JP | 2013-157269 | 8/2013 |
| JP | 2013-160637 | 8/2013 |
| JP | 2013-239317 | 11/2013 |
| JP | 2015-002074 | 1/2015 |
| JP | 2015-047306 | 3/2015 |
| JP | 2015-077289 | 4/2015 |
| WO | WO1995/006952 | 3/1995 |
| WO | WO 1998/011592 | 3/1998 |
| WO | WO 2002/039792 | 5/2002 |
| WO | WO 2003/081631 | 10/2003 |
| WO | WO 2005/109969 | 11/2005 |
| WO | WO 2006/096052 | 9/2006 |
| WO | WO 2007/1125833 | 11/2007 |
| WO | WO 2009/098027 | 8/2009 |
| WO | WO 2009/1104560 | 8/2009 |
| WO | WO 2011/032572 | 3/2011 |
| WO | WO 2012/032950 | 3/2012 |
| WO | WO 2013/004574 | 1/2013 |
| WO | WO 2013/111050 | 8/2013 |
| WO | WO 2013/118593 | 8/2013 |
| WO | WO 2013/160153 | 10/2013 |
| WO | WO 2013/168468 | 11/2013 |
| WO | WO 2014/054497 | 4/2014 |
| WO | WO 2015/016019 | 2/2015 |
| WO | WO 2015/034791 | 3/2015 |
| WO | WO 2015/066333 | 5/2015 |
| WO | WO 2015/084466 | 6/2015 |
| WO | WO 2015/168473 | 11/2015 |
| WO | WO 2015/176023 | 11/2015 |
| WO | WO 2015/187219 | 12/2015 |
| WO | WO 2016/187623 | 11/2016 |
| WO | WO 2017/031740 | 3/2017 |
| WO | WO 2017/204850 | 11/2017 |
| WO | WO 2017/213996 | 12/2017 |
| WO | WO 2018/175570 | 9/2018 |

OTHER PUBLICATIONS

"Element Six CVD Diamond Handbook" (Element Six, Luxembourg, 2015).
"High performance benchtop EDXRF spectrometer with Windows® software," published by: Rigaku Corp., Tokyo, Japan; 2017.
"Monochromatic Doubly Curved Crystal Optics," published by: X-Ray Optical Systems, Inc. (XOS), East Greenbush, NY; 2017.
"Optics and Detectors," Section 4 of XS-Ray Data Booklet, 3rd Ed., A.C. Thompson ed. (Lawrence Berkeley Nat'l Lab, Berkeley, CA, 2009).
"Properties of Solids," Ch. 12 of CRC Handbook of Chemistry and Physics, 90th ed., Devid R. Lide & W.M. "Mickey" Haynes, eds. (CRC Press, Boca Raton, FL, 2009), pp. 12-41-12-46; 12-203-12-212.
"Science and Technology of Future Light Sources", Arthur L. Robinson (LBNL) and Brad Plummer (SLAG), eds. Report Nos. ANL-08/39 / BNL-81895-2008 / LBNL-1090E-2009 / SLAC-R-917 (Lawrence Berkeley Nal'l Lab, Berkeley, CA, Dec. 2008).
"Series 5000 Packaged X-ray Tubes," Product Technical Data Sheet DS006 Rev. G, X-Ray Technologies Inc. (Oxford Insstruments), Scotts Valley, CA (no date).
"Toward Control of Matter: Energy Science Needs for a New Class of X-Ray Light Sources" (Lawrence Berkeley Nal'l Lab, Berkeley, CA, Sep. 2008).
"X-ray Optics for BES Light Source Facilities," Report of the Basic Energy Sciences Workshop on X-ray Optics for BES Light Source Facilities, D. Mills & H. Padmore, Co-Chairs, (U.S. Dept. of Energy, Office of Science, Potomac, MD, Mar. 2013).
Abullian et al., "Quantitative determination of the lateral density and intermolecular correlation between proteins anchored on the membrane surfaces using grazing incidence small-angle X-ray scattering and grazing incidence X-ray fluorescence," Nov. 28, 2012, The Journal of Chemical Physics, vol. 137, pp. 204907-1 to 204907-8.
Adachi et al., "Development of the 17-inch Direct-Conversion Dynamic Flat-panel X-ray Detector (FPD)," Digital R/F (Shimadzu Corp., 2 pages (no date, published—2004 with product release).
Aharonovich et al., "Diamond Nanophotonics," Adv. Op. Mat'ls vol. 2, Issue 10 (2014).
Als-Nielsen et al., "Phase contrast imaging" Sect. 9.3 of Ch. 9 of "Elements of Modern X-ray Physics, Second Edition" , (John Wiley & Sons Ltd, Chichester, West Sussex, UK, 2011), pp. 318-329.
Als-Nielsen et al., "Photoelectric Absorption," Ch. 7 of "Elements of Modern X-ray Physics, Second Edition," (John Wiley & Sons Ltd, Chichester, West Sussex, UK, 2011).
Als-Nielsen et al., "Refraction and reflection from interfaces," Ch. 3 of "Elements of Modern X-ray Physics, Second Edition," (John Wiley & Sons Ltd., Chichester, West Sussex, UK, 2011), pp. 69-112.
Als-Nielsen et al., "X-rays and their interaction with matter", and "Sources", Ch. 1 & 2 of "Elements of Modern X-ray Physics, Second Edition" (John Wiley & Sons Ltd, Chichester, West Sussex, UK, 2011).
Altapova et al., "Phase contrast laminography based on Talbot interferometry," Opt. Express, vol. 20, No. 6, (2012) pp. 6496-6508.
Ando et al., "Smooth and high-rate reactive ion etching of diamond," Diamond and Related Materials, vol. 11, (2002) pp. 824-827.
Arfelli et al., "Mammography with Synchrotron Radiation: Phase-Detection Techniques," Radiology vol. 215, (2000), pp. 286-293.
Arndt et al., Focusing Mirrors for Use with Microfocus X-ray Tubes, 1998, Journal of Applied Crystallography, vol. 31, pp. 733-741.
Balaic et al., "X-ray optics of tapered capillaries," Appl. Opt. vol. 34 (Nov. 1995) pp. 7263-7272.
Baltes et al., "Coherent and incoherent grating reconstruction," J. Opt. Soc. Am. A vol. 3(8), (1986), pp. 1268-1275.
Barbee Jr., "Multilayers for x-ray optics," Opt. Eng. vol. 25 (Aug. 1986) pp. 898-915.
Baron et al., "A compact optical design for Bragg reflections near backscattering," J. Synchrotron Rad., vol. 8 (2001), pp. 1127-1130.
Bech, "In-vivo dark-field and phase-contrast x-ray imaging," Scientific Reports 3, (2013), Article No. 03209.
Bech, "X-ray imaging with a grating interferometer," University of Copenhagan PhD. Thesis, (May 1, 2009).
Bergamin et al., "Measuring small lattice distortions in Si-crystals by phase-contrast x-ray topography," J. Phys. D: Appl. Phys. vol. 33 (Dec. 31, 2000) pp. 2678-2682.
Bernstorff, "Grazing Incidence Small Angle X-ray Scattering (GISAXS)," Presentation at Advanced School on Synchrotron and Free Electron Laser Sources and their Multidisciplinary Applications, Apr. 2008, Trieste, Italy.
Bilderback et al., "Single Capillaries," Ch. 29 of "Handbook of Optics vol. III, 2nd Ed." (McGraw Hill, New York, 2001).
Birkholz, "Chapter 4: Grazing Incidence Configurations," Thin Film Analysis by X-ray Scattering (Wiley-VCH Verlag GmbH & Co. KGaA, Weinheim, Germany, 2006).
Bjeoumikhov et al., "A modular system for XRF and XRD applications consisting of a microfocus X-ray source and different capillary optics," X-ray Spectrometry, vol. 33 (2004), pp. 312-316.
Bjeoumikhov et al., "Capillary Optics for X-Rays," Ch. 18 of "Modern Developments in X-Ray and Neutron Optics," A. Erko et al., eds. (Springer, Berlin, Germany, 2008), pp. 287-306.
Canberra Model S-5005 WinAxil X-Ray Analysis Software, published by: Canberra Eurisys Benelux N.V./S.A.,Zellik, Belgium; Jun. 2004.
Cerrina, "The Schwarzschild Objective," Ch. 27 of "Handbook of Optics vol. III, 2nd Ed." (McGraw Hill, New York, 2001).
Chen et al., "Advance in detection of low sulfur content by wavelength dispersive XRF," Proceedings of the Annual ISA Analysis Division Symposium (2002).
Chen et al., "Doubly curved crystal (DCC) X-ray optics and applications," Powder Diffraction, vol. 17(2) (2002), pp. 99-103.

(56) References Cited

OTHER PUBLICATIONS

Chen et al., "Guiding and focusing neutron beams using capillary optics," Nature vol. 357 (Jun. 4, 1992), pp. 391-393.
Chervenak et al., "Experimental thick-target bremsstrahlung spectra from electrons in the range 10 to 30 keV", Phys. Rev. A vol. 12 (1975), pp. 26-33.
Coan et al., "In vivo x-ray phase contrast analyzer-based imaging for longitudinal osteoarthritis studies in guinea pigs," Phys. Med. Biol. vol. 55(24) (2010), pp. 7649-7662.
Cockcroft et al., "Chapter 2: Experimental Setups," Powder Diffraction: Theory and Practice, R.E. Dinnebier and S.J.L. Billinge, eds (Royal Society of Chemistry Publishing, London, UK, 2008).
Cohen et al., "Tunable laboratory extended x-ray absorption fine structure system," Rev. Sci. Instr. vol. 51, No. 3, Mar. 1980, pp. 273-277.
Cong et al., "Fourier transform-based iterative method for differential phase-contrast computed tomography", Opt. Lett. vol. 37 (2012), pp. 1784-1786.
Cornaby et al., "Advances in X-ray Microfocusing with Monocapillary Optics at CHESS," CHESS News Magazine (2009), pp. 63-66.
Cornaby et al., "Design of Single-Bounce Monocapillary X-ray Optics," Advances in X-ray Analysis: Proceedings of the 55th Annual Conference on Applications of X-ray Analysis, vol. 50, (International Centre for Diffraction Data (ICDD), 2007), pp. 194-200.
Cornaby, "The Handbook of X-ray Single Bounce Monocapillary Optics, Including Optical Design and Synchrotron Applications" (PhD Dissertation, Cornell University, Ithaca, NY, May 2008).
David et al., "Fabrication of diffraction gratings for hard x-ray phase contrast imaging," Microelectron. Eng. vol. 84, (2007), pp. 1172-1177.
David et al., "Hard X-ray phase imaging and tomography using a grating interferometer," Spectrochimica Acta Part B vol. 62 (2007) pp. 626-630.
Davis et al., "Bridging the Micro-to-Macro Gap: A New Application for Micro X-Ray Fluorescence," Microsc Microanal., vol. 17(3) (Jun. 2011), pp. 410-417.
Diaz et al., "Monte Carlo Simulation of Scatter Field for Calculation of Contrast of Discs in Synthetic CDMAM Images," in: Digital Mammography, Proceedings 10th International Workshop IWDM 2010 (Springer Verlag, Berlin Heidelberg), (2010), pp. 628- 635 (9 pages). Jun. 18, 2010.
Ding et al., "Reactive Ion Etching of CVD Diamond Films for MEMS Applications," Micromachining and Microfabrication, Proc. SPIE vol. 4230 (2000), pp. 224-230.
Dobrovinskaya et al., "Thermal Properties," Sect. 2.1.5 of "Sapphire: Material, Manufacturing Applications" (Springer Science + Business Media, New York, 2009).
Erko et al., "X-ray Optics," Ch. 3 of "Handbook of Practical X-Ray Fluorescence Analysis," B. Beckhoff et al., eds. (Springer, Berlin, Germany, 2006), pp. 85-198.
Falcone et al., "New directions in X-ray microscopy," Contemporary Physics, vol. 52, No. 4, (Jul.-Aug. 2010), pp. 293-318.
Fernández-Ruiz, "TXRF Spectrometry as a Powerful Tool for the Study of Metallic Traces in Biological Systems," Development in Analytical Chemistry, vol. 1 (2014), pp. 1-14.
Freund, "Mirrors for Synchrotron Beamlines," Ch. 26 of "Handbook of Optics vol. III, 2nd Ed." (McGraw Hill, New York, 2001).
Ge et al., "Investigation of the partially coherent effects in a 2D Talbot interferometer," Anal. Bioanal. Chem. vol. 401, (2011), pp. 865-870. Apr. 29, 2011 pub Jun. 14, 2011.
Gibson et al., "Polycapillary Optics: An Enabling Technology for New Applications," Advances in X-ray Analysis, vol. 45 (2002), pp. 286-297.
Gonzales et al., "Angular Distribution of Bremsstrahlung Produced by 10-Kev and 20 Kev Electrons Incident on a Thick Au Target", in Application of Accelerators in Research and Industry, AIP Conf. Proc. 1221 (2013), pp. 114-117.

Gonzales et al., "Angular distribution of thick-target bremsstrahlung produced by electrons with initial energies ranging from 10 to 20 keV incident on Ag", Phys. Rev. A vol. 84 (2011): 052726.
Guttmann et al., "Ellipsoidal capillary as condenser for the Besssy full-field x-ray microscope," J. Phys. Conf. Ser. vol. 186 (2009): 012064.
Harasse et al., "Iterative reconstruction in x-ray computed laminography from differential phase measurements", Opt. Express. vol. 19 (2011), pp. 16560-16573.
Harasse et al., "X-ray Phase Laminography with a Grating Interferometer using Iterative Reconstruction", in International Workshop on X-ray and Neutron Phase Imaging with Gratings, AIP Conf. Proc. vol. 1466, (2012), pp. 163-168.
Harasse et al., "X-ray Phase Laminography with Talbot Interferometer", in Developments in X-Ray Tomography VII, Proc. SPIE vol. 7804 (2010), 780411.
Hasse et al., "New developments in laboratory-based x-ray sources and optics," Adv. In Laboratory-based X-Ray Sources, Optics, and Applications VI, ed. A.M. Khounsary, Proc. SPIE vol. 10387, 103870B-1 (2017).
Hemraj-Benny et al., "Near-Edge X-ray Absorption Fine Structure Spectroscopy as a Tool for Investigating Nanomaterials," Small, vol. 2(1), (2006), pp. 26-35.
Henke et al., "X-ray interactions: photoabsorption, scattering, transmission, and reflection at E=50–30000 eV, Z=1–92," Atomic Data and Nuclear Data Tables, vol. 54 (No. 2) (Jul. 1993), pp. 181-342.
Honma et al., Full-automatic XAFS Measurement System of the Engineering Science Research II beamline BL14B2 at Spring-8, 2011, AIP Conference Proceedings 1234, pp. 13-16.
Howard et al., "High-Definition X-ray Fluorescence Elemental Mapping of Paintings," Anal. Chem., 2012, vol. 84(7), pp. 3278-3286.
Howells, "Gratings and Monochromators in the VUV and Soft X-Ray Spectral Region," Ch. 21 of Handbook of Optics vol. III, 2nd Ed. (McGraw Hill, New York, 2001).
Howells, "Mirrors for Synchrotron-Radiation Beamlines," Publication LBL-34750 (Lawrence Berkeley Laboratory, Berkeley, CA, Sep. 1993).
Hrdý et al, "Diffractive-Refractive Optics: X-ray Crystal Monochromators with Profiled Diffracting Surfaces," Ch. 20 of "Modern Developments in X-Ray and Neutron Optics," A. Erko et al., eds. (Springer, Berlin Heidelberg New York, 2008).
Hwang et al, "New etching process for device fabrication using diamond," Diamond & Related Materials, vol. 13 (2004) pp. 2207-2210.
Ide-Ektessabi et al., "The role of trace metallic elements in neurodegenerative disorders: quantitative analysis using XRF and XANES spectroscopy," Anal. Sci., vol. 21(7) (Jul. 2005), pp. 885-892.
Ihsan et al., "A microfocus X-ray tube based on a microstructured X-ray target", Nuclear Instruments and Methods in Physics Research B vol. 267 (2009) pp. 3566-3573.
Ishisaka et al., "A New Method of Analyzing Edge Effect in Phase Contrast Imaging with Incoherent X-rays," Optical Review, vol. 7, No. 6, (2000), pp. 566-572.
Ito et al., "A Stable In-Laboratory EXAFS Measurement System," Jap. J. Appl. Phys., vol. 22, No. 2, Feb. 1, 1983, pp. 357-360.
Itoh et al., "Two-dimensional grating-based X-ray phase-contrast imaging using Fourier transform phase retrieval," Op. Express, vol. 19, No. 4 (2011) pp. 3339-3346.
Janssens et al, "Recent trends in quantitative aspects of microscopic X-ray fluorescence analysis," TrAC Trends in Analytical Chemistry 29.6 (Jun. 2010): 464-478.
Jiang et al., "X-Ray Phase-Contrast Imaging with Three 2D Gratings," Int. J. Biomed. Imaging, (2008), 827152, 8 pages.
Joy, "Astronomical X-ray Optics," Ch. 28 of "Handbook of Optics vol. III, 2nd Ed.," (McGraw Hill, New York, 2001).
Keyrilainen et al., "Phase contrast X-ray imaging of breast," Acta Radiologica, vol. 51 (8), (2010), pp. 866-884. Jan. 18, 2010 pub Jun. 15, 2010.
Kidalov et al., "Thermal Conductivity of Diamond Composites," Materials, vol. 2 (2009) pp. 2467-2495.

(56) References Cited

OTHER PUBLICATIONS

Kido et al., "Bone Cartilage Imaging with X-ray Interferometry using a Practical X-ray Tube", in Medical Imaging 2010: Physics of Medical Imaging, Proc. SPIE vol. 7622 (2010), 762240.
Kim, "Talbot images of wavelength-scale amplitude gratings," Opt. Express vol. 20(5), (2012), pp. 4904-4920.
Kirkpatrick et al., "Formation of Optical Images by X-Rays", J. Opt. Soc. Am. vol. 38(9) (1948), pp. 766-774.
Kirz, "Phase zone plates for x rays and the extreme uv," J. Op. Soc. Am. vol. 64 (Mar. 1974), pp. 301-309.
Kirz et al., "The History and Future of X-ray Microscopy", J. Physics: Conden. Series vol. 186 (2009): 012001.
Kiyohara et al., "Development of the Talbot-Lau Interferometry System Available for Clinical Use", in International Workshop on X-ray and Neutron Phase Imaging with Gratings, AIP Cong. Proc. vol. 1466, (2012), pp. 97-102.
Klockenkämper et al., "7.1 Instrumental Developments" and "7.3 Future Prospects by Combinations," from Chapter 7 of Total Reflection X-ray Fluorescence Analysis and Related Methods 2nd Ed. (J. Wiley and Sons, Hoboken, NJ, 2015).
Klockenkämper et al., "Chapter 3: Instrumentation for TXRF and GI-XRF," Total Reflection X-ray Fluorescence Analysis and Related Methods 2nd Ed. (J. Wiley and Sons, Hoboken, NJ, 2015).
Kottler et al., "A two-directional approach for grating based differential phase contrast imaging using hard x-rays," Opt. Express vol. 15(3), (2007), pp. 1175-1181.
Kottler et al., "Dual energy phase contrast x-ray imaging with Talbot-Lau interferometer," J. Appl. Phys. vol. 108(11), (2010), 114906. Jul. 7, 2010 pub Dec. 7, 2010.
Kumakhov et al., "Multiple reflection from surface X-ray optics," Physics Reports, vol. 191(5), (1990), pp. 289-350.
Kumakhov, "X-ray Capillary Optics. History of Development and Present Status" in Kumakhov Optics and Application, Proc. SPIE 4155 (2000), pp. 2-12.
Kuwabara et al., "Hard-X-ray Phase-Difference Microscopy with a Low-Brilliance Laboratory X-ray Source", Appl. Phys. Express vol. 4 (2011) 062502.
Kuznetsov, "X-Ray Optics Calculator," Institute of Microelectronics Technology and High Purity Materials, Russian Academy of Sciences (IMT RAS), Chernogolovka, Russia (6 pages submitted); 2016.
Lagomarsino et al., "Reflective Optical Arrays," Ch. 19 of "Modern Developments in X-Ray and Neutron Optics," A. Erko et al. eds. (Springer, Berlin, Germany, 2008), pp. 307-317.
Lai, "X-Ray Microfocusing Optics," Slide Presentation from Argonne National Laboratory, 71 slides, Cheiron Summer School 2007.
Langhoff et al., "X-ray Sources," Ch. 2 of "Handbook of Practical X-Ray Fluorescence Analysis," B. Beckhoff et al., eds. (Springer, Berlin Heidelberg New York, 2006), pp. 33-82.
Lechner et al., "Silicon drift detecors for high count rate X-ray spectroscopy at room temperature," Nuclear Instruments and Methods, vol. 458A (2001), pp. 281-287.
Leenaers et al., "Application of Glancing Incidence X-ray Analysis," 1997, X-ray Spectrometry, vol. 26, pp. 115-121.
Lengeler et al., "Refractive X-ray Optics," Ch. 20 of "Handbook of Optics vol. III, 2nd Ed." (McGraw Hill, New York, 2001.
Li et al., "Source-optic-crystal optimisation for compact monochromatic imaging," Proc. SPIE 5537 (2004), pp. 105-114.
Lohmann et al., "An interferometer based on the Talbot effect," Optics Communications vol. 2 (1971), pp. 413-415.
MacDonald et al., "An Introduction to X-ray and Neutron Optics," Ch. 19 of "Handbook of Optics vol. III, 2nd Ed." (McGraw Hill, New York, 2001).
MacDonald et al., "Polycapillary and Multichannel Plate X-Ray Optics," Ch. 30 of "Handbook of Optics vol. III, 2nd Ed.," (McGraw Hill, New York, 2001).
MacDonald et al., "Polycapillary X-ray Optics for Microdiffraction," J. Appl. Cryst., vol. 32 (1999) pp. 160-167.
MacDonald, "Focusing Polycapillary Optics and Their Applications," X-Ray Optics and Instrumentation, vol. 2010, (Oct. 2010): 867049.
Maj et al., "Etching methods for improving surface imperfections of diamonds used for x-ray monochromators," Adv. X-ray Anal., vol. 48 (2005), pp. 176-182.
Malgrange, "X-ray Optics for Synchrotron Radiation," ACTA Physica Polinica A, vol. 82(1) (1992) pp. 13-32.
Masuda et al., "Fabrication of Through-Hole Diamond Membranes by Plasma Etching Using Anodic Porous Alumina Mask," Electrochemical and Solid-State Letters, vol. 4(11) (2001) pp. G101-G103.
Matsushita, "Mirrors and Multilayers," Slide Presentation from Photon Factor, Tsukuba, Japan, 65 slides, (Cheiron School 2009, Sprint-8, Japan, Nov. 2009).
Matsushita, "X-ray monochromators," Slide Presentation from Photon Factory, Tsukuba, Japan, 70 slides, (Cheiron School 2009, Spring-8, Japan, Nov. 2009).
Matsuyama et al., "Wavefront measurement for a hard-X-ray nanobeam using single-grating interferometry", Opt Express vol. 20 (2012), pp. 24977-24986.
Miao et al., "Motionless phase stepping in X-ray phase contrast imaging with a compact source," Proceedings of the National Academy of Sciences, vol. 110(48), (2013), pp. 19268-19272.
Michette, "Zone and Phase Plates, Bragg-Fresnel Optics," Ch. 23 of "Handbook of Optics vol. III, 2nd Ed.," (McGraw Hill, New York, 2001).
Mizutani et al., X-ray microscopy for neural circuit reconstruction in 9th International Conference on X-Ray Microscopy, J. Phys: Conf. Ser. 186 (2009) 012092.
Modregger et al., "Grating-Based X-ray Phase Contrast Imaging," Ch. 3 of Emerging Imaging Technologies in Medicine, M. Anastasio & P. La Riviere, ed., CRC Press, Boca Raton, FL, (2012), pp. 43-56.
Momose et al., "Biomedical Imaging by Talbot-Type X-Ray Phase Tomography" in Developments in X-Ray Tomography V, Proc. SPIE vol. 6318 (2006) 63180T.
Momose et al., "Grating-Based X-ray Phase Imaging Using Multiline X-ray Source", Jpn. J. Appl. Phys. vol. 48 (2009), 076512.
Momose et al., "Phase Tomography by X-ray Talbot Interferometry for Biological Imaging" Jpn. J. Appl. Phys. vol. 45 2006 pp. 5254-5262.
Momose et al., "Phase Tomography Using X-ray Talbot Interferometer", in Synchrotron Radiation Instrumentation: Ninth International Conference, AIP Conf. Proc. vol. 879 (2007), pp. 1365-1368.
Momose et al., "Phase-Contrast X-Ray Imaging Using an X-Ray Interferometer for Biological Imaging", Analytical Sciences vol. 17 Supplement (2001), pp. i527-i530.
Momose et al., "Sensitivity of X-ray Phase Imaging Based on Talbot Interferometry", Jpn. J. Appl. Phys. vol. 47 (2008), pp. 8077-8080.
Momose et al., "X-ray Phase Measurements with Talbot Interferometry and Its Applications", in International Conference on Advanced Phase Measurement Methods in Optics and Imaging, AIP Conf. Proc. vol. 1236 (2010), pp. 195-199.
Momose et al., "X-ray Phase Imaging—From Static Observation to Dynamic Observation-", in International Workshop on X-ray and Neutron Phase Imaging with Gratings AIP Conf. Proc. vol. 1466, (2012), pp. 67-77.
Momose et al., "X-ray Phase Imaging Using Lau Effect", Appl. Phys. Express vol. 4 (2011) 066603.
Momose et al., "X-Ray Phase Imaging with Talbot Interferometry", in "Biomedical Mathematics: Promising Directions in Imaging, Therapy Planning, and Inverse Problems", Y. Censor, M. Jiang & G.Wang, eds. (Medical Physics Publishing, Madison, WI, USA, 2010), pp. 281-320.
Momose et al., "X-ray phase tomography with a Talbot interferometer in combination with an X-ray imaging microscope", in 9th International Conference on X-Ray Microscopy, J. Phys: Conf. Ser. 186 (2009) 012044.
Momose et al., "X-ray Talbot Interferometry with Capillary Plates", Jpn. J. Appl. Phys. vol. 45 (2006), pp. 314-316.
Momose et al., "Four-dimensional X-ray phase tomography with Talbot interferometry and white synchrotron radiation: dynamic observation of a living worm", Opt. Express vol. 19 (2011), pp. 8423-8432.

(56) References Cited

OTHER PUBLICATIONS

Momose et al., "High-speed X-ray phase imaging and X-ray phase tomography with Talbot interferometer and white synchrotron radiation", Opt. Express vol. 17 (2009), pp. 12540-12545.
Momose et al., "Phase Imaging with an X-ray Talbot Interferometer", Advances in X-ray Analysis vol. 49(3) (2006), pp. 21-30.
Momose et al.,"Demonstration of X-Ray Talbot Interferometry", Jpn. J. Appl. Phys. vol. 42 (2003), pp. L866-L868.
Momose et al.,"Phase Tomography Using an X-ray Talbot Interferometer", in Developments in X-Ray Tomography IV, Proc. SPIE vol. 5535 (2004), pp. 352-360.
Momose, "Recent Advances in X-ray Phase Imaging", Jpn. J. Appl. Phys. vol. 44 (2005), pp. 6355-6367.
Montgomery, "Self Imaging Objects of Infinite Aperture," J. Opt. Soc. Am. vol. 57(6), (1967), pp. 772-778.
Morimoto et al., "Development of multiline embedded X-ray targets for X-ray phase contrast imaging," XTOP 2012 Book of Abstracts, (Ioffe Physical-Technical Institute of the Russian Academy of Sciences, St. Petersburg, Russia, 2012), pp. 74-75.
Morimoto et al., X-ray phase contrast imaging by compact Talbot-Lau interferometer with a signal transmission grating, 2014, Optics Letters, vol. 39, No. 15, pp. 4297-4300.
Munro et al., Design of a novel phase contrast imaging system for mammography, 2010, Physics in Medicine and Biology, vol. 55, No. 14, pp. 4169-4185.
Nango et al., "Talbot-defocus multiscan tomography using the synchrotron X-ray microscope to study the lacuno-canalicular network in mouse bone", Biomed. Opt. Express vol. 4 (2013), pp. 917-923.
Neuhausler et al., "Non-destructive high-resolution X-ray imaging of ULSI micro-electronics using keV X-ray microscopy in Zernike phase contrast," Microelectronic Engineering, Elsevier Publishers BV., Amsterdam, NO, vol. 83, No. 4-9 (Apr. 1, 2006) pp. 1043-1046.
Newville, "Fundamentals of XAFS," (Univ. of Chicago, Chicago, IL, Jul. 23, 2004).
Noda et al., "Fabrication of Diffraction Grating with High Aspect Ratio Using X-ray Lithography Technique for X-ray Phase Imaging," Jpn. J. Appl. Phys. vol. 46, (2007), pp. 849-851.
Noda et al., "Fabrication of High Aspect Ratio X-ray Grating Using X-ray Lithography" J. Solid Mech_ Mater. Eng. vol. 3 (2009), pp. 416-423.
Nojeh, "Carbon Nanotube Electron Sources: From Electron Beams to Energy Conversion and Optophononics", ISRN Nanomaterials vol. 2014 (2014): 879827.
Nuhn, "From storage rings to free electron lasers for hard x-rays", J.A37 Phys.: Condens. Matter vol. 16 (2004), pp. S3413-S34121.
Nykanen et al., "X-ray scattering in full-field digital mammography," Med. Phys. vol. 30(7), (2003), pp. 1864-1873.
Oji et al., Automatic XAFS measurement system developed at BL14B2 in SPring-8, Available online Nov. 15, 2011, Journal of Synchrotron Radiation, vol. 19, pp. 54-59.
Olbinado et al., "Demonstration of Stroboscopic X-ray Talbot Interferometry Using Polychromatic Synchrotron and Laboratory X-ray Sources", Appl. Phys. Express vol. 6 (2013), 096601.
Ortega et al., "Bio-metals imaging and speciation in cells using proton and synchrotron radiation X-ray microspectroscopy," J. Royal Society Interface vol. 6 suppl. 5 (Oct. 6, 2009), pp. 6S649-6S658.
Otendal et al., A 9 keV electron-impact liquid-gallium-jet x-ray source, Rev. Sci. Instrum. vol. 79 (2008): 016102.
Oxford Instruments Inc., Series 5000 Model XTF5011 X-ray Tube information, Jun. 1998, 3 pages.
Parrill et al., "GISAXS—Glancing Incidence Small Angle X-ray Scattering," Journal de Physique IV, vol. 3 (Dec. 1993), pp. 411-417.
Paxscan Flat Panel X-ray Imaging, Varian Sales Brochure, (Varian Medical Systems, Palo Alto, CA, Nov. 11, 2004).
Pfeiffer et al., "Hard-X-ray dark-field imaging using a grating interferometer," Nature Materials vol. 7, (2008), pp. 134-137.
Pfeiffer et al., "Hard x-ray phase tomography with low brilliance x-ray sources," Phys. Rev. Lett. vol. 98, (2007), 108105.
Pfeiffer et al., "Phase retrieval and differential phase-contrast imaging with low-brilliance X-ray sources," Nature Physics vol. 2, (2006), pp. 258-261.
Pfeiffer, "Milestones and basic principles of grating-based x-ray and neutron phase-contrast imaging," in International Workshop on X-ray and Neutron Phase Imaging with Gratings AIP Conf. Proc. vol. 1466, (2012), pp. 2-11.
Pianetta et al., "Application of synchrotron radiation to TXRF analysis of metal contamination on silicon wafer surfaces," Thin Solid Films, vol. 373(1-2), 2000, pp. 222-226.
Potts, "Electron Probe Microanalysis", Ch. 10 of "A Handbook of Silicate Rock Analysis" (Springer Science + Business Media, New York, 1987), pp. 326-382 (equation quoted from p. 336).
Prewitt et al., "FIB Repair of 5X Recticles and Effects on IC Quality," Integrated Circuit Metrology, Inspection, and Process Control VII, Proc. SPIE vol. 1926 (1993), pp. 517-526.
Prewitt et al., "Focused ion beam repair: staining of photomasks and reticles," J. Phys. D Appl. Phys. vol. 26 (1993), pp. 1135-1137.
Prewitt et al., "Gallium Staining in FIB Repair of Photomasks," Microelectronic Engineering, vol. 21 (1993), pp. 191-196.
Qin et al., "Trace metal imaging with high spatial resolution: Applications in biomedicine," Metallomics, vol. 3 (Jan. 2011), pp. 28-37.
Rayleigh, "On copying diffraction gratings and some phenomena connected therewith," Philos. Mag. vol. 11 (1881), pp. 196-205.
Renaud et al., "Probing surface and interface morphology with Grazing Incidence Small Angle X-ray Scattering," Surface Science Reports, vol. 64:8 (2009), pp. 255-380.
Riege, "Electron Emission from Ferroelectrics—A Review", CERN Report CERN AT/93-18 (CERN, Geneva, Switzerland, Jul. 1993).
Röntgen, Ueber eine neue Art von Strahlen (Wurzburg Verlag, Warzburg, Germany, 1896) also, in English, "On a New Kind of Rays," Nature vol. 53 (Jan. 23, 1896). pp. 274-276.
Rovezzi, "Study of the local order around magnetic impurities in semiconductors for spintronics." PhD Dissertation, Condensed Matter, Université Joseph-Fourier—Grenoble I, 2009, English <tel-00442852>.
Rutishauser, "X-ray grating interferometry for imaging and metrology," 2003, Eth Zurich, Diss. ETH No. 20939.
Sato et al., Two-dimensional gratings-based phase-contrast imaging using a conventional x-ray tube, 2011, Optics Letters, vol. 36, No. 18, pp. 3551-3553.
Scherer et al., "Bi-Directional X-Ray Phase-Contrast Mammography," PLoS ONE, vol. 9, Issue 5 (May 2014) e93502.
Scholz, "X-ray Tubes and Monochromators," Technical Workshop EPIV, Universität Würzburg (2007); 41 slides, 2007.
Scholze et al., "X-ray Detectors and XRF Detection Channels," Ch. 4 of "Handbook of Practical X-Ray Fluorescence Analysis," B. Beckhoff et al., eds. (Springer, Berlin Heidelberg, Germay, 2006), pp. 85-198.
Sebert, "Flat-panel detectors:how much better are they?" Pediatr. Radiol. vol. 36 (Suppl 2), (2006), pp. 173-181.
Shen, "Polarizing Crystal Optics," Ch. 25 of "Handbook of Optics vol. III, 2nd Ed.," (McGraw Hill, New York, 2001).
Shields et al., "Overview of Polycapillary X-ray Optics," Powder Diffraction, vol. 17(2) (Jun. 2002), pp. 70-80.
Shimura et al., "Hard x-ray phase contrast imaging using a tabletop Talbot-Lau interferometer with multiline embedded x-ray targets", Opt. Lett. vol. 38(2) (2013), pp. 157-159.
Siddons, "Crystal Monochromators and Bent Crystals," Ch. 22 of "Handbook of Optics vol. III, 2nd Ed.," (McGraw Hill, New York, 2001).
Smith, "Fundamentals of Digital Mammography:Physics, Technology and Practical Considerations," Publication R-BI-016 (Hologic, Inc., Bedford, MA, Mar. 2005).
Snigirev et al., "Hard X-Ray Microoptics," Ch. 17 of "Modern Developments in X-Ray and Neutron Optics," A. Erko et al., eds (Springer, Berlin, Germany, 2008), pp. 255-285.
Sparks Jr., "X-ray Fluorescence Microprobe for Chemical Analysis," in Synchrotron Radiation Research, H. Winick & S. Doniach, eds. (Plenum Press, New York, NY 1980), pp. 459-512.

(56) References Cited

OTHER PUBLICATIONS

Spiller, "Multilayers," Ch. 24 of "Handbook of Optics vol. III, 2nd Ed.," (McGraw Hill, New York, 2001).
Stampanoni et al., "The First Analysis and Clinical Evaluation of Native Breast Tissue Using Differential Phase-Contrast Mammography," Investigative Radiology, vol. 46, pp. 801-806. pub 2011-12-xx.
Strüder et al., "Silicon Drift Detectors for X-ray Imaging," Presentation at Detector Workshop on Synchrotron Radiation Instrumentation, 54 slides, (Argonne Nat'l Lab, Argonne, IL Dec. 8, 2005), available at: <http://www.aps.anl.gov/News/Conferences/2005/Synchrotron_Radiation_Instrumentation/Presentations/Strueder.pdf>.
Suzuki et al., "Hard X-ray Imaging Microscopy using X-ray Guide Tube as Beam Condenser for Field Illumination," J. Phys.: Conf. Ser. vol. 463 (2013): 012028.
Suzuki, "Development of the DIGITEX Safire Cardiac System Equipped with Direct conversion Flat Panel Detector," Digital Angio Technical Report (Shimadzu Corp., Kyoto, Japan, no date, published 2004 with product release).
Takahama, "RADspeed safire Digital General Radiography System Equipped with New Direct-Conversion FPD," Medical Now, No. 62 (2007).
Takeda et al., "Differential Phase X-ray Imaging Microscopy with X-ray Talbot Interferometer". Appl. Phys. Express vol. 1 (2008) 117002.
Takeda et al., "X-Ray Phase Imaging with Single Phase Grating", Jpn. J. Appl. Phys. vol. 46 (2007), pp. L89-L91.
Takeda et al., "In vivo physiological saline-infused hepatic vessel imaging using a two-crystal-interferometer-based phase-contrast X-ray technique", J. Synchrotron Radiation vol. 19 (2012), pp. 252-256.
Talbot, "Facts relating to optical science No. IV," Philos. Mag. vol. 9 (1836), pp. 401-407.
Tanaka et al., "Cadaveric and in vivo human joint imaging based on differential phase contrast by X-ray Talbot-Lau interferometry", Z. Med. Phys. vol. 23 (2013), pp. 222-227.
Tang et al., "Micro-computed tomography (Micro-CT): a novel appraoch for intraoperative breast cancer specimen imaging," Breast Cancer Res. Treat. vol. 139, pp. 311-316 (2013).
Taniguchi et al., "Diamond nanoimprint lithography," Nanotechnology, vol. 13 (2002) pp. 592-596.
Tkachuk et al., "High-resolution x-ray tomography using laboratory sources", in Developments in X-Ray Tomography V, Proc. SPIE 6318 (2006): 631810.
Tkachuk et al., "Multi-length scale x-ray tomography using laboratory and synchrotron sources", Microsc. Microanal. vol. 13 (Suppl. 2) (2007), pp. 1570-1571.
Touzelbaev et al., "Applications of micron-scale passive diamond layers for the integrated circuits and microelectromechanical systems industries," Diamond and Rel. Mat'ls, vol. 7 (1998) pp. 1-14.
Tsuji et al., "X-Ray Spectrometry: Recent Technological Acvances," John Wiley & Sons Ltd. Chichester, West Susses, UK 2004), Chapters 1-7.
Udagawa, "An Introduction to In-House EXAFS Facilities," The Rigaku Journal, vol. 6, (1) (1989), pp. 20-27.
Udagawa, "An Introduction to X-ray Absorption Fine Structure," The Rigaku Journal, vol. 11(2)(1994), pp. 30-39.
Uehara et al., "Effectiveness of X-ray grating interferometry for non-destructive inspection of packaged devices", J. Appl. Phys. vol. 114 (2013), 134901.
Vogt, "X-ray Fluorescence Microscopy: A Tool for Biology, Life Science and Nanomedicine," Presentation on May 16, 2012 at James Madison Univ., Harrisonburg, VA (31 slides), 2012.
Wan et al.,"Fabrication of Multiple Slit Using Stacked-Sliced Method for Hard X-ray Talbot-Lau Interferometer", Jpn. J. Appl. Phys. vol. 47 (2008), pp. 7412-7414.
Wang et al., "Advantages of intermediate X-ray energies in Zernicke phase constrast X-ray microscopy," Biotech. Adv., vol. 31 (2013) pp. 387-392.
Wang et al., "Non-invasive classification of microcalcifications with phase-contrast X-ray mammography," Nature Comm. vol. 5:3797, pp. 1-9 (2014).
Wang, On the single-photon-counting (SPC) modes of imaging using an XFEL source, presented at IWORLD2015.
Wang et al., "Precise patterning of diamond films for MEMS application" Journal of Materials Processing Technology vol. 127 (2002), pp. 230-233.
Weitkamp et al., "Design aspects of X-ray grating interferometry," in International Workshop on X-ray and Neutron Phase Imaging with Gratings AIP Conf. Proc. vol. 1466, (2012), pp. 84-89.
Weitkamp et al., "Hard X-ray phase imaging and tomography with a grating interferometer," Proc. SPIE vol. 5535, (2004), pp. 137-142.
Weitkamp et al., "X-ray wavefront diagnostics with Talbot interferometers," International Workshop on X-Ray Diagnostics and Scientific Application of the European XFEL, Ryn, Poland, (2010), 36 slides.
Weitkamp et al., Tomography with grating interferometers at low-brilliance sources, 2006, SPIE, vol. 6318, pp. 0S-1 to 0S-10.
Weitkamp et al., "X-ray phase imaging with a grating interferometer," Opt. Express vol. 13(16), (2005), pp. 6296-6304.
Weitkamp et al., "X-ray wavefront analysis and optics characterization with a grating interferometer," Appl. Phys. Lett. vol. 86, (2005), 054101.
Wen et al., "Fourier X-ray Scattering Radiography Yields Bone Structural Information," Radiology, vol. 251 (2009) pp. 910-918.
Wen et al., "Single-shot x-ray differential phase-contrast and diffraction imaging using two-dimensional transmission gratings," Op. Lett. vol. 35, No. 12, (2010) pp. 1932-1934.
Wobrauschek et al., "Energy Dispersive, X-Ray Fluorescence Analysis," Encyclopedia of Analytical Chemistry, R.A. Meyers, Ed. (Wiley 2010).
Wobrauschek et al., "Micro XRF of light elements using a polycapillary lens and an ultra-thin window Silicon Drift Detector inside a vacuum chamber," 2005, International Centre for Diffraction Data 2005, Advances in X-ray Analysis, vol. 48, pp. 229-235.
Wolter, "Spiegelsysteme streifenden Einfalls als abbildende Optiken fur Rontgenstrahlen" [Grazing Incidence Reflector Systems as Imaging Optics for X-rays] Annalen der Physik vol. 445, Issue 1-2 (1952), pp. 94-114.
X-ray-Optics.de Website, http://www.x-ray-optics.de/, accessed Feb. 13, 2016.
Yakimchuk et al., "Ellipsoidal Concentrators for Laboratory X-ray Sources: Analytical approaches for optimization," Mar. 22, 2013, Crystallography Reports, vol. 58, No. 2, pp. 355-364.
Yamamoto, "Fundamental physics of vacuum electron sources", Reports on Progress in Physics vol. 69, (2006), pp. 181-232.
Yanagihara et al., "X-Ray Optics," Ch. 3 of "X-ray Spectrometry: Recent Technological Advances," K. Tsuji et al. eds. (John Wiley & Sons, Ltd. Chichester, West Sussex, UK, 2004), pp. 63-131.
Yang et al., "Analysis of Intrinsic Stress in Diamond Films by X-ray Diffraction," Advances in X-ray Analysis, vol. 43 (2000), pp. 151-156.
Yashiro et al., "Distribution of unresolvable anisotropic microstructures revealed in visibility-contrast images using x-ray Talbot interferometry", Phys. Rev. B vol. 84 (2011), 094106.
Yashiro et al., "Hard x-ray phase-imaging microscopy using the self-imaging phenomenon of a transmission grating", Phys. Rev. A vol. 82 (2010), 043822.
Yashiro et al., "Theoretical Aspect of X-ray Phase Microscopy with Transmission Gratings" in International Workshop on X-ray and Neutron Phase Imaging with Gratings, AIP Conf. Proc. vol. 1466, (2012), pp. 144-149.
Yashiro et al., "X-ray Phase Imaging and Tomography Using a Fresnel Zone Plate and a Transmission Grating", in "The 10th International Conference on X-ray Microscopy Radiation Instrumentation", AIP Conf. Proc. vol. 1365 (2011) pp. 317-320.
Yashiro et al., "Efficiency of capturing a phase image using cone-beam x-ray Talbot interferometry", J. Opt. Soc. Am. A vol. 25 (2008), pp. 2025-2039.
Yashiro et al., "On the origin of visibility contrast in x-ray Talbot interferometry", Opt. Express (2010), pp. 16890-16901.

(56) References Cited

OTHER PUBLICATIONS

Yashiro et al., "Optimal Design of Transmission Grating for X-ray Talbot Interferometer", Advances in X-ray Analysis vol. 49(3) (2006), pp. 375-379.

Yashiro et al., "X-ray Phase Imaging Microscopy using a Fresnel Zone Plate and a Transmission Grating", in The 10th International Conference on Synchrotron Radiation Instrumentation, AIP Conf. Proc. vol. 1234 (2010), pp. 473-476.

Yashiro et. al., "Hard-X-Ray Phase-Difference Microscopy Using a Fresnel Zone Plate and a Transmission Grating", Phys. Rev. Lett. vol. 103 (2009), 180801.

Yu et al., "Morphology and Microstructure of Tungsten Films by Magnetron Sputtering," Mat. Sci. Forum, vol. 913, pp. 416-423 (2018).

Zanette et al., "Two-Dimensional X-Ray Grating interferometer," Phys. Rev. Lett. vol. 105 (2010) pp. 248102-1 248102-4.

Zeng et al., "Ellipsoidal and parabolic glass capillaries as condensers for x-ray microscopes," Appl. Opt. vol. 47 (May 2008), pp. 2376-2381.

Zeng et al., "Glass Monocapillary X-ray Optics and Their Applications in X-Ray Microscopy," X-ray Optics and Microanalysis: Proceedings of the 20th International Congress, AIP Conf. Proc. vol. 1221, (2010), pp. 41-47.

Zhang et al., "Fabrication of Diamond Microstructures by Using Dry and Wet Etching Methods", Plasma Science and Technology vol. 15(6) (Jun. 2013), pp. 552-554.

Dong et al., "Improving Moleular Sensitivity X-Ray Fluorescence Molecular Imaging (XFMI) of Iodine Distribution in Mouse-Sized Phantoms via Excitation Spectrum Optimization," IEEE Access, vol. 6, pp. 56966-56976 (2018).

Office Action received in Japanese Application No. 2016-564245, dated Oct. 12, 2018.

Hennekam et al., "Trace metal analysis of sediment cores using a novel X-ray fluorescence core scanning method," Quaternary Int'l, https://doi.org/10.1016/j.quaint.2018.10.018 (2018).

Malzer et al., "A laboratory spectrometer for high throughput X-ray emission spectroscopy in catalysis research," Rev. Sci. Inst. 89, 113111 (2018).

Office Action received in Japanese Application No. 2016-564245, dated Oct. 23, 2018.

Li et al., "X-ray phase-contrast imaging using cascade Talbot-Lau interferometers," Proc. SPIE 10964 (2018), pp. 1096469-1-1096469-6.

Sun et al., "Combined optic system based on polycapillary X-ray optics and single-bounce monocapillary optics for focusing X-rays from a conventional laboratory X-ray source," Nucl. Inst. and Methods in Phys. Res. A 802 (2015) pp. 5-9.

Sun et al., "Numerical design of in-line X-ray phase-contrast imaging based on ellipsoidal single-bounce monocapillary," Nucl. Inst. and Methods in Phys. Res. A746 (2014) pp. 33-38.

Töpperwien et al., "Multiscale x-ray phase-contrast tomography in a mouse model of transient focal cerebral ischemia," Biomed. Op. Express, vol. 10, No. 1, Jan. 2019, pp. 92-103.

Viermetz et al., "High resolution laboratory grating-based X-ray phase-contrast CT," Scientific Reports 8:15884 (2018).

Zhang et al., "Application of confocal X-ray fluorescence based on capillary X-ray optics in nondestructively measuring the inner diameter of monocapillary optics," Optics Comm. (2018) https://doi.org/10.1016/j.optcom.2018.11.064.

Zhang et al., "Measurement of the inner diameter of monocapillary with confocal X-ray scattering technology based on capillary X-ray optics," Appl. Opt. (Jan. 8, 2019), doc ID 351489, pp. 1-10.

Jahrman et al., "Vacuum formed temporary spherically and toroidally bent crystal analyzers for x-ray absorption and x-ray emission spectroscopy," Rev. Sci. Inst. vol. 90, 013106 (2019).

Lühl et al., "Scanning transmission X-ray microscopy with efficient X-ray fluorescence detection (STXM-XRF) for biomedical applications in the soft and tender energy range," J. Synch. Rad. vol. 26, https://doi.org/10.1107/S1600577518016879, (2019).

Scott, "Hybrid Semiconductor Detectors for High Spatial Resolution Phase-contrast X-ray Imaging," Thesis, University of Waterloo, Department of Electrical and Computer Engineering, 2019.

Sunday et al., "X-ray Metrology for the Semiconductor Industry Tutorial," J. Res. Nat'l Inst. Stan. vol. 124: 124003 (2019); https://doi.org/10.6028/jres.124.003.

Office Action received in Chinese Patent Application No. 201580021722.8, dated Jan. 28, 2019.

\* cited by examiner

X-RAY TECHNIQUES USING STRUCTURED ILLUMINATION

CROSS-REFERENCE TO RELATED APPLICATIONS

This Patent Application is a continuation-in-part of U.S. patent application Ser. No. 14/712,917, filed May 15, 2015 and entitled "X-RAY METHOD FOR THE MEASUREMENT, CHARACTERIZATION, AND ANALYSIS OF PERIODIC STRUCTURES", which claims the benefit of U.S. Provisional Patent Application No. 61/993,792, filed May 15, 2014 and entitled "Method of Talbot-Effect Based X-ray Patterned Probe and Characterization (Metrology or Inspection) Apparatuses Using Such", and is also a continuation-in-part of application Ser. No. 14/700,137, filed Apr. 29, 2015 and entitled "X-RAY INTERFEROMETRIC IMAGING SYSTEM", which in turn claims the benefit of Provisional Patent Application No. 61/993,811, filed May 15, 2014 and entitled "Method of Talbot Effect based X-ray Imaging with High Image Contrast and Design of Apparatus Using Such", all of which are incorporated herein by reference in their entirety; the present Application additionally claims the benefit of U.S. Provisional Patent Application Nos. 62/171,377 filed on Jun. 5, 2015 and entitled "X-RAY TECHNIQUES USING STRUCTURED ILLUMINATION", and 62/343,594, filed on May 31, 2016 and entitled "X-RAY MICRODIFFRACTION WITH STRUCTURED ILLUMINATION FOR STRAIN MEASUREMENT IN NANOELECTRONICS", all of which are incorporated herein by reference in their entirety.

STATEMENT REGARDING FEDERALLY SPONSORED RESEARCH

This Application relates to work supported in part by grant numbers 1R44EB021125-01 and 1R44EB23284-01A1 from the National Institutes of Health (NIH). The government may have certain rights to the invention.

FIELD OF THE INVENTION

The invention disclosed herein relates to a method and apparatus for the measurement of one or more designated property of an object, such as material composition or structure, using x-ray techniques.

BACKGROUND OF THE INVENTION

Current x-ray techniques, including fluorescence, diffraction, small angle scattering, absorption refraction, and absorption spectroscopy, typically use an illumination beam with a single continuous cross section with a regular shape, such as a circular or oval spot. Such an illumination beam is not optimized to obtain high signal to noise ratio and/or high throughput using x-ray technique(s) on an object containing a single region of interest of arbitrary shape, or on a number of physically separated regions of similar or different shapes that may include periodic identical regions, such as semiconductor interconnects and through silicon vias (TSVs).

As illustrated in the fluorescence example of FIGS. 1A and 1B, when a conventional illumination beam 888-A with a single contiguous round cross section illuminates a region(s) of interest (ROI(s)) (illustrated in this example by a structure 840 with the shape of a cross) in an object 240 to be measured, the surrounding areas of the ROI 840 are also illuminated. As a result, x-rays collected by the x-ray detector 290 include not only x-rays 886 from the ROI 840 (shown in the figure as fluorescence x-rays by way of example) but also include a significant number of x-rays 885 generated from the surrounding illuminated areas. Signals from the detector may pass through a signal processor 292 for further analysis using a computer 295, and then displayed on a monitor 298. Because x-rays 885 generated from the surrounding areas are also detected with those from the ROI(s), a reduction of signal-to-noise ratio or difficulty in data analysis may result.

One approach to address this problem has been the use of an x-ray beam with a size smaller than the ROI, as illustrated in FIGS. 2A and 2B. A focused x-ray beam 888-B is created that illuminates a single spot 290-B within the ROI 840. The fluorescence x-rays 886-B that radiate from the spot 290-B are entirely from the ROI. However, because only a small portion of the ROI is illuminated with a small x-ray illumination beam, the generated x-rays 886-B will also be small. Attempts to increase the signal by increasing the integration time reduce the throughput, and in any case provide no information on anything but the illuminated spot. Collecting data for the entire ROI will require additionally scanning the spot over the region, further reducing the throughput.

There is therefore a need for a method and a system that can provide x-ray measurements of ROI(s) of interest in an object with high signal-to-noise ratios (S/N(s)) and/or high measurement throughput.

BRIEF SUMMARY OF THE INVENTION

The invention disclosed herein relates to a method and apparatus for x-ray techniques using structured x-ray illumination beam for examining one or more properties of an object. In particular, an object with one or more regions of interest (ROIs) may be illuminated with a structured x-ray illumination beam whose spatial properties (cross-section and/or pattern) have been engineered to correspond to the ROIs, so that the x-rays of the illumination beam optimally overlap with the ROIs.

The ROIs typically contain at least one common material property and/or structure to be measured. These may include elemental composition, crystallographic phase and texture, size and/or size distribution of voids, particles, and inclusions, mass thickness, film thickness analysis, shape and/or size of particular features, and/or chemical state of an element of the ROI(s) in an object. The ROI(s) may be continuous but of arbitrary shape, such as rectangle, square, circle, cross, line, hexagon, and triangle. The ROIs may also contain a plurality of physically separated regions of arbitrary shapes. The ROIs may have identical shapes distributed in a periodic pattern.

The invention allows a greater x-ray flux to be used, enhancing the signal from the ROI(s) itself, while reducing unwanted signals from regions outside of the ROI(s), improving signal-to-noise ratios and/or measurement throughput. This may be used in conjunction with a number of x-ray measurement techniques, including x-ray fluorescence (XRF), x-ray diffraction (XRD), small angle x-ray scattering (SAXS), x-ray attenuation, x-ray refraction, x-ray absorption fine-structure spectroscopy (XAFS), x-ray near edge spectroscopy, and x-ray emission spectroscopy, singularly or in combination.

Figure 1A:
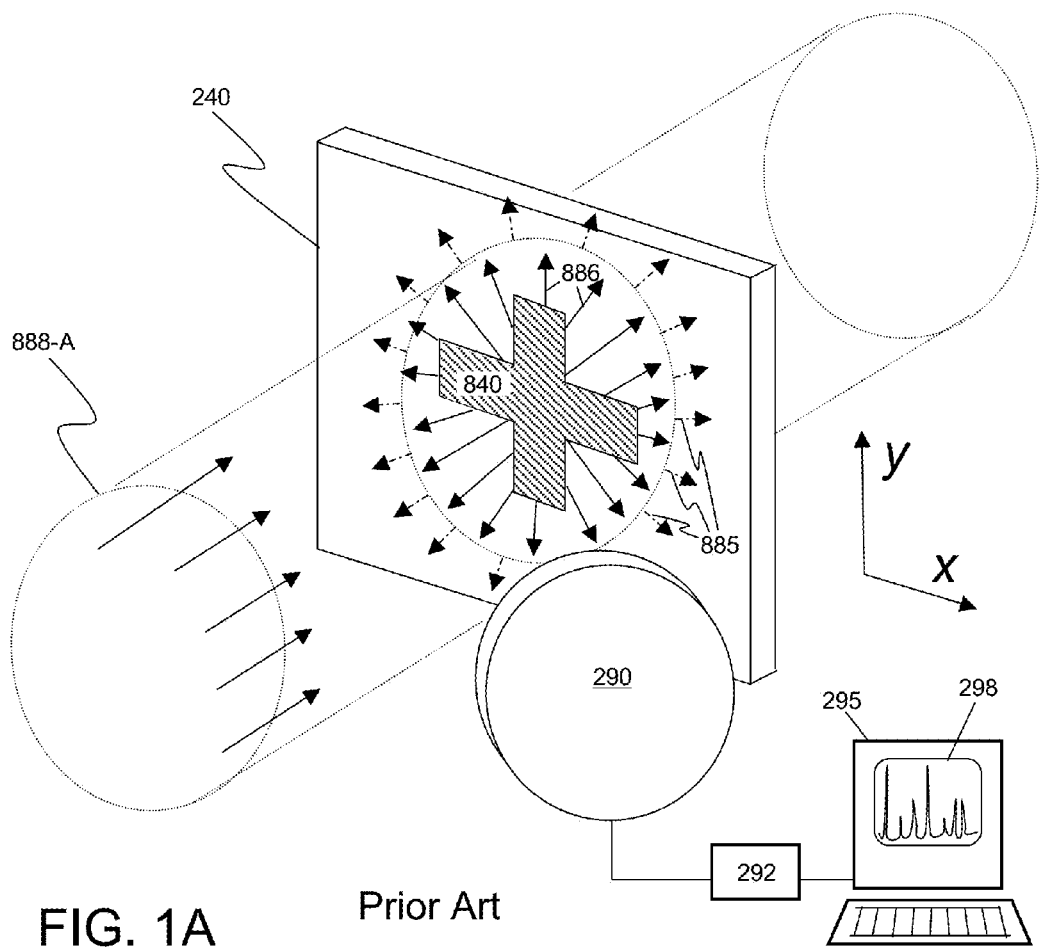
FIG. 1A illustrates a schematic diagram of a prior art x-ray measurement system.
Figure 1B:
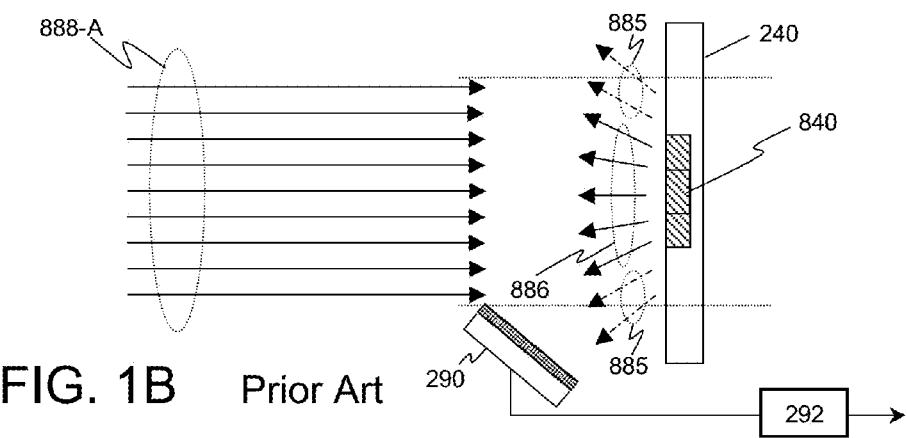
FIG. 1B illustrates a cross-section diagram of the prior art x-ray measurement system of FIG. 1A.

Note: Elements shown in the drawings are meant to illustrate the functioning of embodiments of the invention, and should not be assumed to have been drawn in proportion or to scale.

DETAILED DESCRIPTION OF THE INVENTION

1. Basic Embodiment and Method

The invention disclosed herein relates to a method and apparatus for x-ray techniques using structured x-ray illumination for examining a designated property of an object.

Figure 2A:
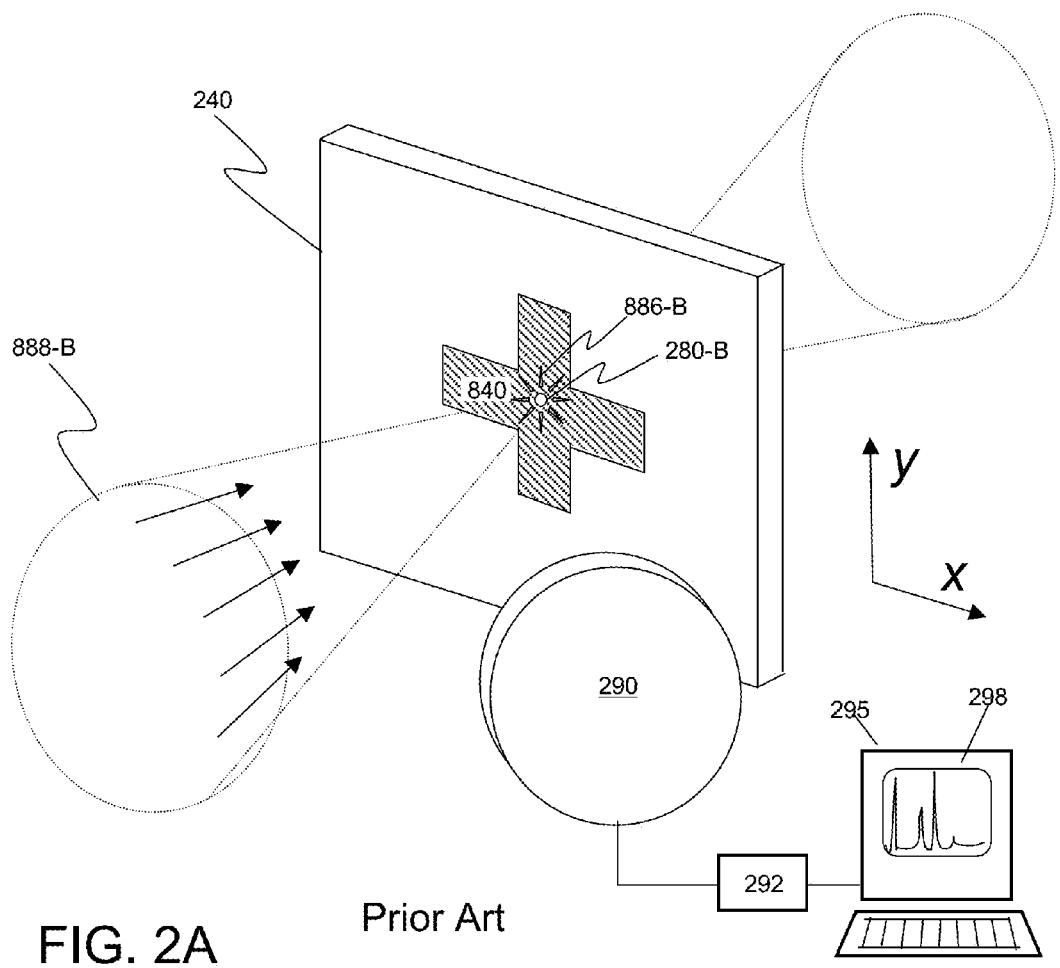
FIG. 2A illustrates a schematic diagram of a prior art x-ray microfocus measurement system.
Figure 2B:
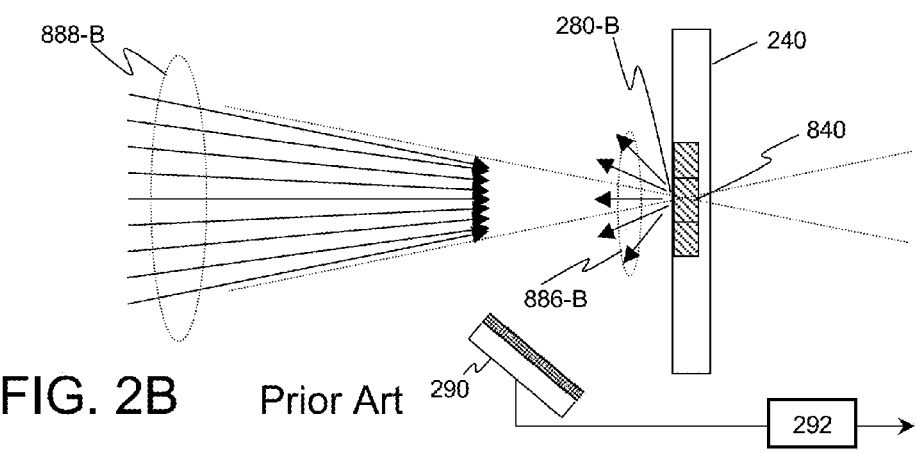
FIG. 2B illustrates a cross-section diagram of the prior art x-ray microfocus measurement system of FIG. 2A.
Figure 3A:
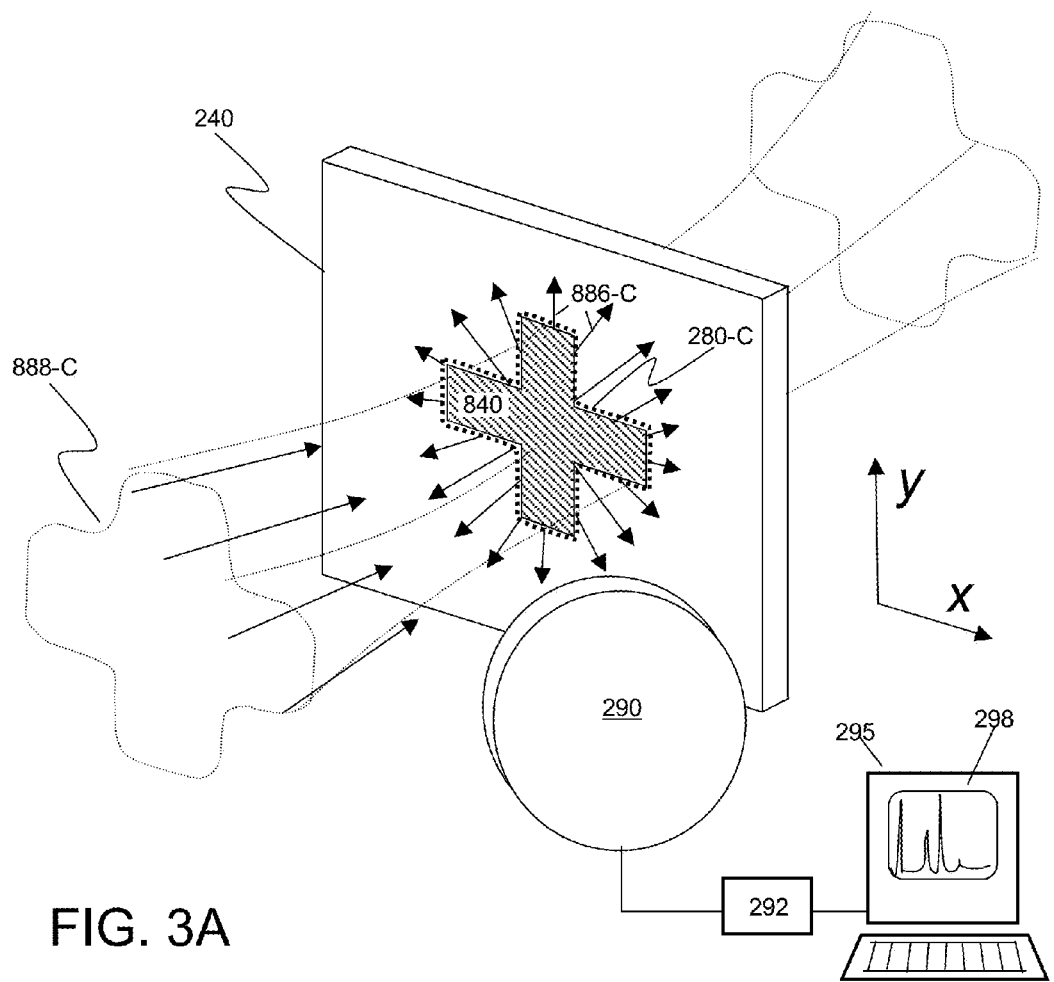
FIG. 3A illustrates a schematic diagram of an x-ray measurement system according to the invention.
Figure 3B:
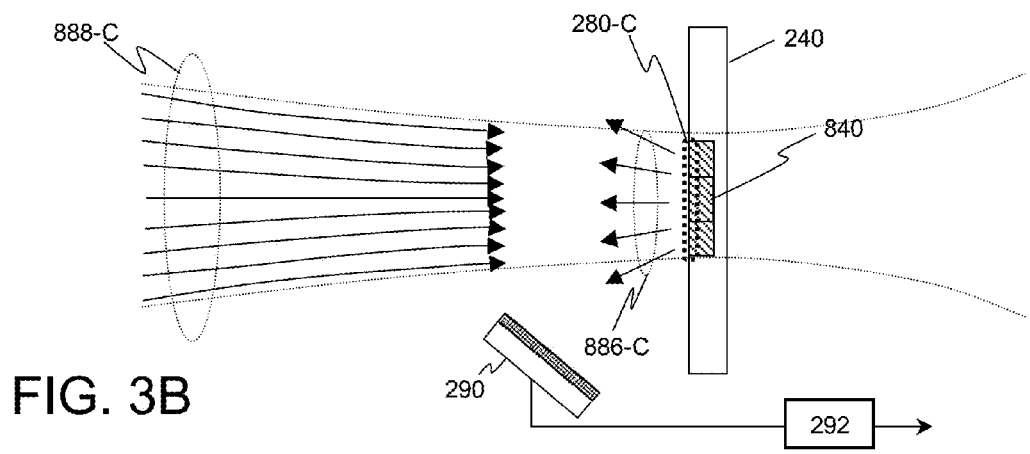
FIG. 3B illustrates a cross-section diagram of the x-ray measurement system of FIG. 3A.

FIGS. 3A and 3B illustrate the use of one embodiment of the invention for use with the object 240 as was illustrated in FIGS. 2A and 2B. The x-ray beam 888-C has a profile such that, at the object 240, the cross section of the x-ray beam 280-C converges to have the same size and shape as the ROI 840 of the object 240, represented in these figures by a cross-shaped region. Higher x-ray flux may therefore be used since the x-rays are distributed over a larger area, generating a larger signal, and yet, if the beam 280-C and the ROI 840 are well matched, x-ray signal(s) from the surrounding area of the ROI 840 will be minimized, improving the signal-to-noise ratio and/or measurement throughput.

1.1. Steps of a Method According to the Invention

Figure 4:
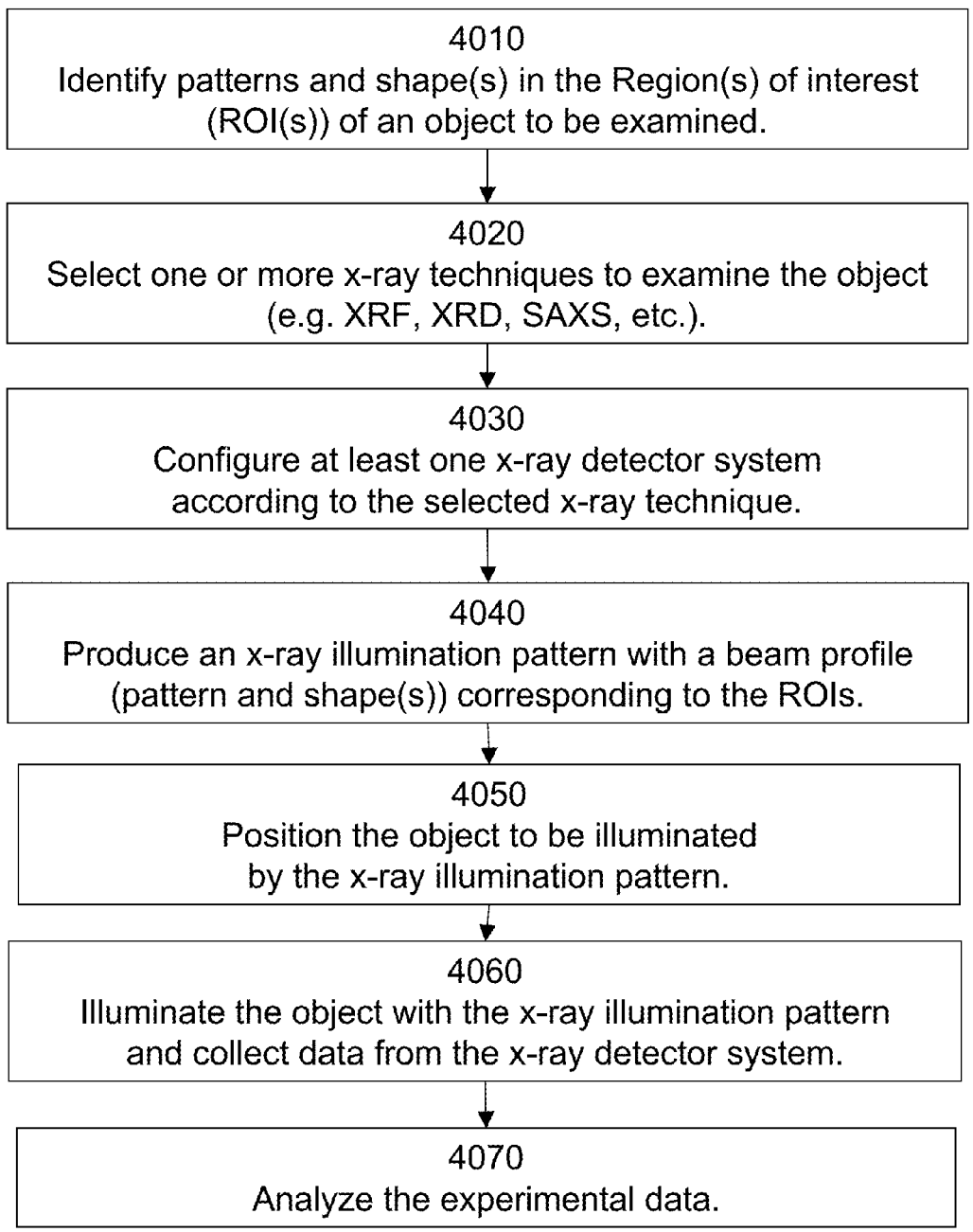
FIG. 4 presents a flow diagram for a method of x-ray measurement according to the invention.

An example of a method according to the invention is illustrated in the flow diagram of FIG. 4, and comprises several steps.

The first step 4010 comprises identifying the region(s) of interest (ROI(s)) to be examined in an object in terms of properties to be measured, such as composition, crystallographic structure, chemical state(s) of one or more elements. The cross section(s) (shape(s) of the ROI(s)) and, if there are a plurality of physically separated ROIs, the distribution pattern of these ROIs, are determined along a pre-selected direction along which an x-ray beam will be directed toward the object. The ROIs may have the same or different shapes and sizes, and may be arranged in a periodic or arbitrary pattern. The ROI(s) may correspond to manufactured structure(s) of component(s) of a device, integrated circuits or the like, in which the structured illumination beam is designed to match the expected manufactured object. Alternatively, the ROIs may correspond to naturally occurring portions of mineral composites, which may be identified by prior microscopic examination.

This is followed by a step 4020 comprising selecting one or more appropriate x-ray techniques to examine the common material property (such as composition, crystallographic phase, structure, and/or chemical state). The techniques may be used to probe the object in reflection or transmission, and may comprise any one of, or a combination of, techniques such as x-ray fluorescence (XRF), x-ray diffraction (XRD), small angle x-ray scattering (SAXS), x-ray attenuation, x-ray refraction, x-ray absorption fine-structure spectroscopy (XAFS), x-ray near edge spectroscopy, and x-ray emission spectroscopy, singularly or in combination.

This is followed by a step 4030 comprising the configuration of one or more x-ray detectors appropriate to the selected x-ray technique(s) to collect the x-rays resulting from the interaction of the structured x-ray illumination beam with the ROI(s) of the object. These may include detectors positioned at upstream side of the object to detect fluorescent and/or diffracted x-rays, detectors positioned at downstream side of the object to detect diffracted x-rays and/or x-rays scattered at small angles, etc., and may also include beam stops to block x-rays propagating at certain angles, e.g. on-axis x-rays for SAXS measurements.

This is followed by a step 4040 comprising producing a structured x-ray illumination beam with the appropriate beam cross section and/or pattern along the pre-selected direction such that it corresponds to or identically matches at least a portion of the ROI(s) identified in the previous steps. This may be produced by first producing a structured source with a similar shape and/or pattern to the structured x-ray illumination beam and then using x-ray imaging optics to image the structured source with appropriate magnification to produce the structured x-ray illumination beam. The structured source can be produced by a number of methods, including the use of shadow masks placed in the x-ray beam path between the source and the x-ray imaging optics, the use of a structured electron excitation beam on the x-ray anode, the use of a structured target, or through the formation of a Talbot interference pattern.

This is followed by a step 4050 comprising positioning the object comprising ROI(s) so that some or all of the ROI(s) to be examined will be illuminated by the structured x-ray illumination beam.

This is followed by a step 4060 comprising illuminating the object and ROIs therein with the structured x-ray illumination beam, and using the selected x-ray technique(s) and appropriate detector(s) to collect x-rays emerging from the ROI(s) that are appropriate for the selected x-ray technique(s) and generate signals related to the detected x-rays.

This is followed by a step 4070 comprising analysis of the collected signal data to obtain information of the common properties of the ROI(s).

The method disclosed above is especially useful for examining a single ROI with an irregular shape or a plurality of physically separated ROIs for which a structured illumination x-ray beam can be constructed that illuminates primarily the ROI(s) and not the surrounding areas (non-ROI(s)).

Based on the specific examination desired, suitable x-ray technique(s) can be selected according to established capabilities. For example, x-ray fluorescence analysis, x-ray diffraction, x-ray mall angle scattering, x-ray absorption, x-ray reflectivity, and x-ray absorption spectroscopy can be used to measure, characterize, and analyze elemental composition or film thickness, crystallographic phase and texture, size and size distribution of voids, particles, and inclusions, mass thickness, film thickness analysis, lens-less high spatial resolution imaging, and chemical state of an element of the ROI(s) in an object, respectively. In some cases, two or more x-ray techniques can be used sequentially or simultaneously to obtain complementary information about the ROI(s).

1.2. Formation of a Shaped X-ray Illumination Beam

A suitable structured x-ray illumination system that produces x-ray beams with the appropriate structured x-ray illumination beam (e.g. pattern(s) and shape(s)) to match at least a portion of the ROI(s) selected for examination) may be provided to enable the method described above. The x-ray illumination system may comprise at least one structured x-ray source and at least one x-ray imaging optic.

In some embodiments, the structured x-ray source may only radiate x-rays in a spatial distribution corresponding to that of the ROI(s). The spatial distribution of x-ray generation can be achieved described below and are illustrated in FIGS. 5-8.

In FIGS. 5-8, a shaped illumination system for an object 240-P comprising a plurality of non-uniform ROIs 800 is shown. For these illustrations, the x-rays 889 that are detected by the detector 290 are those emerging on the far side of the object 240-P. These may be transmitted or fluorescence x-rays, x-rays diffracted or scattered by the object 240-P, etc., depending on the x-ray technique employed.

In all the illustrated cases, the object 240-P is illuminated by forming an image of a source 50/52/54 onto the object 240-P using an x-ray imaging optical system 1020. Such an x-ray optical imaging system may comprise zone plates, monocapillary optics with quadric surfaces, etc. and may be a 1:1 imaging system, a magnifying system, or a de-magnifying system, as will be described in further detail below.

1.2.1. X-ray Source

The x-ray source can be structured using various techniques.

Figure 5:
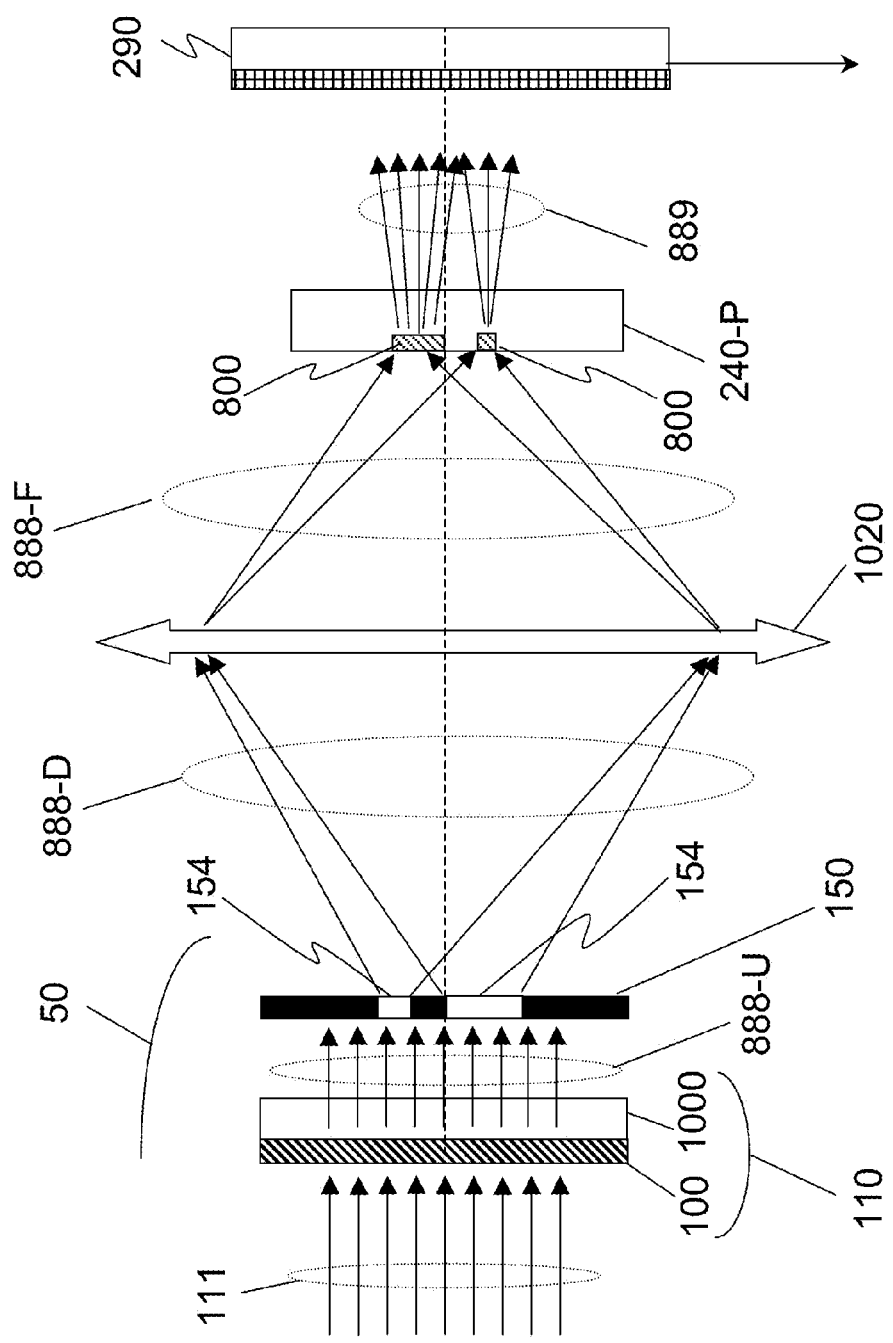
FIG. 5 presents a schematic cross-section illustration of a system according to the invention using a source comprising a plate with apertures.

In the embodiment illustrated in FIG. 5, the source 50 comprises an electron beam 111 bombarding an x-ray target 110 comprising a uniform layer of x-ray generating material 100 coated onto a substrate 1000. The uniform x-rays 888-U that are produced are then partially blocked by a screen 150 comprising apertures 154 that have sizes and shapes that correspond to the shape(s), size, and pattern(s) of the ROI(s) in the object 240-P. The apertures may be static apertures fixed in a plate, or may be adjustable apertures formed with movable blades, and may vary in size and shape over time. The transmitted x-rays 888-D then diverge into the x-ray imaging system 1020, which then focuses x-rays 888-F to form an image of the apertures 154 onto the ROIs 800 with appropriate image magnification. If the imaging system is a 1:1 imaging system (image magnification=1), the apertures 154 will generally be the same size, shape and relative orientation as the ROIs 800, but will typically be inverted relative to the ROIs 800.

Figure 6:
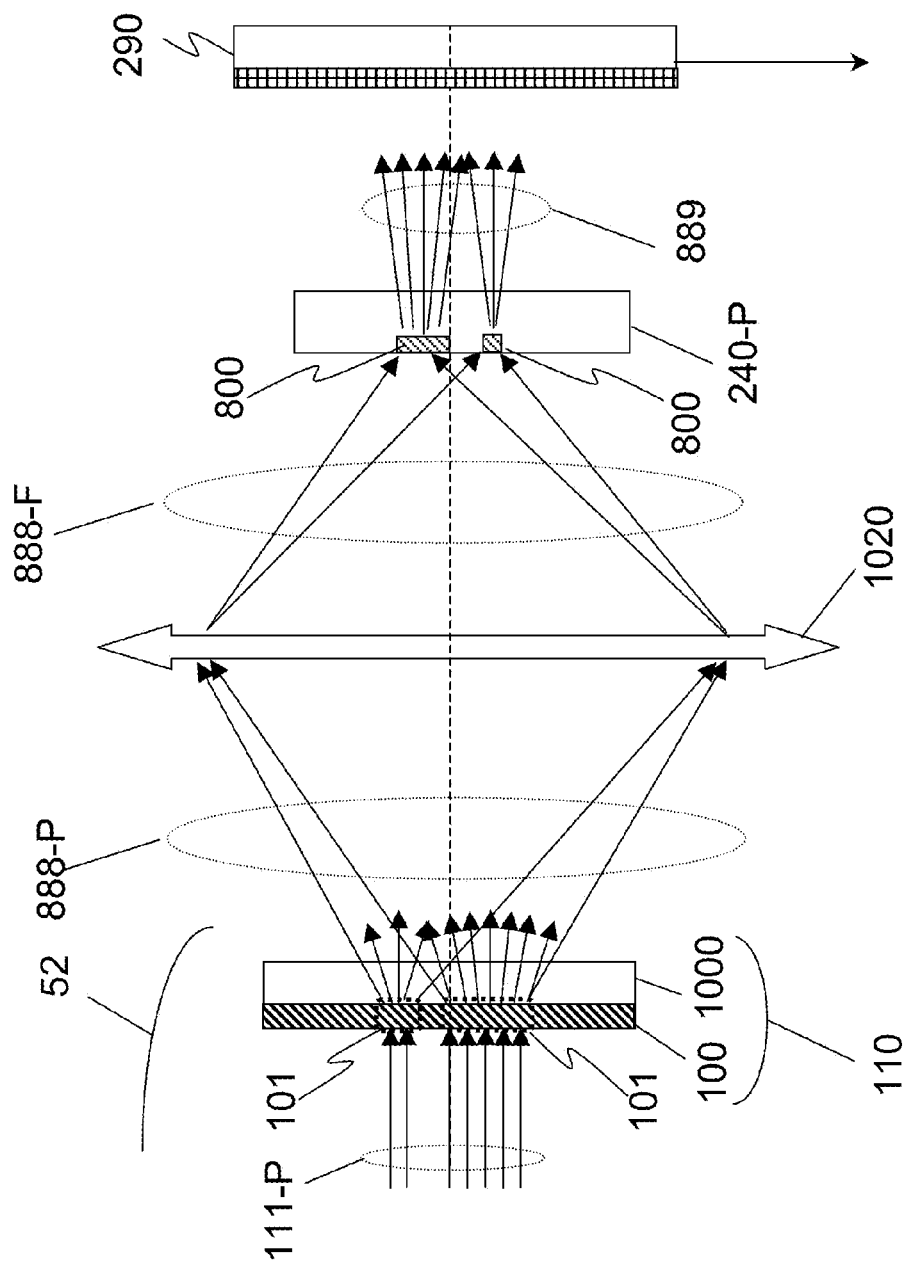
FIG. 6 presents a schematic cross-section illustration of a system according to the invention using an x-ray source comprising a patterned electron beam.

In the embodiment illustrated in FIG. 6, the source 52 comprises a shaped electron beam 111-P bombarding an x-ray target 110 comprising a uniform layer of x-ray generating material 100 coated onto a substrate 1000 with high x-ray transmission. X-rays 888-P are only generated in the regions 101 bombarded by electrons 111-P, and therefore form a patterned source.

The size and exposure of the electron beam 111-P may be controlled through apertures for the electron beam, or by rapid scanning of an electron beam with electron optics so that the electron exposure regions 101 have the sizes and shapes that correspond to the shape(s), size, and pattern(s) of the ROI(s) in the object 240-P. The x-rays 888-P that emerge from the target 110 then diverge into the x-ray imaging system 1020, which then focuses x-rays 888-F to form an image of the target 110 onto the ROIs 800. If the imaging system is a 1:1 imaging system, the exposure regions 101 will generally be the same size, shape and relative orientation as the ROIs 800, but will typically be inverted relative to the ROIs 800.

This technique may be especially useful if data for the object must be collected for areas larger than the field of view of the x-ray optical imaging system. The object position may be scanned in x and/or y (the coordinates perpendicular to the x-ray beam axis of propagation), and the electron beam adjusted to correspond to the moving object, allowing x-rays to be collected by the detector for a much larger area than the single field-of-view a single image could allow.

Figure 7:
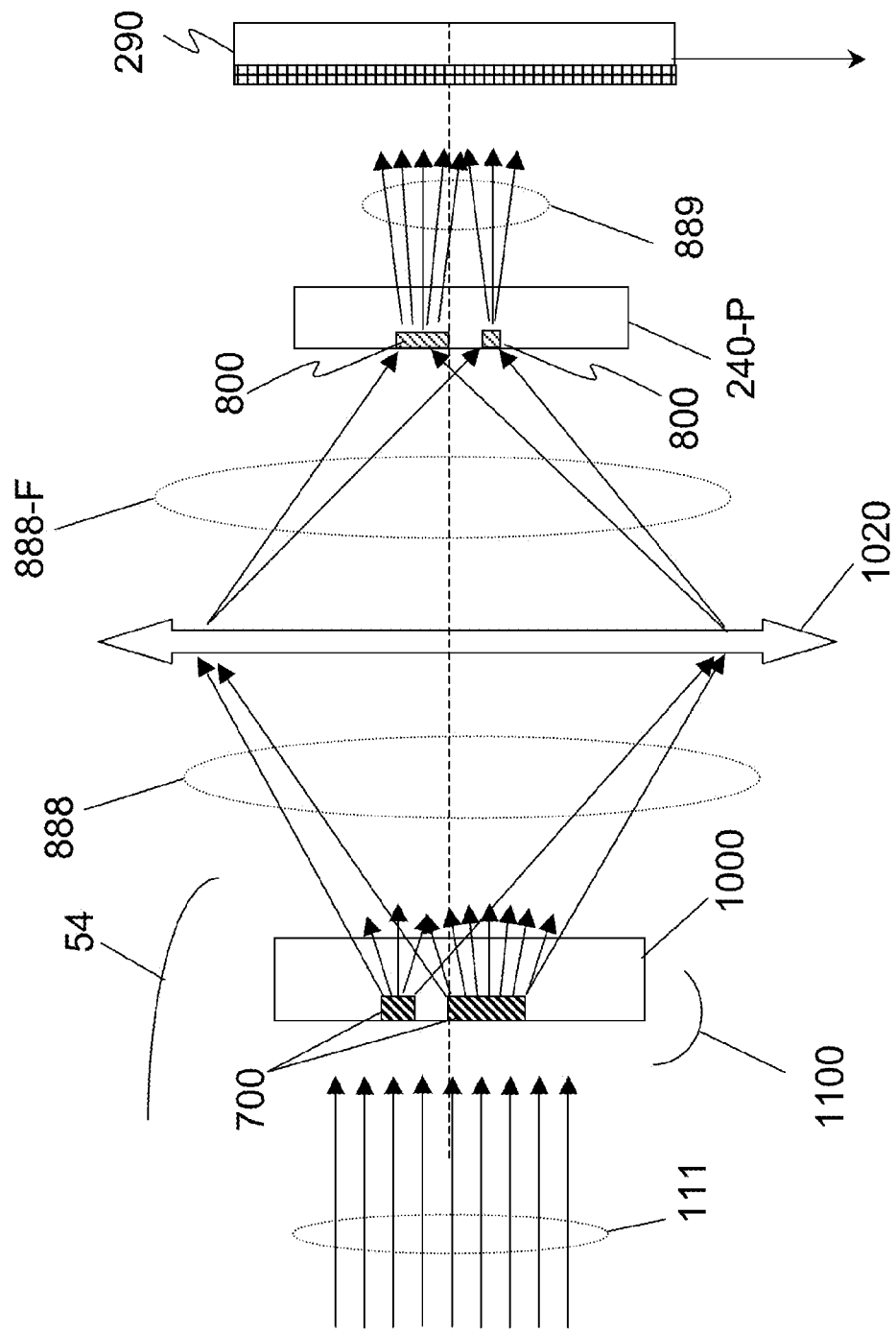
FIG. 7 presents a schematic cross-section illustration of a system according to the invention using an x-ray source comprising a structured x-ray target.
Figure 8:
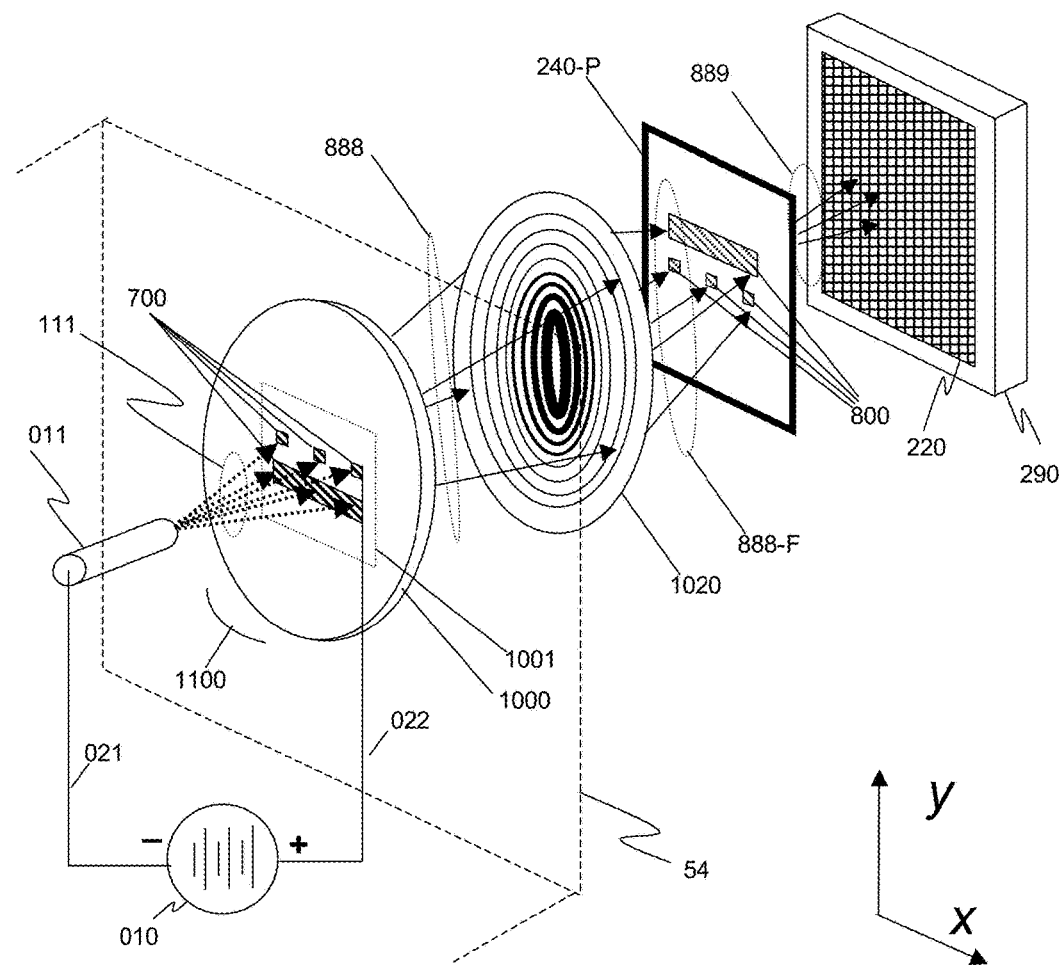
FIG. 8 presents a schematic perspective view of the system of FIG. 7.

In the embodiment illustrated in FIGS. 7 and 8, the source 54 comprises an electron beam 111 bombarding an x-ray target 1100 comprising a plurality of microstructures of x-ray generating material 700 embedded in a substrate 1000. Also shown in FIG. 8 are elements typical for x-ray sources: the high voltage source 010 that provides an accelerating voltage between the electron beam emitter 011 and the target 1100 through leads 021 and 022.

In this embodiment, the target has a region 1001 comprising structures 700 comprising x-ray generating material embedded in a substrate 1000 that correspond to the shape(s), size, and pattern(s) of the ROI(s) in the object 240-P to be examined. The structures 700 have the sizes and shapes that correspond to the shape(s), size, and the pattern(s) of the ROI(s) in the object 240-P. The x-rays 888 that emerge from the target 1100 then diverge into the x-ray imaging system 1020, which then focuses x-rays 888-F to form an image of the target 1100 onto the ROIs 800. If the imaging system is a 1:1 imaging system, the structures 700 will generally be the same size, shape and relative orientation as the ROIs 800, but will typically be inverted relative to the ROIs 800.

If the object structures 800 have a size on the order of micrometers, then the corresponding x-ray generating structures will also have dimensions on the order of micrometers. The x-ray generating structures 700 may in turn comprise plural of discrete finer microstructures, or be fabricated using a powder of x-ray generating material. If the object structures 800 are periodic, the x-ray generating structures may also be arranged in a periodic pattern. In some embodiments, the x-ray generating structures have lateral dimensions (dimensions in x and y, orthogonal to the x-ray optical axis of the system) measured on the order of microns, and with a thickness on the order of one half of the electron penetration depth within the substrate material. In some embodiments, the microstructures are formed in a regular two-dimensional array.

In these embodiments, the x-ray generating material will generally comprise x-ray generating materials selected for their x-ray spectral generating property (such as molybdenum (Mo) or tungsten (W)) in close thermal contact with a thermally conducting substrate of a low atomic number (low Z) material, such as diamond or beryllium (Be). In general, when the term "embedded" is used in this disclosure, at least half of the surface area of the structure will be in close thermal contact with the substrate.

1.2.2. X-Ray Optics

The x-ray imaging optical system can be any of a number of imaging x-ray optical elements, such as an x-ray zone plate, a Wolter optic, a system of reflective optical elements, or a compound refractive lens. The x-ray imaging optic is designed and configured to image the x-ray source with appropriate image magnification (or demagnification) to achieve a structured illumination beam incident on the object with a spatial distribution that matches at least a portion of the ROI(s) to be examined.

System design should consider the performances of the structured x-ray source and x-ray imaging optic together to achieve optimal performance for a given application. For example, zone plates have been demonstrated to form x-ray images with very high spatial resolution and low image distortion. To obtain a structured x-ray illumination beam with sub-100 nm shape(s), a zone plate is preferred as the x-ray imaging optic. When high throughput is important (and if high spatial resolution is not critical), a Wolter optic might be preferred. To obtain high throughput, an x-ray source with an anode comprising x-ray generating material embedded in a low Z substrate of good thermal property (such as diamond) is preferred.

Although FIGS. 5-7 show only two ROI(s) in this cross-sectional view, and FIG. 8 shows four ROI(s), the number of physically separated ROI(s) may range from 1 to 1 billion ($10^9$) or more. Beyond this, the shape of the each ROI may vary to be a number of regular shapes (such as line, cross, circle, rectangle, dot, etc.), or may be entirely arbitrary (e.g. grains within a mineral sample). In any case, the distribution of ROIs may be arbitrary (such as periodic or aperiodic), and the dimensions of each ROI may range from 10 nm to 100 micrometers.

Furthermore, although the x-ray source 50/52/54 shown in FIGS. 5-8 is a transmission x-ray source (where the generated x-rays are taken from the opposite side of the incident electrons 111), a reflection type x-ray source (where the x-rays are taken from the same side of the incident electrons) may also be used (not shown). When the structured x-ray source is of a transmission type, the substrate thickness and the X-ray generating material need to be selected to have high transmission (e.g., >50%) of x-rays with the desired spectra.

Figure 9:
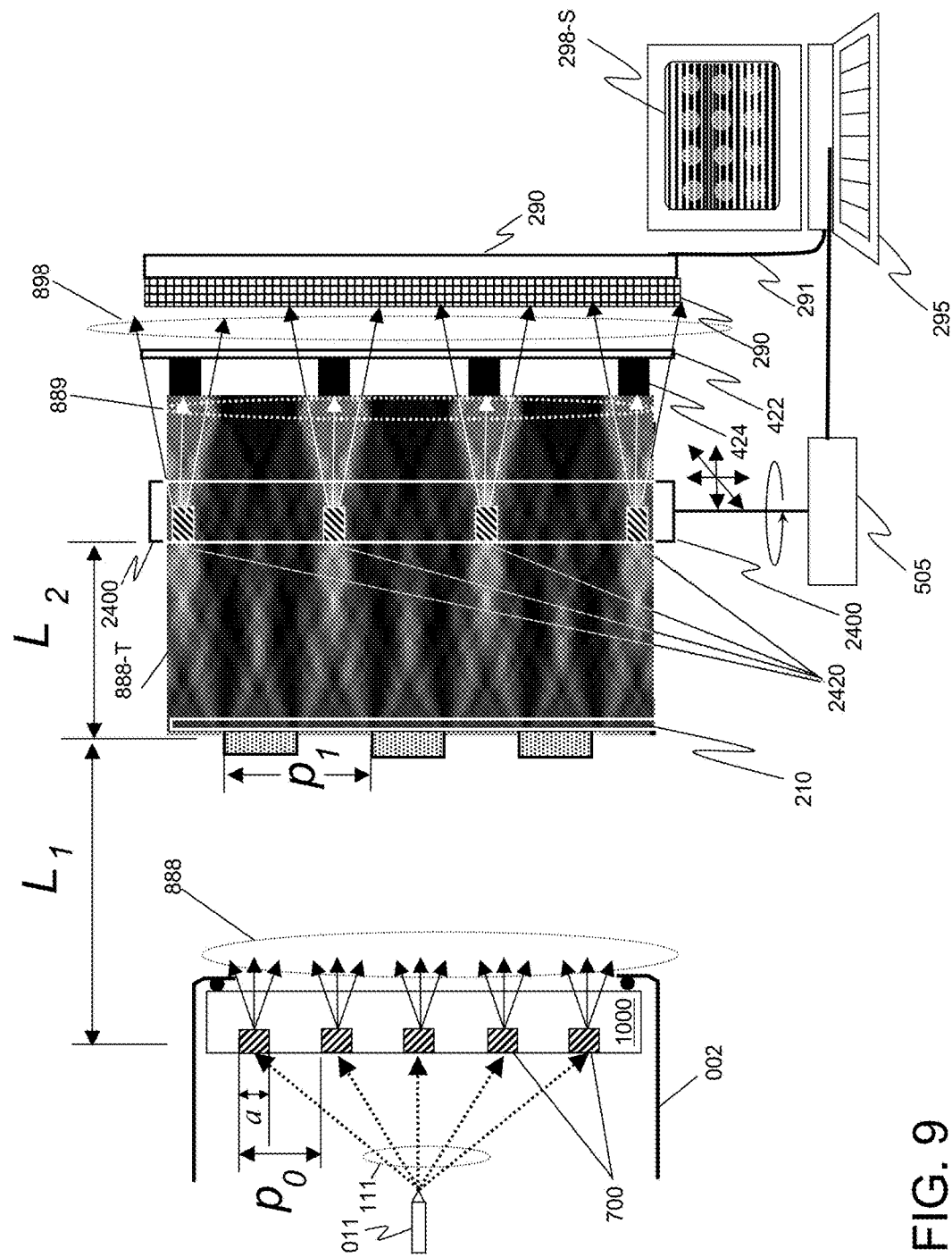
FIG. 9 presents a schematic cross-section illustration of a system according to the invention using a Talbot interference pattern to create structured illumination.

FIG. 9 illustrates an alternative embodiment to achieve structured illumination, as has been presented in more detail in the parent Application entitled "X-RAY METHOD FOR THE MEASUREMENT, CHARACTERIZATION, AND ANALYSIS OF PERIODIC STRUCTURES" (U.S. application Ser. No. 14/712,917, filed May 15, 2015). In this embodiment, structured illumination is achieved not by using an x-ray imaging system, but by using a periodic x-ray source matched to a phase grating to create a structured Talbot interference pattern. For the periodic microbeams of the disclosed apparatus in this illustration, small angle x-ray scattering (SAXS) information is obtained from regions or features of interest comprising periodic structures.

In this embodiment, coherent x-rays 888 from an x-ray source 002 having a target with microstructures 700 of dimension a and spaced at a period $p_0$ illuminate a phase grating 210 having a period $p_1$. An optional aperture or collimating system (e.g. one or more apertures or slits) may be placed before or after the phase grating 210. The x-rays 888 form a Talbot interference pattern 888-T after interacting with the grating 210. The object 2400 comprising periodic structures 2420 is aligned such that the structures 2420 of interest are coincident with the Talbot pattern anti-nodes, and produce small angle x-ray scattering, x-ray fluorescence, and/or diffraction signal(s). For small angle scattering, the scattered x-rays 889 are detected by a detector 290, which will typically be a position-sensitive type well known in the art. An optional beam stop 422 with regions 424 that absorb x-rays may be employed to block the detection of transmission of primary x-rays 889 that are not scattered.

For some embodiments of the system, small angle scattering of x-rays 898 up to 50 milliradians may be detected by the detector, while the beam stop 422 will block a range of angles from 0 radians to an angle dictated by the geometric arrangement of the system. For example, if the detector is 1 meter away from the object, and the overall illuminated area is 100 microns in diameter, then the beam stop will need to block from 0 milliradians to at least up to 0.1 milliradians, and possibly a larger number, to eliminate all directly transmitted (not scattered) x-rays. In some embodiments, the beam stop 422 is replaced with a single uniform beam stop placed close to the detector and is designed to stop directly transmitted x-rays.

In some embodiments, the object 2400 to be examined may be mounted on a mount, and rotated or translated by a stage, 5-axis mount 505, or goniometer.

It should be noted that these embodiments as illustrated are not to scale, as the divergence, collimation, or convergence of the Talbot interference pattern will depend on factors such as the X-ray energy, on how well collimated the x-ray beam is and how far the object is placed from the source.

Figure 10:
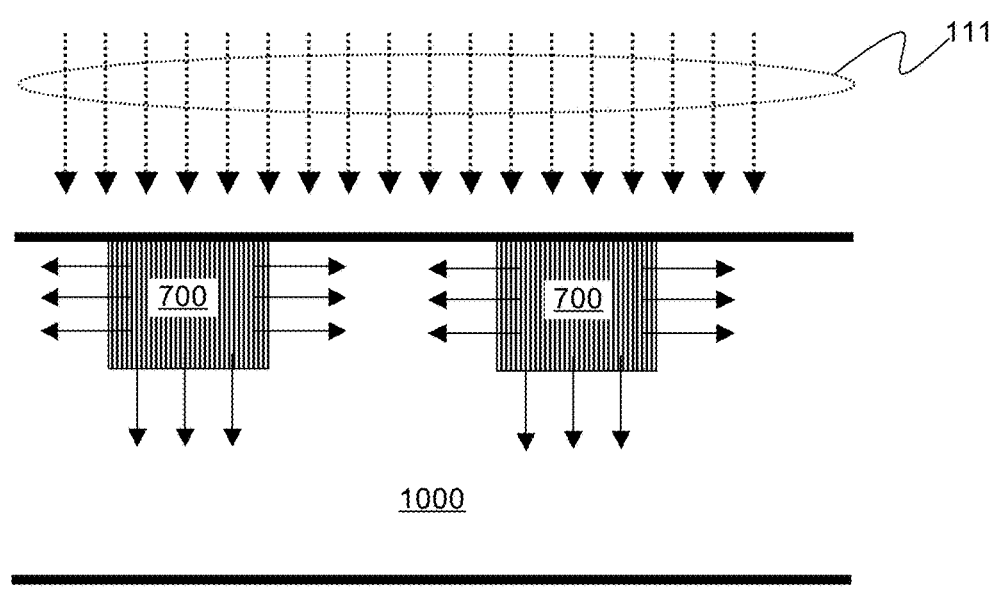
FIG. 10 illustrates a cross-section view of a portion of a structured target showing thermal transfer to a thermally conducting substrate under electron beam exposure.

FIG. 10 illustrates a particular advantage of certain embodiments of the invention in that high x-ray brightness and large x-ray power may be achieved by using an x-ray target in which microstructures 700 of a high Z material are in close thermal contact with, or embedded in, a substrate 1000 of low Z material and high thermal conductivity, such as beryllium or diamond. The ability of the substrate to draw heat away from the x-ray generating material allows higher electron density and power to be used, generating greater x-ray brightness and power from each of the microstructures of the x-ray generating material. This results in the creation of a structured x-ray source from the high Z material, while the use of a substrate with low Z and low mass density minimizes the production of x-rays from the substrate that can lead to a reduction in signal to noise ratio.

The heat transfer is illustrated with representative arrows in FIG. 10, in which the heat generated in microstructures 700 embedded in a substrate 1000 is conducted out of the microstructures 700 through the bottom and sides (arrows for transfer through the sides out of the plane of the drawing are not shown). The amount of heat transferred per unit time conducted through a material of area A and thickness d increases with the temperature gradient, the thermal conductivity in W/(m °C.), and the surface area through which heat is transferred. Embedding the microstructures in a substrate of high thermal conductivity increases all these factors.

1.2.3. X-Ray Detectors

Using the structured x-ray illumination system designed as described above, along with an x-ray detector(s) for the intended examination and selected from the available options for detectors known in the art, and electro-mechanical system for data acquisition and analysis known in the art, an x-ray system is constructed.

The detector may be any one of a number of detectors used for x-rays. X-ray detectors known in the art include x-ray spectrometers for x-ray fluorescence analysis, x-ray position sensitive (or array detector) for x-ray diffraction, small angle scattering, x-ray reflectivity, and absorption spectroscopy measurements. Position sensitive detectors include direct conversion solid state detectors and indirect conversion x-ray detectors that use a combination of scintillation/phosphor screen, an optical imaging transfer optic (such as an optical lens, fiber optic face plate), and a solid state imager (such as CCD or CMOS). Other detectors such as proportional counter or ionization chamber may also be used to measure x-ray intensity.

The x-ray detector may comprise a spectrometer that collects reflected x-rays as well as scattered or diffracted x-rays resulting from the interaction of the incident x-ray beam with the object. Depending on the measurement technique being employed, the detector may comprise x-ray optical elements and sensors designed to detect x-ray intensity and discriminate between x-ray energies. It may also in some embodiments be an x-ray detecting array designed to determine position dependent intensity for the x-rays emerging from the object.

The x-ray detector may comprise a photon counter, an energy dispersive detector such as a silicon drift detector or Si(Li) detector that can discriminate between the energies of the x-ray photons detected, a wavelength dispersive spectrometer, a micro-calorimeter, or an apparatus that comprises of a combination of one or more crystal or multilayer spectrometers and detectors to generate an electronic signal representing the number of counts for the x-rays at various energies, or some other set of elements that converts x-ray intensity into an electronic signal. The detector may also be an array x-ray detector that converts spatially dependent x-ray intensity to an electronic signal, including linear detectors, position-sensitive array detectors, pin diodes, proportional counters, spectrometers, etc.

One type of commonly used x-ray detector comprises a fluorescent screen or scintillator, such as one comprising a layer of cesium iodide (CsI), thallium doped CsI, yttrium aluminum garnet (YAG) or gadolinium sulfoxylate (GSO), that emits visible photons when exposed to x-rays. The visible photons are then detected by an electronic sensor that converts visible intensity into electronic signals, often with the additional formation of a relay image using visible optics that enlarge and magnify the intensity pattern of the photons emitted by the fluorescent screen. With the relay optics, the electronic detector need not comprise a high resolution sensor itself, and inexpensive commercial CCD detectors or complementary metal-oxide-semiconductor (CMOS) sensor arrays with, for example, 1024×1024 pixels, each 24 µm×24 µm square, may be used.

Commercial flat panel digital x-ray sensors in which a layer of scintillator material is placed in close proximity to (or even coated onto) an array of conventional optical image sensors are manufactured by, for example, Varian Inc. of Palo Alto, Calif. and General Electric, Inc. of Billerica, Mass. Other configurations of image sensors may be known to those skilled in the art. In embodiments in which an additional analyzer grating is used, it is preferable to use highly efficient, fast read-out detectors such as flat panel detectors, used for medical and industrial uses.

A second approach is to use an electronic sensor that directly creates an electrical signal in response to the absorption of x-rays, by, for example, the creation of direct electron-hole pairs in amorphous selenium (a-Se). These are then converted into electronic signals using an array of thin-film transistors (TFTs). Such direct flat panel detectors (FPDs) such as the Safire FPD of Shimadzu Corp. of Kyoto, Japan, are commercially available.

The system may also comprise one or more electro-mechanical system to align the x-ray source, imaging optic, detector, and the object with ROIs.

1.2.4. Additional Options

In some embodiments, a crystal monochromator may be included in the structured x-ray illumination beam to provide a narrow energy bandwidth. Alternatively, a thin film x-ray spectral filter of appropriate material known in the art may also be used to provide a narrow energy bandwidth.

The method may further comprise performing experiment(s) using the selected x-ray technique(s) and the x-ray system to collect data for the material properties and/or structures of the object intended for examination. The experiment may include a step to align the structured x-ray illumination beam with the ROI(s) in the object in position and angle to obtain optimal match using the electro-mechanical system of the x-ray system. The alignment step may be aided with an optical microscope, or by monitoring the x-ray signal intensity (such as fluorescence x-rays from one or more elements in the ROI(s), or x-ray absorption by the ROI(s)). The data collection and analysis may use any of several method(s) known in the art. For some applications, the relative position between the structured illumination beam and the ROI(s) may be scanned to obtain material or structure information for both the ROI(s) and for the surrounding areas of the ROI(s).

1.3. Advantages and Applications

There are several advantages of the disclosed method. These include the following.

Advantage 1: Increasing the signal and throughput when the illumination beam matches at least in part with the ROI(s) in shape and distribution (pattern) in an object for examination, including absorption, diffraction, small angle scattering, reflectivity and spectroscopy, permitting that the ensemble of signals from the multiple illumination regions be analyzed to determine various properties of the object and its structures.

Advantage 2: Minimizing or eliminating undesirable signal from regions outside the ROI(s), even if the ROI(s) have arbitrary shapes (such a rectangle, disk, cross, line) and/or arbitrary pattern(s) (such as periodic of features of substantially same shape, or aperiodic of arbitrary shape); and Advantage 3: For a periodic array of ROI(s) with substantially identical material properties or shapes to be examined, as many as one billion ROIs may be examined simultaneously, and a substantial throughput gain can be achieved. This can be especially useful for examining structures such as TSVs in silicon IC packaging, for which there may be as many as a billion copper structures embedded in a silicon wafer.

Applications to x-ray absorption/transmission, small angle x-ray scattering, x-ray fluorescence, x-ray reflectance, and x-ray diffraction are all possible using the method of the invention. One embodiment is to produce a periodic illumination beam with shape and pattern designed to match a fraction or whole of the periodic pattern and shape of substantially identical features on an object, such as transistors, interconnects, or through silicon vias on a semiconductor device or wafer.

2. Structured Target Considerations

Figure 11:
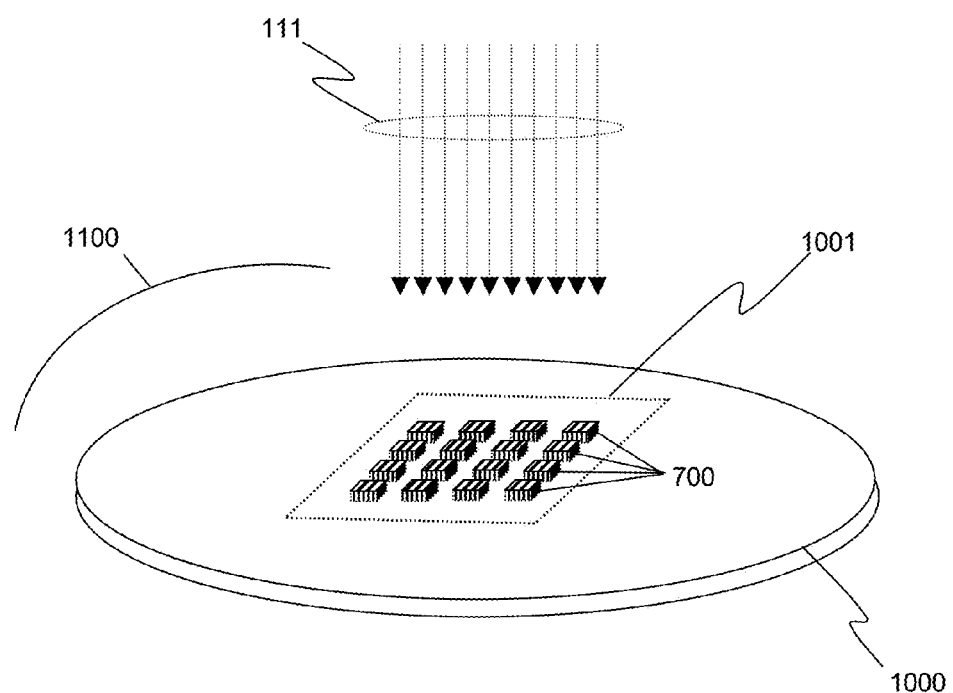
FIG. 11 illustrates a perspective view of a target comprising a grid of embedded rectangular target microstructures on a larger substrate that may be used in some embodiments of the invention.

FIG. 11 illustrates a structured target as may be used in some embodiments of the invention. In this figure, a substrate 1000 has a region 1001 comprising an array of microstructures 700 of x-ray generating material (typically a metallic material) that are arranged as a regular array of right rectangular prisms. (Note: although only 16 x-ray generating elements are illustrated, targets with many more x-ray generating elements, or only a few x-ray generating elements, may be designed, depending on the size, shape, and number of ROI(s) in the object to be examined.)

In a vacuum, electrons 111 bombard the target from above, and generate heat and x-rays in the microstructures 700. The material in the substrate 1000 is selected such that it has relatively low x-ray production (efficiency is proportional to atomic number) and energy deposition rate (stopping power is proportional to density) for electrons in comparison to the x-ray generating microstructure material, and therefore will not generate a significant amount of heat and x-rays. This is typically achieved by selecting a low mass density and low atomic number (Z) material for the substrate.

The substrate 1000 material may also be chosen to have a high thermal conductivity, typically larger than 100 W/(m ° C.), and the microstructures are typically embedded within the substrate, i.e. if the microstructures are shaped as rectangular prisms, it is preferred that at least five of the six sides are in close thermal contact with the substrate 1000, so that heat generated in the microstructures 700 is effectively conducted away into the substrate 1000. However, targets used in other embodiments may have fewer direct contact surfaces.

Table I lists several materials that are commonly used for x-ray targets, several additional potential target materials (notably useful for specific characteristic lines of interest), and some materials that may be used as substrates for target materials. Melting points, and thermal and electrical conductivities are presented for values near 300° K (27° C.). Most values are taken from the *CRC Handbook of Chemistry and Physics*, 90$^{th}$ ed. [CRC Press, Boca Raton, Fla., 2009]. Other values are taken from various other references.

TABLE I

Various Target and Substrate Materials and Selected Properties.

| Material (Elemental Symbol) | Atomic Number Z | Melting Point ° C. (1 atm) | Thermal Conductivity (W/(m ° C.)) | Electrical Conductivity (MS/m) |
|---|---|---|---|---|
| Common Target Materials: | | | | |
| Chromium (Cr) | 24 | 1907 | 93.7 | 7.9 |
| Iron (Fe) | 26 | 1538 | 80.2 | 10.0 |
| Cobalt (Co) | 27 | 1495 | 100 | 17.9 |
| Copper (Cu) | 29 | 1085 | 401 | 58.0 |
| Molybdenum (Mo) | 42 | 2623 | 138 | 18.1 |
| Silver (Ag) | 47 | 962 | 429 | 61.4 |
| Tungsten (W) | 74 | 3422 | 174 | 18.4 |
| Potential Substrate Materials with low atomic number: | | | | |
| Beryllium (Be) | 4 | 1287 | 200 | 26.6 |
| Carbon (C): Diamond | 6 | * | 2300 | $10^{-19}$ |
| Carbon (C): Graphite (in plane) | 6 | * | 1950 | 0.25 |
| Boron Nitride (BN) | B = 5, N = 7 | ** | 20 | $10^{-17}$ |
| Silicon (Si) | 14 | 1414 | 124 | $1.56 \times 10^{-9}$ |
| Silicon Carbide (β-SiC) | Si = 14, C = 6 | 2798 | 0.49 | $10^{-9}$ |
| Sapphire ($Al_2O_3$) (∥ C-axis) | Al = 13, O = 8 | 2053 | 32.5 | $10^{-20}$ |

\* Carbon does not melt at 1 atm; it sublimes at ~3600° C.
\*\* BN does not melt at 1 atm; it sublimes at ~2973° C.

The depth of penetration of electrons into the material can be estimated by Potts' Law [P. J. Potts, Electron Probe Microanalysis, Ch. 10 of *A Handbook of Silicate Rock Analysis*, Springer Netherlands, 1987, p. 336)], which states that the penetration depth x in microns is related to the 10% of the value of the electron energy $E_0$ in keV raised to the 3/2 power, divided by the density of the material:

$$x \ (\mu m) = 0.1 \times \frac{E_0^{1.5}}{\rho} \qquad \text{[Eqn. 1]}$$

Using this formula, Table II illustrates some of the estimated penetration depths for some common x-ray target materials.

TABLE II

Estimates of penetration depth for 60 keV electrons into some materials.

| Material | Z | Density (g/cm³) | Penetration Depth (μm) |
|---|---|---|---|
| Diamond | 6 | 3.5 | 13.28 |
| Copper | 29 | 8.96 | 5.19 |
| Molybdenum | 42 | 10.28 | 4.52 |
| Tungsten | 74 | 19.25 | 2.41 |

For less dense material, such as a diamond substrate, the penetration depth is much larger than for a material with greater density, such as most materials containing elements used for x-ray generation.

The majority of characteristic Cu K x-rays are generated within the penetration depth. The electron interactions below that depth typically generate few characteristic K-line x-rays but will contribute to the heat generation, thus resulting in a low thermal gradient along the depth direction. It is therefore preferable in some embodiments to set a maximum thickness for the microstructures in the target in order to limit electron interaction in the material and optimize local thermal gradients. One embodiment of the invention limits the depth of the microstructured x-ray generating material in the target to between one third and two thirds of the electron penetration depth in the substrate at the incident electron energy. In this case, the lower mass density of the substrate leads to a lower energy deposition rate in the substrate material immediately below the x-ray generating material, which in turn leads to a lower temperature in the substrate material below. This results in a higher thermal gradient between the x-ray generating material and the substrate, enhancing heat transfer. The thermal gradient is further enhanced by the high thermal conductivity of the substrate material.

For similar reasons, selecting the thickness of the microstructures to be less than one half of the electron penetration depth in the substrate is also generally preferred for efficient generation of bremsstrahlung radiation, because the electrons below that depth have lower x-ray production efficiency. Note: Other choices for the dimensions of the x-ray generating material may also be used. In targets as used in some embodiments of the invention, the depth of the x-ray material may be selected to be 50% of the electron penetration depth in the substrate. In other embodiments, the depth of the x-ray material may be selected to be 33% of the electron penetration depth in the substrate. In other embodiments, the depth for the microstructures may be selected related to the "continuous slowing down approximation" (CSDA) range for electrons in the material. Other depths may be specified depending on the x-ray spectrum desired and the properties of the selected x-ray material.

Figure 12A:
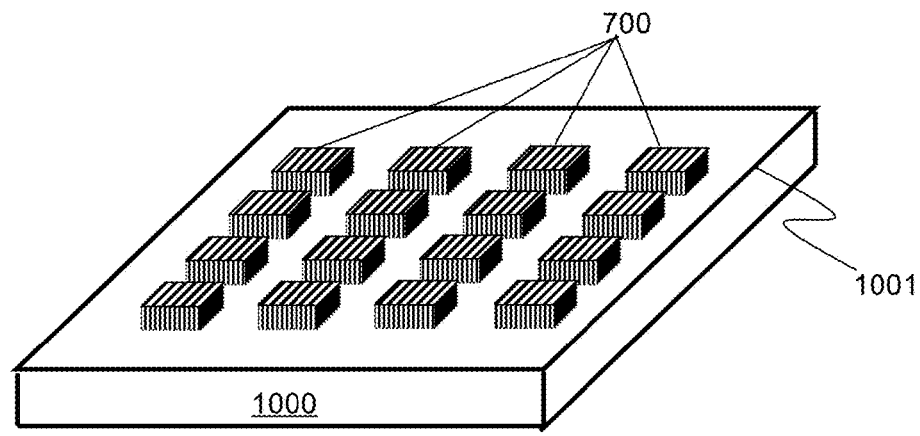
FIG. 12A illustrates a perspective view of a target comprising a grid of embedded rectangular target microstructures that may be used in some embodiments of the invention.
Figure 12B:
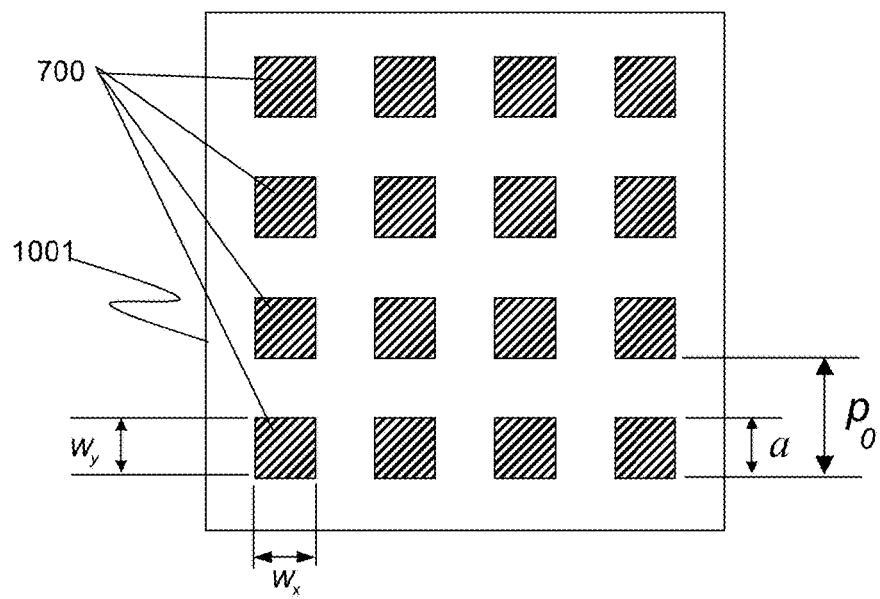
FIG. 12B illustrates a top view of the target of FIG. 12A.
Figure 12C:
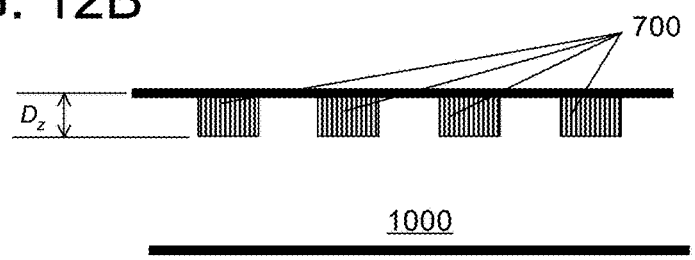
FIG. 12C illustrates a side/cross-section view of the target of FIGS. 12A and 12B.

FIGS. 12A-12C illustrate a region 1001 of a target as may be used in some embodiments of the invention that comprises an array of sub-sources 700 with microstructures in the form of right rectangular prisms comprising x-ray generating material arranged in a regular array. FIG. 12A presents a perspective view of the sixteen microstructures 700 for this target, while FIG. 12B illustrates a top down view of the same region, and FIG. 12C presents a side/cross-section view of the same region. (For the term "side/cross-section view" in this disclosure, the view meant is one as if a cross-section of the object had been made, and then viewed from the side towards the cross-sectioned surface. This shows both detail at the point of the cross-section as well as material deeper inside that might be seen from the side, assuming the substrate itself were transparent [which, in the case of diamond, is generally true for visible light].)

In these targets, the microstructures have been fabricated such that they are in close thermal contact on five of six sides with the substrate. As illustrated, the top of the microstructures 700 are flush with the surface of the substrate, but other targets in which the microstructure is recessed may be fabricated, and still other targets in which the microstructures present a topographical "bump" relative to the surface of the substrate may also be fabricated.

An alternative target as may be used in some embodiments of the invention may have several microstructures of right rectangular prisms simply deposited upon the surface of the substrate. In this case, only the bottom base of the prism would be in thermal contact with the substrate.

Figure 13A:
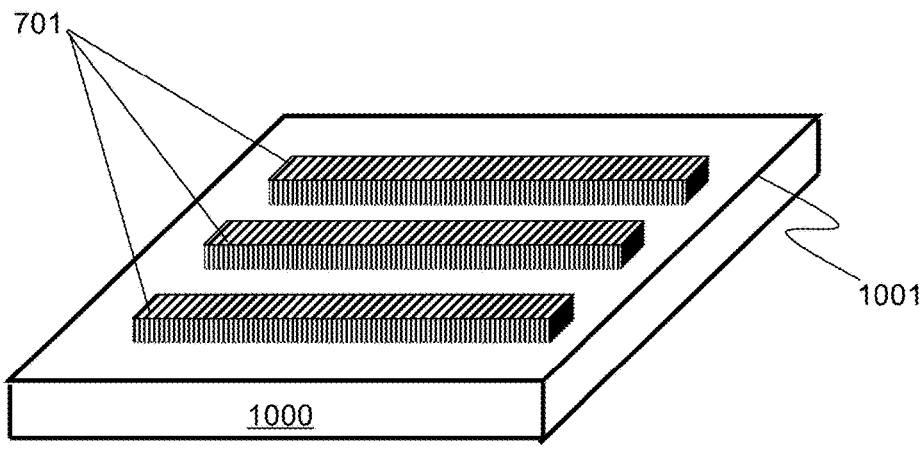
FIG. 13A illustrates a perspective view of a target comprising a set of embedded rectangular target microstructures that may be used in some embodiments of the invention.
Figure 13B:
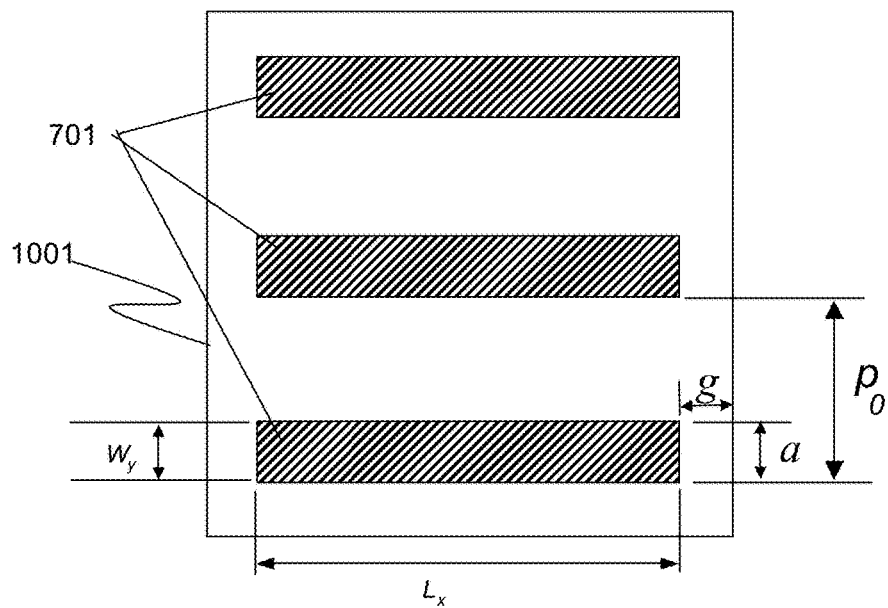
FIG. 13B illustrates a top view of the target of FIG. 13A.
Figure 13C:
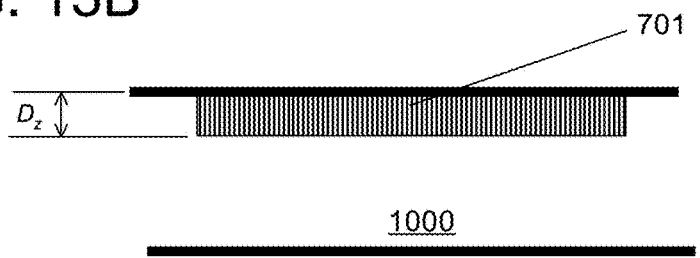
FIG. 13C illustrates a side/cross-section view of the target of FIGS. 13A and 13B.

FIGS. 13A-13C illustrate a region 1001 of a target as may be used in some embodiments of the invention that comprises an array of linear sub-sources 701 with microstructures in the form of right rectangular prisms comprising x-ray generating material arranged in a regular array. FIG. 13A presents a perspective view of the three microstructures 701 for this target, while FIG. 13B illustrates a top down view of the same region, and FIG. 13C presents a side/cross-section view of the same region.

Figure 14:
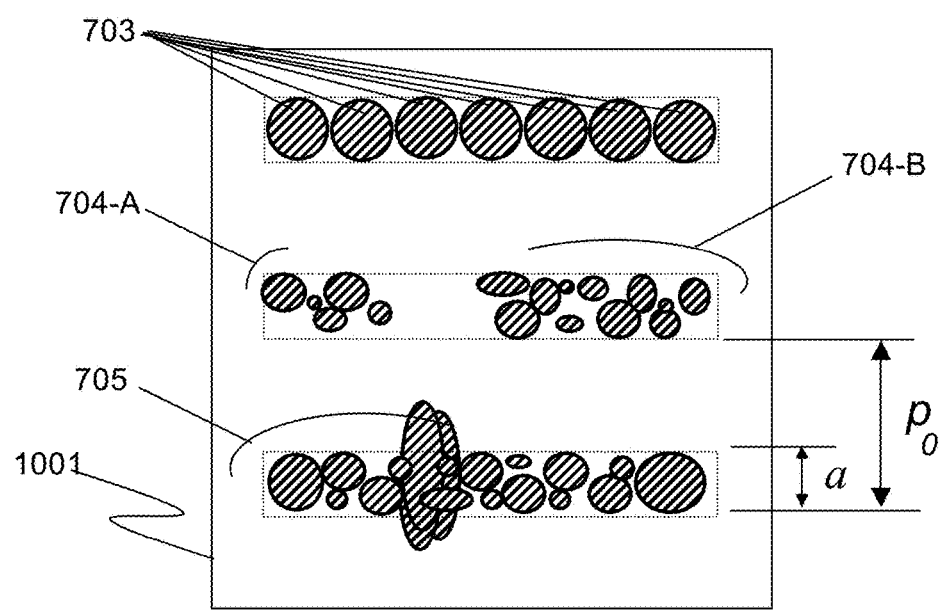
FIG. 14 illustrates a top view of a target in which irregular x-ray materials have been deposited in a quasi-periodic pattern.

FIG. 14 illustrates a practical issue that may arise in forming the targets such as those illustrated in FIGS. 12A-13C. FIG. 14 shows examples of ensemble microstructures as may occur when fabricating linear microstructures 701, particularly if the x-ray generating material is deposited as a powder. If uniform pre-fabricated particles of x-ray generating material are created and coated onto the substrate, an ensemble of particles 703 of x-ray generating material may be formed. In other processes, if non-uniform particles are used, clusters of particles 704-A and 704-B may form, in some cases with a non-uniform distribution that may include gaps of voids. In other processes, an ensemble of particles 704 of x-ray generating material may approximate a line source of x-rays.

Targets comprising microstructures such as those that may be used in x-ray sources according to the invention disclosed herein have been described in detail in the co-pending U.S. patent application entitled STRUCTURED TARGETS FOR X-RAY GENERATION (U.S. patent application Ser. No. 14/465,816, filed Aug. 21, 2014), which is hereby incorporated by reference in its entirety, along with the provisional applications to which this co-pending Application claims benefit. Any of the target designs and configurations disclosed in the above referenced co-pending Application may be considered for use as a component in any or all of the x-ray methods and systems disclosed herein.

Additional target and x-ray source configurations as may be used in embodiments of the present invention are described more fully in the co-pending U.S. patent applications X-RAY SOURCES USING LINEAR ACCUMULATION (U.S. patent application Ser. No. 14/490,672 filed Sep. 19, 2014) and DIVERGING X-RAY SOURCES USING LINEAR ACCUMULATION (U.S. patent application Ser. No. 15/166,274 filed May 27, 2016), both of which are hereby incorporated by reference in their entirety, along with the provisional Applications to which these co-pending Applications claim benefit. Any of the source designs and configurations disclosed in the above referenced co-pending Application may be considered for use as a component in any or all of the methods or systems disclosed herein.

Although FIGS. 7-14 show targets with x-ray generating materials having regular patterns and shapes, for embodiments of the invention the shape(s), size, and number of the x-ray generating regions need to be designed to correspond to the pattern and shapes of the ROI(s) to be examined and the magnification of the imaging system design to be used (Note: the magnification refers to the ratio of the image to the source, and can be less than one).

In some embodiments, an electrically conductive path is included in fabrication of the microstructures in the substrate, especially when the substrate is an electrical insulator, such as diamond. In some embodiments, an adhesion and/or diffusion between the x-ray generating materials and the substrate may be used. Overcoats of various materials and dimensions may also be provided for electrical conductivity, thermal conductivity, chemical isolation or encapsulation, or other functions desired for particular target designs.

The target may be cooled to enhance the thermal performance by those skilled in the art, in which the substrate may, for example, be bonded to a heat sink, such as a copper block, for improved thermal transfer. The copper block may in turn have cooling channels within it to assist in carrying heat away from the block. Alternatively, the substrate may be attached to a thermoelectric cooler, in which a voltage is applied to a specially constructed semiconductor device. Heat pipes containing a heat transfer fluid that evaporates and condenses, as are used for cooling CPU chips in server farms when compact design is a consideration, may also be used to cool the substrate.

Alternatively, the substrate can be attached to a cryogenic cooler, such as a block containing channels for the flow of liquid nitrogen, or be in thermal contact with a reservoir of liquid nitrogen or some other cryogenic substance, such as an antifreeze solution, to provide more extreme cooling. When the substrate comprises a material such as diamond, sapphire, silicon, or silicon carbide, thermal conductivity generally increases with decreasing temperature from room temperature. In such a case, designing the target so that it can withstand cooling to these lower temperatures may be preferred.

3. X-Ray Optical System Considerations

For embodiments of the invention disclosed here, the x-ray source may be imaged onto the object using a system of one or more x-ray imaging optics. The x-ray imaging optics may comprise a zone plate, a Wolter mirror optic, or a compound refractive lens. The x-ray imaging optics are configured and aligned to image the x-ray source on the ROI(s) of the object.

Transmission type X-ray zone plates may be used as the x-ray imaging optic 1020 in FIGS. 5-8. A phase zone plate is generally preferred due to its high diffraction efficiency. Zone plates can be fabricated using various lithographic techniques or sputter/slicing techniques by those skilled in the art. Because zone plates with imaging resolution down to 10 nm have been demonstrated, they are preferred as the x-ray imaging optic when the structure illumination beam requires fine cross section shape(s), especially for sub-100 nm shape(s). Additionally, a zone plate also can be considered as an ideal thin lens, and has very low image distortion for reasonably large field of view.

Because zone plate is chromatic, the x-ray beam needs to have adequately narrow energy bandwidth. To achieve this, a crystal or multilayer monochromator may be used in the x-ray beam path between the structured x-ray source and the object. Alternatively, a thin film spectral filter may also be used.

Figure 15:
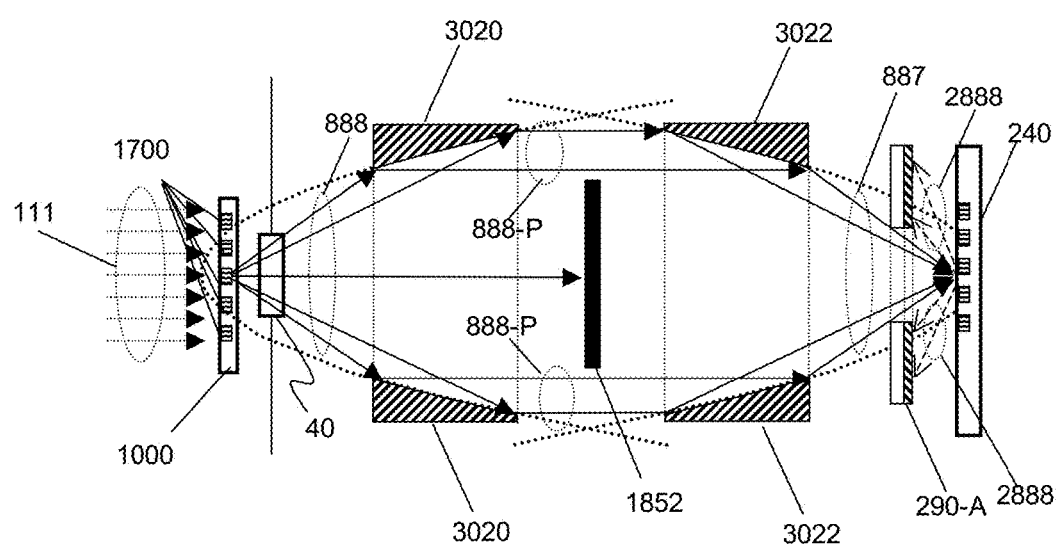
FIG. 15 illustrates a schematic cross-section view of an x-ray source and x-ray optical system comprising parabolic optical elements as may be used in some embodiments of the invention.
Figure 16:
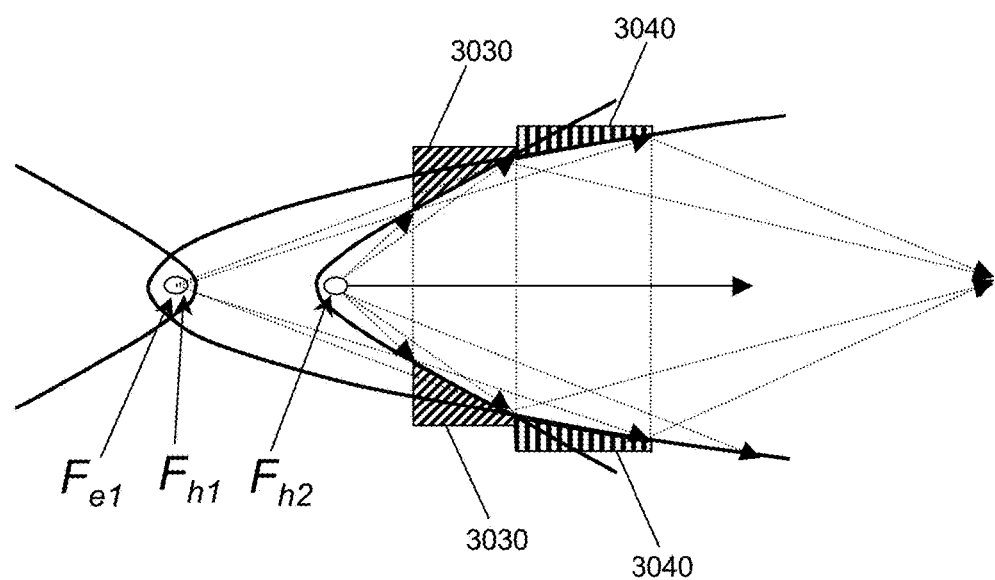
FIG. 16 illustrates a schematic cross-section view of an x-ray Wolter optical element as may be used in some embodiments of the invention.

Alternatively, reflective x-ray optics or combinations thereof may be used as the x-ray imaging optic in FIGS. 5-8. In general, a Wolter mirror optic offers much higher focusing efficiency than zone plates. FIGS. 15 and 16 illustrate two designs of x-ray optical systems incorporating reflective x-ray mirror optics that may be used in some embodiments of the invention.

FIG. 15 shows a cross section schematic view of a set of reflective x-ray mirror optics comprising two paraboloidal reflectors 3020 and 3022. A structured x-ray source comprising x-ray generating microstructures 1700 embedded in a substrate 1000 generate x-rays 888 when bombarded by electrons 111 in a vacuum. The x-rays 888 pass through a vacuum chamber window 40 as a diverging source. A portion of the x-rays experience total external reflection from the inner surface of the first paraboloidal reflector 3020, which is positioned so that its focus is at the plane of the microstructures 1700 of the structured x-ray source. This creates a collimated x-ray beam 888-P with an annular profile. In some embodiments, a beam stop 1852 may also be used.

The second paraboloidal reflector 3022 with a tube-shaped topology and parabolic inner surface may be aligned with the optical axis of the first optical element 3020 so that the collimated x-rays 888-P are incident on the inner surface of the second optical element 3022 at angles smaller than the critical angle for the surface. The reflected x-rays 889 form an image of the source at the focal plane of the second reflector 3022. Placing an object 240 to be examined at this focus allows x-ray signal (e.g., x-ray fluorescence 2888 schematically shown) to be generated, which is then collected on a detector 290-A. (Note: although a system for collecting an x-ray fluorescence signal is shown, other x-ray signals can be collected with x-ray detector(s) that are suitable for the intended examination and properly positioned by those skilled in the art.)

FIG. 16 illustrates a general configuration of type I Wolter mirror optic comprising an ellipsoid combined with a hyperboloid [see H. Wolter, Spiegelsysteme streifenden Einfalls als abbildende Optiken für Röntgenstrahlen, Annalen der Physik, vol. 10 (1952), pp. 94-114]. The two geometric forms are aligned so one of the foci of the ellipse $F_{e1}$ corresponds to one of the foci of the hyperbola $F_{h1}$. X-rays emitted at the other focus of the hyperbola $F_{h2}$ will reflect off a first optical element 3030 corresponding to a hyperboloid; the x-ray beam path for the initially reflected x-rays will then reflect from a second optical element 3040 corresponding to the surface of the ellipse. With a proper design and selection of the geometric parameters, the type I Wolter mirror optic can image a structured x-ray source (not shown) on to an image plane with a predetermined image magnification such that the x-ray image matches at least a fraction of the ROI(s) to be examined. In designing the optical system, it is important that the angle of incidence for the x-rays is smaller than the critical angle (critical angles may be made larger through use of a coating for the reflecting portions), to achieve total external reflection.

Other x-ray optical systems that may be used to form x-ray images in embodiments of this invention have been described in the co-pending U.S. patent application entitled X-RAY ILLUMINATORS WITH HIGH FLUX AND HIGH FLUX DENSITY by the inventors of the present invention (U.S. patent application Ser. No. 14/544,191 filed Dec. 5, 2014), which is hereby incorporated by reference in its entirety, along with the provisional Applications to which it claims priority.

Note: The illustrations in the Drawings disclosed in this Application are typically not shown to scale, and are meant to illustrate the principle of the invention and its function only. Reflective x-ray optics typically have an acceptance angle of only a few degrees, and not the ≈30° as shown for illustrative purposes in the various figures.

4. Applications to Semiconductor Metrology and Inspection

The method and the apparatus described above can be designed to characterize, analyze, and measure predetermined ROI(s) of an object with substantial performance advantages compared with conventional x-ray techniques and systems which have thus far relied on an unstructured illumination beam (either large or focused beam with respect to the ROI(s)) in terms of signal-to-noise ratio and throughput (data analysis speed). When illuminated by an illumination beam larger than the ROI(s), x-ray signal from the surrounding region(s) of the ROI(s) may contribute to the detected signal as background and reduce signal-to-noise ratio of the information arising from the ROI(s). When an x-ray beam is focused on a single feature, information about that particular ROI(s) may be gathered, but given that there may be millions of ROIs in an object, determination of the statistical properties of the multiple ROIs with data taken serially will take an inordinate amount of time and is very inefficient. Metrology, inspection, and characterization of ROI(s) with periodic structures, such as many components in integrated semiconductor devices, including transistors, interconnects, and through silicon vias (TSVs), can benefit substantially using the method and apparatus disclosed.

Figure 17:
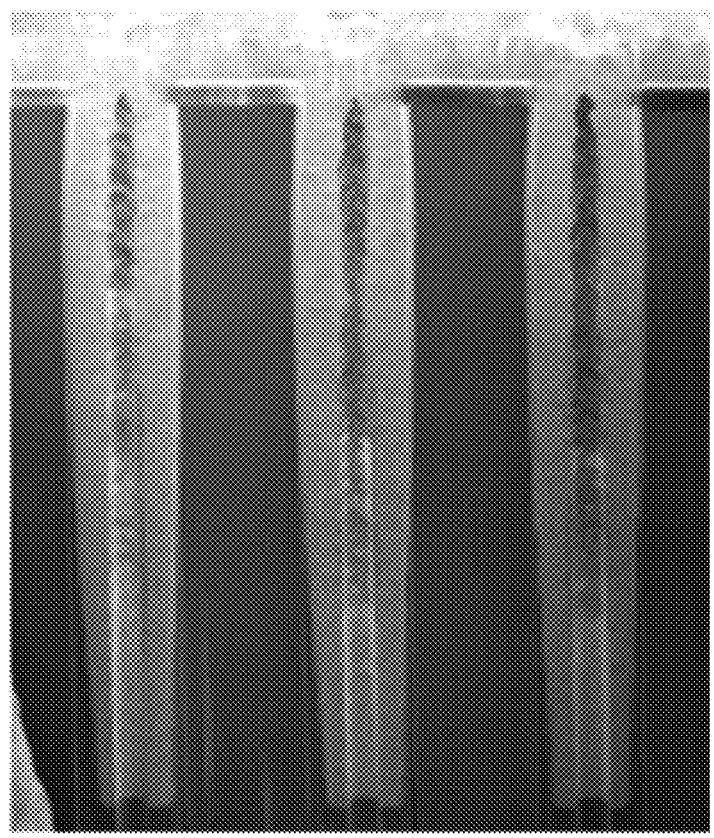
FIG. 17 illustrates a published SEM micrograph of a periodic object (defective TSVs in a silicon wafer) that may be examined using the methods of the invention.

For example, the method and the apparatus described above can be used for metrology and inspection of multiple of TSVs using small angle x-ray scattering technique to detect and measure fine voids with at least one dimension less than 100 nm, or using x-ray absorption and/or x-ray fluorescence analysis techniques to measure larger voids with dimension larger than 100 nm. FIG. 17 illustrates an example of periodic structures in an object (an IC or silicon wafer) that may be examined using the methods of the invention disclosed herein. This illustration (published in Victor Vartanian et al., "Metrology needs for through silicon via fabrication", in J. Micro/Nanolith. MEMS MOEMS 13(1), 011206 (January-March 2014), FIG. 6) shows a cross section of copper through silicon vias (TSVs) that have been fabricated with unwanted voids in the center of the TSV. Detecting when a TSV fabrication process is producing voids is an important application for the techniques disclosed here.

Figure 18A:
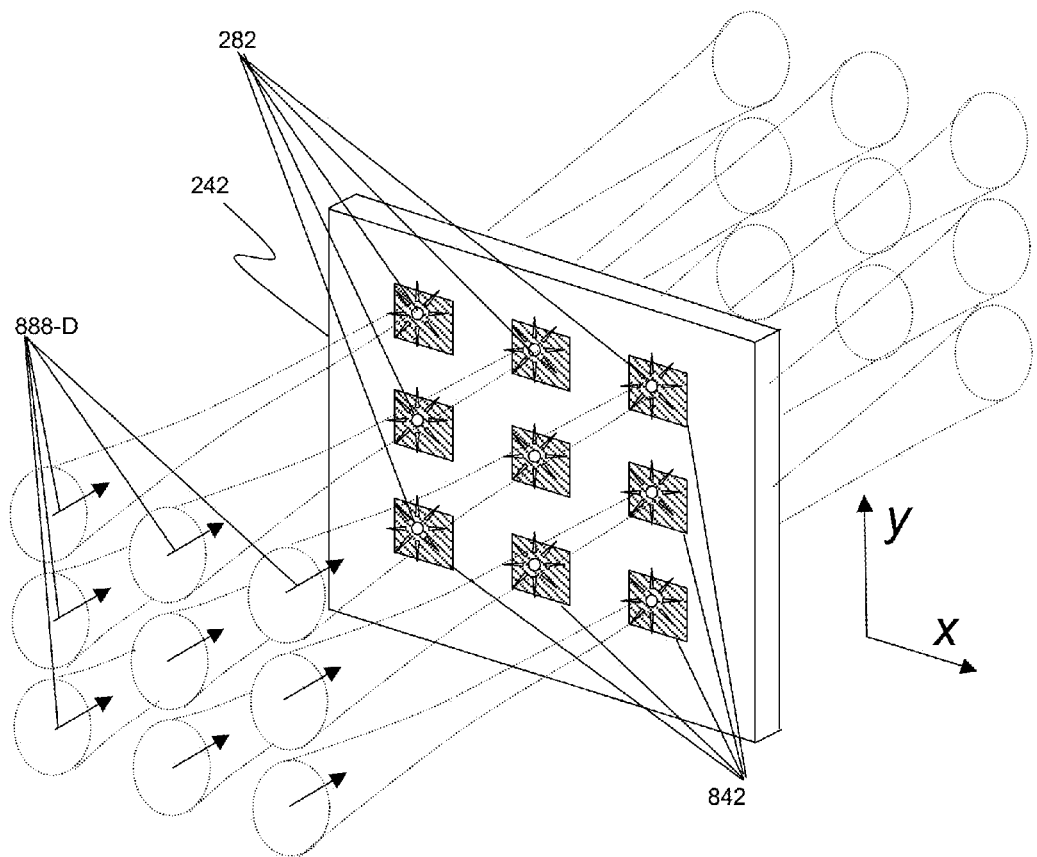
FIG. 18A illustrates a schematic diagram of an x-ray measurement system according to the invention as may be used for periodic structures.
Figure 18B:
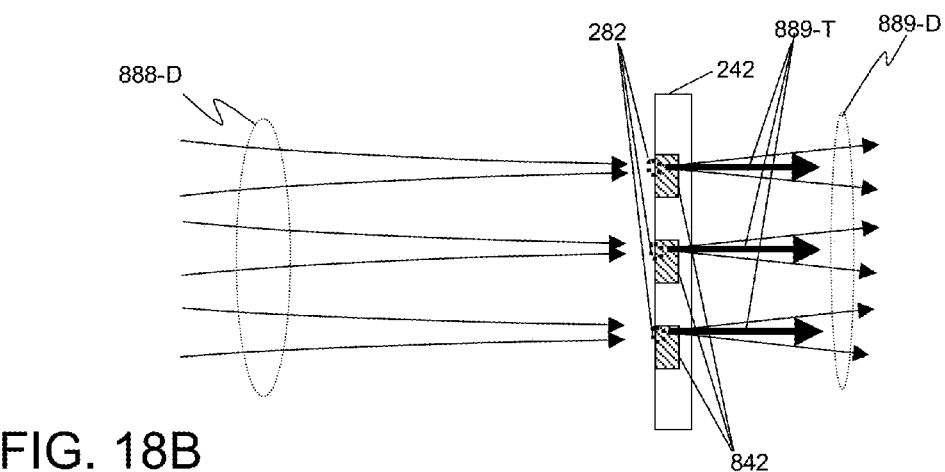
FIG. 18B illustrates a cross-section diagram of the x-ray measurement system of FIG. 18A.

For periodic structures, a variation on the methods previously described may be used in some embodiments of the invention. This is illustrated in FIGS. 18A and 18B. In the embodiment shown, aligned for measuring small-angle x-ray scattering, the x-ray beam profile 888-D converges to a plurality of spots 282 in a periodic array that corresponds to the periodic structures 242. As illustrated, a single spot is formed in each single structure 242, but other embodiments in which, for example, a spot is formed in every other structure, or only a subset of the structures 242, may also be configured. As illustrated, the scattered x-rays 899-D are distinct from the transmitted x-rays 889-T, and a detector with the appropriate beam stops, as was, for example, illustrated in FIG. 9, will produce a detector signal.

As long as the periodic structures have been designed to be a spatially repeating pattern, and as long as the corresponding beams for each of the repeating units are aligned to illuminate corresponding positions of the periodic structures, the signal will be amplified by the number of structures sampled by the beams. Therefore, if 100 objects can be illuminated by 100 beams, the signal will be 100 times stronger than that produced by a single beams on a single object.

This is especially well suited for the examination of objects such as integrated circuits, where large two-dimensional arrays of millions or even billions of nominally identical structures, such as the TSV structures illustrated in FIG. 17, are arranged on planar surfaces. Although the example of FIG. 18A-18B shows the use of small-angle x-ray scattering (SAXS), any one of a number of x-ray metrology techniques (x-ray fluorescence, x-ray diffraction, etc.) may be used.

Figure 19A:
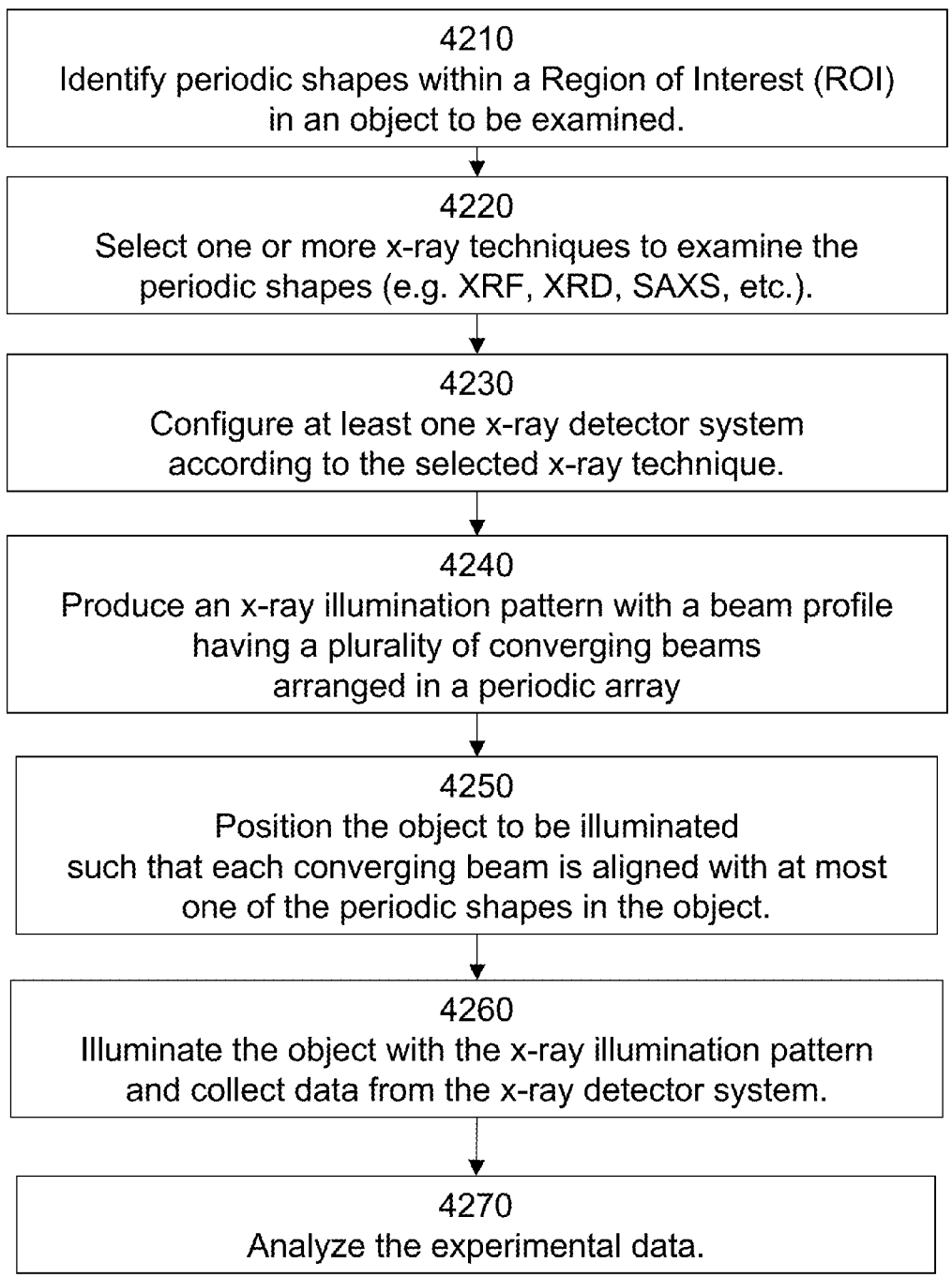
FIG. 19A presents a flow diagram for a method of x-ray measurement according to the invention as may be used for periodic structures.
Figure 19B:
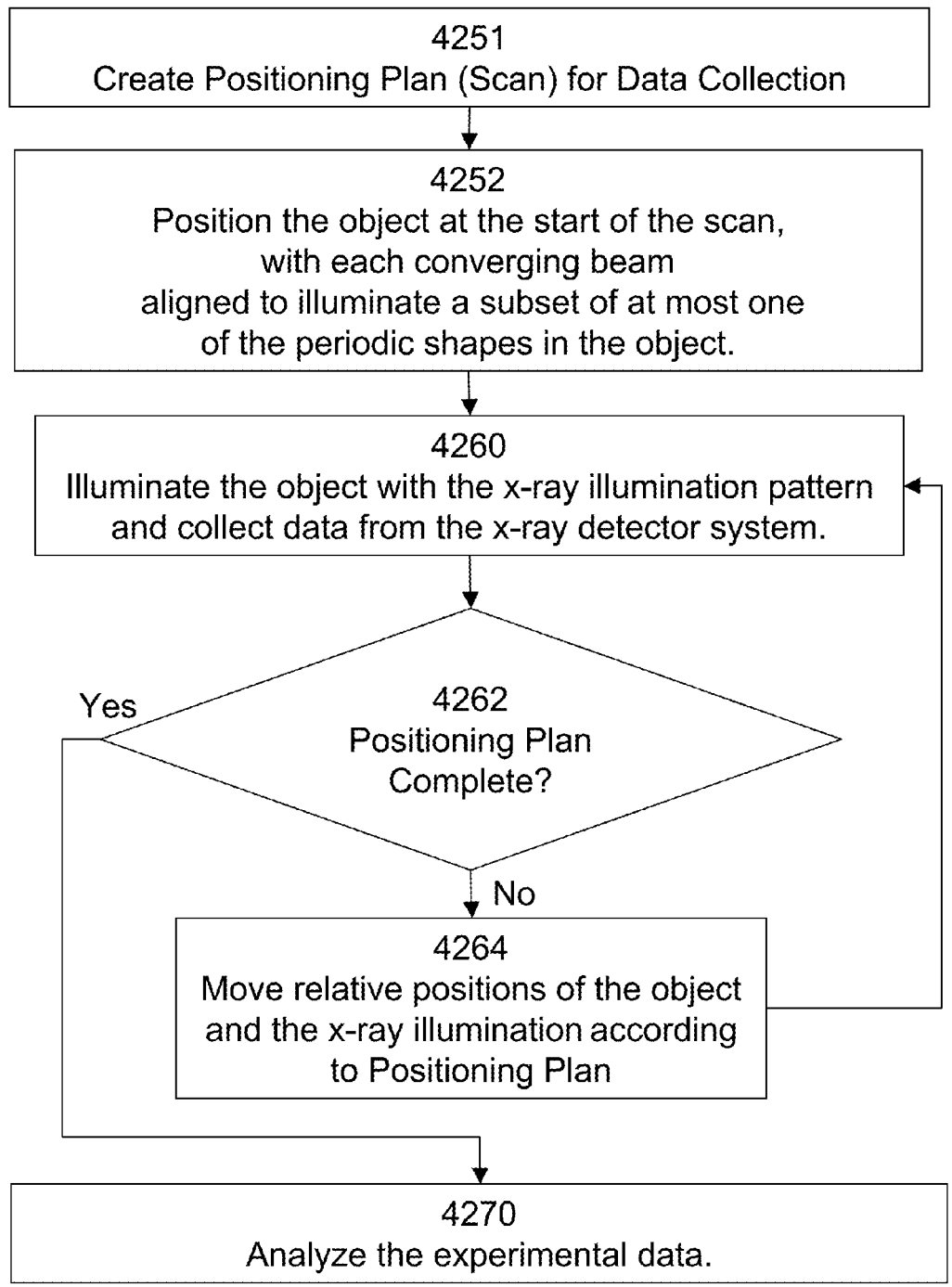
FIG. 19B presents a flow diagram for a sub-set of a method of x-ray measurement according to the invention as may be used for periodic structures.

The method used to execute this kind of parallel ensemble sampling will be somewhat modified from the more generic method presented in FIG. 4, and is presented in FIGS. 19A-19B. The first 4210 and second 4220 steps are similar to the corresponding steps of FIG. 4, but now comprise the identification of periodic shapes or structures.

The next step 4230 is the same as the 3rd step in the previous method—the x-ray detector suitable for the selected method is configured.

The following step 4240 comprises producing an x-ray illumination pattern having a plurality of converging x-ray beams, nominally of similar size, shape and intensity and corresponding to, or matched identically with, the periodic structures of the object to be examined.

The next step 4250 comprises aligning the plurality of beams with the periodic structures. To allow the signal to represent an ensemble of structures, any given one of the periodic structures should interact with only a single x-ray beam, with the x-ray beam positions illuminating corresponding positions in their respective structures.

In the following step 4260, the periodic structures are illuminated with the array of x-ray beams, and the signals collected from the detector.

Once data has been collected, the final step 4270 of the method comprises analyzing the collected data.

As described above, a single beam illuminates a single structure, and applying the descriptions used for some of the previously described embodiments, in some embodiments, the shape of the beam may be designed to correspond to the entire structure.

However, as was illustrated in FIG. 17, some objects have internal variations that may be of interest to detect. For these situations, a modification to the method as illustrated in FIG. 19B may be used.

In this embodiment, the initial steps 4210, 4220, 4230 and 4240 are the same as in FIG. 19A. However, instead of step 4250, this embodiment anticipates having x-ray beams that are significantly smaller than the structures, and anticipates scanning over the structure to produce a "map" of the properties as a function of x-y position.

Therefore, instead of step 4250, the next step 4251 is the creation of a positioning plan for the locations in the object to be measured. For some embodiments, this may be in the form of a raster scan over the structure. For other embodiments, this may be a set of measurements at discrete positions. In other embodiments, the focused spot for the x-ray beam may be asymmetric, e.g. in the form of a vertical bar, and the x-ray beam is therefore scanned relative to the object only in the x direction.

In the next step 4252, the object is positioned as dictated by initial position at the start of the sampling plan.

In the next step 4260, the object is illuminated with x-rays and the data collected from that particular position in the sampling plan.

In the next step 4262, a determination is made if the sampling plan has been completed. If not, in the next step 4264, the relative positions of the object and the x-ray beams are adjusted according to the sampling plan, and the method loops back to illuminate the object in the new location, and data for the new location is collected according to step 4260.

Only once the sampling plan is completed does step 4262 give an answer of "Yes", and the methods moves on to the next step 4270, the analysis of experimental data.

This scanning approach may be especially useful for determining the profile of, for example, the TSVs of FIG. 17, which have voids in their center. By scanning across an ensemble of TSVs, the contrast between the surrounding material, the side of the TSV, and the core of the TSV may be determined with both a strong signal and a good signal-to-noise ratio.

In some embodiments, the structured illumination beam may be configured and aligned such that a major fraction of incident x-rays only illuminate the central part of the TSVs and with little of a negligible fraction of the incident x-ray beam illuminate the regions outside the TSVs. This is particularly important when small angle x-ray scattering technique is used to measure the fine voids because it reduces or eliminates x-rays scattered by the sharp interfaces around the TSVs. X-ray fluorescence analysis technique may also be used to measure side diffusion barrier or electroplating seed layers of multiple of etched TSV holes before electroplating. Small angle x-ray scattering may also be used to characterize surface roughness of the side walls of the etched TSV holes. X-ray diffraction technique may also be used to measure strain surrounding multiple TSVs by measuring diffracted x-rays while the structured x-ray illumination beam is aligned to a point or points of interest for measurement.

The method and the apparatus described above may be used for determining or monitoring the 3D structure of semiconductor structures on a semiconductor wafer during manufacturing process, including etched resist and silicon structures, fabricated transistor and gate structures (such as tri-grate transistors), using small angle x-ray scattering and/or x-ray diffraction techniques to obtain information such as the determination of critical dimensions, strain within the transistor gate materials, and exemplary parameters that include sidewall angle, pitch, and linewidth roughness. X-ray fluorescence technique may also be used to measure and monitor the composition and amount of element(s) of interest. X-ray fluorescence technique may also be used to measure layer thickness of multiple ROIs of nominally identical film thickness.

Various embodiments of the invention that can examine ROI(s) across a broad range of applications using a combination or a subset of the methods using structured x-ray illumination beam noted above may be used to obtain complementary and comprehensive information of the periodic structures.

This alignment of the periodic illumination to the periodic features can be carried out by observing the overall transmitted x-rays, and either maximizing the transmitted signal (in the case that the periodic objects are more transmissive) or minimizing the transmitted signal (in the case that the periodic structures are more absorbing).

Alignment can also be carried out using, for example, fluorescence, in that a fluorescence signal from the object is detected in any known configuration such as with an x-ray signal detector placed on the same side as the x-ray source relative to the object. The alignment is adjusted until the fluorescence signal detected is maximized if the fluorescence signal for the x-ray energy used is higher from the periodic objects, or minimized if the fluorescence signal is lower for the periodic objects. Additionally, the fluorescence signal may be detected with a detector capable of energy resolution, such as with an energy dispersive spectrometer or a wavelength dispersive spectrometer. With such a detector, specific fluorescence signals may be optimized. For example, the object may be aligned until a specific fluorescence line from the structures or regions of interest is maximized, or until a fluorescence line that would be absent or minimally located at the structures or regions of interest is minimized. One practical example may be minimization of the silicon fluorescence line(s) when the structures of interest are periodic copper structures in a bulk silicon substrate.

Once the illumination beam has been aligned to illuminate the ROI(s), the desired quantity can be measured. The exact protocol will depend on the measurement desired. If, for example, the average thickness of an ensemble of TSVs is the quantity to be measured, the TSVs are aligned to overlap with the high x-ray intensity of a structured x-ray illumination beam. In this example, the transmission and absorption of the x-rays by the TVSs is measured and the average thickness can be determined using established method known in the art. If, for example, the size and size distribution of voids of small dimension in the ensemble of TSVs is the quantity to be measured, the small angle scattering pattern from the TSVs aligned with the periodic x-ray pattern is measured and a known analysis method is used to determine the size and size distribution of the voids. If the sidewalls or coatings of the TSVs are of interest, the periodic x-ray beams may be aligned with not the center of the TSV but instead aligned on one or both sides of a TSV, allowing analysis of such things as sidewall roughness through known methods using small angle scattering.

If, on the other hand, the crystallinity or composition of the periodic object is to be determined, x-ray diffraction signal or x-ray fluorescence signal may be measured. The 3D nature of the structured illumination beam (e.g., intensity variation along the z-direction (beam propagation direction) and the lateral direction can be utilized to analyze, measure, and characterize information around the periodic structures by scanning the object with respect to the structured illumination beam, for example in the z-direction along the illumination beam, so that the point of highest intensity moves through the periodic structures, and correlating the measured signal (such as x-ray diffraction intensity) with the depth where the brightest portion of the periodic x-ray pattern is positioned may allow a determination if the structures have a uniform crystallinity of a predetermined specification.

The data collection will typically be carried out using an x-ray detector with an array of pixels mounted at some distance from the object under examination when absorption, small angle scattering, diffraction, or reflectivity is measured, or an x-ray spectrometer is used when x-ray fluorescence is measured. X-ray intensity will be converted to electronic signals, which are then passed through a connecting cable or a wireless interface to a data storage and analysis system.

Once the measurements have been collected, the measurements are analyzed to calculate or otherwise derive the desired metric. This may be correlated to the physical dimensions of the object, the composition or crystal structure, the local presence or absence of stresses within the periodic object, etc.

This method can be applied to any number of measurement and detection applications, including but not limited to x-ray transmission or absorption measurements, small angle x-ray scattering (SAXS), x-ray fluorescence (XRF) detection, x-ray reflectance (XRR) measurements, and x-ray diffraction (XRD) measurements. Other applications of this method of exposure to x-ray illumination with a structured intensity pattern tuned to the periodicity of an object to be examined will be known to those skilled in the art.

Structured illumination may be used to obtain small angle x-ray scattering (SAXS) information from regions or features of interest. Likewise structured illumination may be used to obtain x-ray fluorescence information from periodic regions within the object under examination. In such an embodiment, the geometry is arranged to conform to a total x-ray fluorescence (TXRF) configuration.

In variations on this embodiment, an x-ray source system of either a microstructured source, a source comprised of linearly accumulating sub-sources, small focus source, or an extended source combined with a multi-slit may be used form a periodic illumination pattern by illuminating a beam splitter and forming a Talbot interference pattern that is incident on an object. Optionally, an optic and a monochromator may be placed between the source and the beamsplitter. This system may be horizontal or vertical. It may be oriented as shown at a small angle of incidence θ, or with an angle of incidence near or at 90°. The detector may be offset to collect x-ray fluorescence emanating from the sample at an angle or alternatively, receive the fluorescence signal after reflection by an optic or multilayer. The detector may be of a wavelength or energy sensitive type such as silicon drift detectors, scintillation detectors, and proportional counters.

In some embodiments, the detector may be placed on the same side of the object as the x-ray source. In this configuration, the detector preferably is a silicon drift detector with a hole through the middle but may be any energy or wavelength sensitive spectrometer. An x-ray optical element may be optionally be used, for x-ray collection, and in some embodiments is preferably a reflective capillary x-ray optic. Alternatively, an aperture or collimating component can be used instead of the optical element. The x-rays that are collimated or focused illuminate the object at periodic regions. Fluorescent x-rays produced by the object are then collected by a detector placed near the object to be investigated to maximize the solid angle of collection.

The x-ray optical elements, configurations and systems that may be applied to embodiments of the invention have been described more fully in the co-pending U.S. patent application entitled X-RAY ILLUMINATORS WITH HIGH FLUX AND HIGH FLUX DENSITY by the inventors of the present invention (U.S. patent application Ser. No. 14/544,191 filed Dec. 5, 2014), in X-RAY SURFACE ANALYSIS AND MEASUREMENT APPARATUS by the inventors of the present invention (U.S. patent application Ser. No. 14/634,834 filed Mar. 1, 2015), and in X-RAY SURFACE ANALYSIS AND MEASUREMENT APPARATUS by the inventors of the present invention (U.S. patent application Ser. No. 15/060,477 filed Mar. 3, 2016), which are all hereby incorporated by reference in their entirety.

Other embodiments of the invention in which the disclosed apparatus is used to obtain x-ray reflectance information from periodic regions within the object under examination may also be used. In this embodiment, the geometry is arranged to conform to an x-ray reflectance (XRR) configuration. As in the previously described fluorescence embodiments, the x-ray source forms a structured illumination beam. As in some of the previously described embodiments, an optional focusing or collimating system may be employed to create a predetermined wavefront profile (converging, diverging, or collimated) for the illumination beam. This focusing or collimating system may additionally be either bandwidth limiting or monochromatizing by inclusion of filtering, monochromatizing, etc. elements.

The object comprising periodic structures is aligned such that the structures of interest are coincident with the periodic pattern of x-rays, and x-rays are reflected from the illuminated surface of the periodic structures. The reflected x-rays are then detected by a detector positioned at some predetermined distance away from the object.

Likewise, structured illumination may be used to obtain x-ray diffraction (XRD) information from periodic structures or features of interest. Some embodiments of an x-ray diffraction system may have a transmission geometry while other embodiments may have a grazing incidence/reflection geometry.

Embodiments may further comprise other components including spectral filters to obtain a desired x-ray energy bandwidth and positioning control systems for all the various components of the system. Systems may be constructed using static anodes or rotating anodes, and systems may additionally have various liquid cooling systems.

It should be noted that certain terms used within this disclosure will be well known to those skilled in the art, such as grids or gratings. In the descriptions here, grids and gratings are terms that may be used interchangeably, and are not meant to be restrictive to a particular grid, period, or pattern.

Likewise, it should be noted that, although these methods and systems may be conveniently used with periodic structures, the structures need not be uniformly periodic to achieve a useful benefit. Gridded structures which are missing certain rows or columns of an array may still provide a useful signal, as will quasi-periodic structures, such as those formed using directed self-assembly (DSA).

Although apparati have been described using periodic structured illumination to produce signals related to small angle x-ray scattering, x-ray fluorescence, x-ray reflectance and x-ray diffraction, these measurement systems are not mutually exclusive, and may be combined to collect information serially or in parallel. The descriptions presented here are not meant to be limiting, and combinations of these embodiments will be apparent to those skilled in the art.

5. Limitations and Extensions

With this application, several embodiments of the invention, including the best mode contemplated by the inventors, have been disclosed. It will be recognized that, while specific embodiments may be presented, elements discussed in detail only for some embodiments may also be applied to others. Also, details and various elements described as part of the prior art, or in the Applications incorporated by reference into the present Application, may also be applied to various embodiments of the invention.

While specific materials, designs, configurations and fabrication steps have been set forth to describe this invention and the preferred embodiments, such descriptions are not intended to be limiting. Modifications and changes may be apparent to those skilled in the art, and it is intended that this invention be limited only by the scope of the appended claims.

We claim:

1. A method for examining an object, comprising:
    creating a structured x-ray illumination beam by bombarding an anode target with electrons to generate x-rays and propagating at least some of the x-rays through an x-ray optical system, said structured x-ray illumination beam propagating along a predetermined direction and having a predetermined intensity profile in a plane perpendicular to the direction at a position of the object, the object comprising one or more regions of interest (ROIs) to be examined, the ROIs comprising one or more features with one or more spatial properties in the plane perpendicular to the direction, the intensity profile of the structured x-ray illumination beam corresponding to at least a portion of the one or more spatial properties of the features of said ROIs;
    positioning at least a portion of said ROIs relative to the structured x-ray illumination beam; and
    detecting x-rays resulting from the interaction of the structured x-ray illumination beam and said ROIs within the object.

2. The method of claim 1, further comprising analyzing the detected x-rays to determine one or more material properties of the object, in which said one or more material properties are selected from the group consisting of: composition, crystallographic structure, chemical state of one or more at least one element, particle size, or particle size distribution.

3. The method of claim 1, in which
    the x-rays resulting from the interaction of the structured x-ray illumination beam and said ROIs within the object arise from one or more phenomena selected from the group consisting of: small angle x-ray scattering, x-ray fluorescence, x-ray reflectivity, x-ray absorption, x-ray refraction, and x-ray diffraction.

4. The method of claim 1, in which bombarding the anode target with electrons produces a structured source and the x-ray optical system forms an image of the structured source at the object with a predetermined magnification.

5. The method of claim 4, in which the predetermined magnification is selected such that at least a portion of the structured x-ray illumination beam incident on the object has a spatial distribution that matches at least a portion of the ROIs.

6. The method of claim 1, in which positioning at least a portion of the ROIs relative to the structured x-ray illumination beam is carried out using an electro-mechanical system.

7. The method of claim 1, in which the anode target comprises a plurality of discrete x-ray generating structures arranged in a pattern corresponding to the ROIs of the object, and creating the structured x-ray illumination beam comprises forming an image of the anode target on the object comprising ROIs using the x-ray optical system.

8. The method of claim 1, in which creating the structured x-ray illumination beam comprises:
    bombarding the anode target with electrons in a pattern corresponding to the ROIs of the object; and
    forming an image of the anode target on the object comprising ROIs using the x-ray optical system.

9. The method of claim 1, in which creating the structured x-ray illumination beam comprises:
    using one or more apertures arranged in a pattern to selectively block x-rays emitted from the anode target, the pattern of the one or more apertures corresponding to the ROIs of the object; and
    forming an image of the one or more apertures on the object comprising ROIs using the x-ray optical system.

10. An apparatus for examining an object, comprising:
    a structured x-ray illumination beam generating system configured to produce a structured x-ray illumination beam having an axis, a predetermined intensity profile in a cross-sectional plane normal to said axis, and propagating towards the object containing one or more regions of interest (ROIs) to be examined, the ROIs comprising one or more features with one or more spatial properties in a plane perpendicular to the direction, the intensity profile of the structured x-ray illumination beam corresponding to at least a portion of the one or more spatial properties of the features of the ROIs, the structured x-ray illumination beam generating system comprising:
        an x-ray source; and
        an x-ray imaging optical system configured to receive x-rays from the x-ray source and to produce the structured x-ray illumination beam, the structured x-ray illumination beam incident on the object;
    at least one x-ray detector for detecting x-rays resulting from the interaction of said structured x-ray illumination beam with said object, and for producing at least one signal corresponding to said detected x-rays; and
    a data collection and analysis system to analyze said at least one signal.

11. The apparatus of claim 10, in which the x-ray source comprises:
    a vacuum chamber;
    an emitter for an electron beam; and
    an anode target comprising a substrate comprising a first material and, embedded in the substrate, a plurality of discrete structures comprising a second material configured to generate x-rays in response to bombardment by electrons.

12. The apparatus of claim 11, in which the first material is selected from the group consisting of: beryllium, diamond, graphite, silicon, boron nitride, silicon carbide, sapphire, and diamond-like carbon; and the second material is selected from the group consisting of: iron, cobalt, nickel, copper, gallium, zinc, yttrium, zirconium, molybdenum, niobium, ruthenium, rhodium, palladium, silver, tin, iridium, tantalum, tungsten, indium, cesium, barium, germanium, gold, platinum, lead, and combinations and alloys thereof.

13. The apparatus of claim 10, in which the x-ray source comprises:
    a vacuum chamber;
    an emitter for an electron beam;
    an anode target comprising a substrate comprising a first material and, coated onto the substrate, a second material configured to generate x-rays in response to bombardment by electrons; and
    an electron beam control system comprising electron optics that directs electron bombardment of said anode target to occur only in specific predetermined positions.

14. The apparatus of claim 13, in which the specific predetermined positions for electron bombardment are positioned to correspond to shapes, sizes, and patterns of the one or more features within the ROIs in the object to be examined.

15. The apparatus of claim 10, in which the x-ray source comprises:
a vacuum chamber;
an emitter for an electron beam;
an anode target comprising a substrate comprising a first material and, coated onto the substrate, a second material configured to generate x-rays in response to bombardment by electrons; and
the structured x-ray illumination beam generating system comprises a screen comprising apertures, in which the apertures are positioned to transmit x-rays generated by the anode target in positions corresponding to shapes, sizes, and patterns of the one or more features within the ROIs in the object to be examined.

16. The apparatus of claim 10, in which the x-ray imaging optical system comprises an optical element selected from the group consisting of: a zone plate, Wolter optics, a reflective optical element, and a compound refractive lens.

17. The apparatus of claim 16, in which a reflecting surface of the Wolter optics comprises multilayers of pairs of materials, said pairs of materials selected from the group of material pairs consisting of: tungsten/carbon (W/C), tungsten/silicon (W/Si), tungsten/tungsten silicide (W/WSi$_2$), molybdenum/silicon (Mo/Si), nickel/carbon (Ni/C), chromium/scandium (Cr/Sc), lanthanum/boron carbide (La/B$_4$C), and tantalum/silicon (Ta/Si).

18. The apparatus of claim 10, in which the x-ray imaging optical system comprises an axially symmetric hollow tube with an inner surface.

19. The apparatus of claim 18, in which
at least a portion of the inner surface of the axially symmetric hollow tube is shaped in the form of a portion of a quadric surface.

20. The apparatus of claim 10, in which
the structured x-ray illumination beam generating system comprises:
a phase grating to generate Talbot interference fringes.

21. The method of claim 6, in which positioning at least a portion of said ROIs relative to the structured x-ray illumination beam is carried out multiple times using a predetermined positioning sequence.

22. The method of claim 21, in which
the predetermined positioning sequence corresponds to a raster scan.

23. The method of claim 21, additionally comprising generating of a map of material properties corresponding to the ROIs sampled according to said predetermined positioning sequence.

24. The method of claim 1, in which the one or more features within the ROIs comprise periodic patterns; and at least a portion of the intensity profile of the structured x-ray illumination beam is periodic and corresponds to the one or more features.

25. The method of claim 24, in which the periodic intensity profile is formed using a phase grating to generate Talbot interference fringes.

26. The apparatus of claim 10, further comprising one or more electro-mechanical systems configured to align the x-ray beam, the object with ROIs, and the detector.

27. The apparatus of claim 26, further comprising a system configured to detect the intensity of x-rays emerging from the object, and to adjust alignment of said ROIs with said structured x-ray illumination beam to optimize the detected x-ray intensity.

28. The apparatus of claim 26, in which the x-rays resulting from the interaction of the structured x-ray illumination beam with the object are produced by a phenomenon selected from the group consisting of: x-ray absorption, x-ray reflection, x-ray refraction, x-ray scattering, x-ray diffraction, and x-ray fluorescence.

29. The method of claim 1, further comprising:
determining the one or more ROIs within the object to be examined;
determining shapes, sizes, and patterns for the one or more features within the
ROIs relative to the predetermined direction;
selecting one or more x-ray techniques to examine the object;
designating the position for the object; and
configuring the detector to detect x-rays emerging from the positioned object appropriate to the selected x-ray techniques.

* * * * *

UNITED STATES PATENT AND TRADEMARK OFFICE
CERTIFICATE OF CORRECTION

PATENT NO.         : 10,401,309 B2
APPLICATION NO.    : 15/173711
DATED              : September 3, 2019
INVENTOR(S)        : Wenbing Yun et al.

It is certified that error appears in the above-identified patent and that said Letters Patent is hereby corrected as shown below:

In the Claims

Column 23, Line 33-34, in Claim 2, change "of one or more" to --of--.

Signed and Sealed this
Tenth Day of December, 2019

Andrei Iancu
*Director of the United States Patent and Trademark Office*